(12) United States Patent
Meyer et al.

(10) Patent No.: US 6,291,745 B1
(45) Date of Patent: Sep. 18, 2001

(54) LIMONENE AND OTHER DOWNSTREAM METABOLITES OF GERANYL PYROPHOSPHATE FOR INSECT CONTROL IN PLANTS

(75) Inventors: Terry EuClaire Meyer, Urbandale; Nasser Yalpani, Johnston, both of IA (US)

(73) Assignee: Pioneer Hi-Bred International, Inc., Des Moines, IA (US)

( * ) Notice: Subject to any disclaimer, the term of this patent is extended or adjusted under 35 U.S.C. 154(b) by 0 days.

(21) Appl. No.: 09/172,339

(22) Filed: Oct. 14, 1998

Related U.S. Application Data

(63) Continuation-in-part of application No. 08/449,061, filed on May 24, 1995, now abandoned, which is a continuation-in-part of application No. 08/153,544, filed on Nov. 16, 1993, now abandoned, which is a division of application No. 08/042,199, filed on Apr. 2, 1993, now abandoned.

(51) Int. Cl.$^7$ .............................. C12N 5/04; C12N 15/29; C12N 15/82; A01H 5/00; A01H 5/10
(52) U.S. Cl. ..................... 800/302; 800/278; 800/286; 800/287; 800/279; 800/320; 800/320.1; 800/320.2; 800/320.3; 800/260; 800/265; 800/298; 800/295; 435/69.1; 435/468; 435/418; 435/419; 536/23.1; 536/23.2; 536/23.6; 536/24.1; 536/24.5
(58) Field of Search .............................. 800/278, 287, 800/286, 302, 279, 320.1, 320.2, 320.3, 320, 260, 265, 298, 295; 435/69.1, 468, 419, 418; 536/23.1, 23.2, 23.6, 24.1, 24.5

(56) References Cited

U.S. PATENT DOCUMENTS

| | | | |
|---|---|---|---|
| 5,023,179 | * | 6/1991 | Lam et al. .................. 435/172.3 |
| 5,107,065 | * | 4/1992 | Shewmaker et al. ............ 800/205 |
| 5,466,785 | * | 11/1995 | De Framond .................. 536/24.1 |
| 5,849,526 | * | 12/1998 | Pichersky .................... 435/69.1 |

FOREIGN PATENT DOCUMENTS

| | | |
|---|---|---|
| WO 9422304 | 10/1994 | (WO) . |
| WO 9511913 | 5/1995 | (WO) . |
| WO 9637102A | 11/1996 | (WO) . |

OTHER PUBLICATIONS

Colby, S.M., et al., 4S–Limonene Synthase from the Oil Glands of Spearmint (*Mentha spicata*), The Journal of Biological Chemistry (1993), pp. 23016–23024, vol. 268, No. 31.

Gordon–Kamm et al. The Plant Cell, vol. 2, pp. 603–618, Jul. 1990.*

Colby et al. J. Cellular Biochem. Suppl. 16 part F, pp. 230, Apr. 1992.*

Coats et al. Chemical Abstracts, vol. 114, pp. 298, 1991.*

Bird et al. Biotech. and Genet. Engineering Review, vol. 9, pp. 207–227, Dec. 1991.*

Sandler et al. Plant Molec. Biol. vol. 11, pp. 301–331, 1988.*

Smith et al. Nature, vol. 334, pp. 724–726, Aug. 1988.*

Chory et al. Plant Physiology, vol. 104, pp. 339–347, 1994.*

Kuipers et al. Mol. Gen Genet. vol. 246, pp. 745–755, 1995.*

Linthorst et al. The Plant Cell, vol. 1, pp. 285–291, Mar. 1989.*

Dandekar et al. Plant Science, vol. 96, pp. 151–161, 1994.*

Belli–Donini, M.L., et al. Relationship Between Peel Damage and the Accumulation of Limonene in Four Varieties of Irradiated Oranges, (1977), vol. 17, pp. 161–165.

Gordon–Kamm, et al. (1990) The Plant Cell. 2603:618.

Colby, S.M., et al. (1992), Isolation and Characterization of cDNA Encoding Limonene Cyclase in Spearmint, *Journal of Cellular Biochemistry*, vol. 16, Part F, p. 230.

Flamm, W.G., et al. (1991), The Human Relevance of the Renal Tumor–Inducing Potential of d–Limonene in Male Rats: Implications of Risk Assessment, *Regulatory Toxicology and Pharmacology*, vol. 13 pp. 70–86.

Baudouy, R., et al. (1989), Synthese Stereoselective D'une Composante De La Pheromone Sexuelle De "L'Escaille Rouge De Californie": L'Acetate D'Isopropenyl–6 Methyl–3.9 YLE, *Tetrahedron*, vol. 45, No. 7, pp. 2067–2074.

Becker, D. and Sahali, Y., (1988), New Synthesis of the California Red Scale Sex Pheromone, *Tetrahedron*, vol. 44, No. 14, pp. 4541–4546.

Watts, M.J. et al. (1984), The Effects of Growth Regulators, Light and Temperature on Flavour Production in Celery Tissue Cultures, *The New Phytologist*, vol. 98, pp. 583–591.

(List continued on next page.)

*Primary Examiner*—David T. Fox
*Assistant Examiner*—Medina A. Ibrahim
(74) *Attorney, Agent, or Firm*—Alston & Bird LLP

(57) ABSTRACT

Methods for manipulating metabolic pathways in plants, particularly those pathways involved in the biosynthesis of monoterpenes are provided. Methods are directed at transforming plants with one or more nucleotide sequences encoding the enzyme GPP synthase, and the monoterpene synthases limonene-, carveol and S-linolool synthase. Methods for creating or enhancing resistance to insects in plants by transforming plants with GPP- and/or monoterpene synthases, to generate plants producing monoterpenes in amounts effective for resistance to insects are also provided.

35 Claims, 13 Drawing Sheets

OTHER PUBLICATIONS

Gambliel, Herve and Croteau, Rodney (1984), Pinene Cyclases I and II, *The Journal of Biological Chemistry*, vol. 259, No. 2, pp. 740–748.

Clegg, Richard J., et al. (1980), Inhibitation of Hepatic Chloesterol Synthesis and S–3–Hydroxy-3 Methylglutaryl–CoA Reductase By Mono and Bicyclic Monoterpenes Administered in Vivo, *Biochemical Pharmacology*, vol. 29, No. 15, pp. 2125–2127.

Belli–Donini, M.L., et al. (1977), Relationship Between Peel Damage and the Accumulation of Limonene in Four Varieties of Irradiated Oranges, vol. 17, pp. 161–165.

Tucker, A.O., et al. (1991), The Origin of Mentha x Gracilis (Lamiaceae). II. Essential Oils, *Economic Botany*, 45(2), pp. 200–215.

Karr, L.L. and Coats, J.R. (1992), Effects of Four Monoterpenoids on Growth and Reproduction of the German Cockroach (Blattodea: Blattellidae), *Entomological Society of America*, pp. 424–429.

Kostal, Vladimir (1992), Orientation Behavior of Newly Hatched Larvae of the Cabbage Maggot, *Delia radicum* (L.)(Diptera: Anthomyiidae), to Volatile Plant Metabolites, *Journal of Insect Behavior*, vol. 5, No. 1, pp. 61–70.

Harwood, Steven H., et al. (1990), Toxicity of Peppermint Monoterpenes to the Varegated Cutworm (Lepidoptera: Noctuidae), *Entomological Society of America*, vol. 83, No. 5, pp. 1761–1767.

Viglierchio, D.R. and Wu, F.F. (1989), Selected Biological Inhibitors for *Heterodera Schachtii* Control, *Nematropica*, vol. 19, No. 1, pp. 75–79.

Lwande, W., et al. (1989), Analysis of Airborne Volatiles of Cowpea, *Phytochemistry*, vol. 28, No. 2, pp. 421–423.

Chang, J.F., et al. (1988), Volatile Monoterpenes Collected From the Air Surrounding Flower Buds of Seven Cotton Genotypes, *Crop Science*, vol. 28, pp. 685–688.

Ahman, I., et al. (1988), Electroantennogram Responses in *Cydia Strobilella* (L.) (Lep., Tortricidae) to Flower and Twig Odours of its Host *Picea Abies* (L.) Karst, *J. App. Ent.*, vol. 105, pp. 314–316.

Hwang, Yih–Shen, et al. (1985), Isolation and Identification of Mosquito Repellants in *Artemisia Vulgaris*, *Journal of Chemical Ecology*, vol. II, No. 9, pp. 1297–1306.

Lund, Eric D., et al. (1982), Components of Meyer Lemon Leaf Oil, *J. Agric. Food Chem.*, vol. 30, No. 1, pp. 95–97.

Honda, Kehchi (1980), Osmeterial Secretions of Papilionid Larvae in the Genera Luehdorfia, Graphium and Atrophaneura (Lepidoptera), *Insect Biochem*, vol. 10, pp. 583–588.

Heath, R.R., et al. (1979), Identification of the White Peach Scale Sex Pheromone, *Journal of Chemical Ecology*, vol, 5, No. 6, pp. 941–953.

Honda, Kehchi (1980), Volatile Constituents of Larval Osmeterial Secretions in *Papilo Protenor Demetrius, J. Insect Physiol.*, vol. 26, pp. 39–45.

Carman, Raymond M. and Klika, Karel D., (1991), The Four Diepoxides of (R)–(+)–Limonene, *Aust. J. Chem.*, vol. 44, pp. 1803–1808.

Uribe, Salvador, et al. (1990), Effects of Cyclohexane, an Industrial Solvent, on the Yeast *Saccharomyces cerevisiae* and on Isolated Yeast Mitochondria, *Applied and Environmental Microbiology*, vol 56, pp. 2114–2119.

Alonso, William R., et al. (1989), Purification of 4S–Limonene Synthase, a Monoterpene Cyclase from the Glandular Trichomes of Peppermint (Mentha x piperita) and Spearmint (*Mentha spicata*), *The Journal of Biological Chemistry*, vol. 267, No. 11, pp. 7582–7587.

Wawrzencyky, C., et al. (1991), Juvenoids with the Limonene System, *Insect Chemical Ecology*, pp. 493–496.

Maffei, Massimo, (1990), F1 and F2 Hybrids from Mentha x verticillata Clone 7303 x *Mentha Spicata* L.A. Chemogenetic Study, *Flavour and Fragrance Journal*, vol. 5, pp. 211–217.

Sakane, et al. (1983) Chiral Leaving Group, Biogenetic–Type Asymmetric Synthesis of Limonene and Bisabolenes, *J. Am. Chem. Soc.*, vol. 105, pp. 6154–6155.

Karr, et al. (1988) Insecticidal Properties of d–Limonene, *J. Pesticide Sci.*, vol. 13, pp. 287–290.

Falk–Filipsson, Agneta (1993) d–Limonene Exposure to Humans by Inhalation: Uptake, Distribution, Elimination, and Effects on the Pulmonary Function, *Journal of Toxicology and Environmental Health*, 38:77–88.

Napali et al. (1990) *Plant Cell* 2:279–289.

Smith et al. (1988) *Nature* 334:724–726.

Coats et al. (1991) *Chemical Abstracts* 114(21):298. Abstract No. 201692y.

Colby et al. (1992) *J. Cellular Biochemistry*. 16 Part F:230. Abstract No. Y405.

Alonso et al. (1992) *J. of Biological Chemistry* 267(11):7582–7587.

Alonso et al. (1991) *Archives of Biochemistry and Biophysics* 286(2):511–517.

Sambrook et al. (1989)*Molecular Cloning A Laboratory Manual*, 2nd. Ed. pp. 11.2–11.19, 11.45–11.49, 11.52–11.61.

Matsuda et al. (1981) *FEBS Letters* 126(1):111–113.

Hilder et al. (1987) *Nature* 330:160–163.

Weising et al. (1988) *Annu. Rev. Genet.* 22:421–477.

Potrykus (1991) *Annu. Rev. Plant Physiol. Plant Mol. Biol.* 42:205–225.

Gordon–Kamm et al. (1990) *The Plant Cell*. 2603–618.

Rajaonarivory et al. (1992) *Diss Abstr. Int. B. 52(10)*:5052. Abstract of 1991 Ph.D. Thesis.

Coats, J.R. et al. "Toxicity and Neurotoxic effects of monoterpenoids in insects and earthworms." ACS Symp. Ser. 1991. 449 (Nat. Occurring Pest Bioregul.), pp. 305–316; Abstracted in Chemical Abstracts 114(21): 201692Y.

* cited by examiner

FIGURE 5

Limonene Synthase Peptide Sequence (599 aa):

```
  1 malkvlsvat qmaipsnltt clqpshfkss pkllsstnss srsrlrvycs ssqltterrs
 61 gnynpsrwdv nfiqsllsdy kedkhviras elvtlvkmel eketdqirql eliddlqrmg
121 lsdhfqnefk eilssiyldh hyyknpfpke erdlystsla frllrehgfq vaqevfdsfk
181 neegefkesl sddtrgllql yeasfllteg ettlesaref atkfleekvn eggvdgdllt
241 riaysldipl hwrikrpnap vwiewyrkrp dmnpvvlela ildlnivqaq fqeelkesfr
301 wwrntgfvek lpfardrlve cyfwntgiie prqhasarim mgkvnalitv iddiydvygt
361 leeleqftdl irrwdinsid qlpdymqlcf lalnnfvddt sydvmkekgv nvipylrqsw
421 vdladkymve arwfygghkp sleeylensw qsisgpcmlt hiffrvtdsf tketvdslyk
481 yhdlvrwssf vlrladdlgt sveevsrgdv pkslqcymsd ynaseaeark hvkwliaevw
541 kkmnaervsk dspfgkdfig cavdlgrmaq lmyhngdghg tqhpiihqqm trtlfepfa
```

FIGURE 6

Limonene Synthase Nucleotide Sequence:

```
   1 agagagagag aggaaggaaa gattaatcat ggctctcaaa gtgttaagtg ttgcaactca
  61 aatggcgatt cctagcaacc taacgacatg tcttcaaccc tcacacttca aatcttctcc
 121 aaaactgtta tctagcacta acagtagtag tcggtctcgc ctccgtgtgt attgctcctc
 181 ctcgcaactc actactgaaa gacgatccgg aaactacaac ccttctcgtt gggatgtcaa
 241 cttcatccaa tcgcttctca gtgactataa ggaggacaaa cacgtgatta gggcttctga
 301 gctggtcact ttggtgaaga tggaactgga gaaagaaacg gatcaaattc gacaacttga
 361 gttgatcgat gacttgcaga ggatgggct gtccgatcat ttccaaaatg agttcaaaga
 421 aatcttgtcc tctatatatc tcgaccatca ctattacaag aacccttttc caaaagaaga
 481 aagggatctc tactccacat ctcttgcatt taggctcctc agagaacatg gttttcaagt
 541 cgcacaagag gtattcgata gtttcaagaa cgaggagggt gagttcaaag aaagccttag
 601 cgacgacacc agaggattgt tgcaactgta tgaagcttcc tttctgttga cggaaggcga
 661 aaccacgctc gagtcagcga gggaattcgc caccaaattt tggaggaaa aagtgaacga
 721 gggtggtgtt gatggcgacc ttttaacaag aatcgcatat tctttggaca tccctcttca
 781 ttggaggatt aaaaggccaa atgcacctgt gtggatcgaa tggtatagga gaggcccga
 841 catgaatcca gtagtgttgg agcttgccat actcgactta atattgttc aagcacaatt
 901 tcaagaagag ctcaaagaat ccttcaggtg gtggagaaat actgggtttg ttgagaagct
 961 gcccttcgca agggatagac tggtggaatg ctactttggg aatactggga tcatcgagcc
1021 acgtcagcat gcaagtgcaa ggataatgat gggcaaagtc aacgctctga ttacggtgat
1081 cgatgatatt tatgatgtct atggcacctt agaagaactc gaacaattca ctgacctcat
1141 tcgaagatgg gatataaact caatcgacca acttcccgat tacatgcaac tgtgctttct
1201 tgcactcaac aacttcgtcg atgatacatc gtacgatgtt atgaaggaga aaggcgtcaa
1261 cgttataccc tacctgcggc aatcgtgggt tgatttggcg ataagtata tggtagaggc
1321 acggtggttc tacggcgggc acaaaccaag tttggaagag tatttggaga actcatggca
1381 gtcgataagt gggccctgta tgttaacgca catattcttc cgagtaacag attcgttcac
1441 aaaggagacc gtcgacagtt tgtacaaata ccacgattta gttcgttggt catccttcgt
1501 tctgcggctt gctgatgatt tggaacctc ggtggaagag gtgagcagag ggatgtgcc
1561 gaaatcactt cagtgctaca tgagtgacta caatgcatcg gaggcggagg cgcggaagca
1621 cgtgaaatgg ctgatagcgg aggtgtggaa gaagatgaat gcggagaggg tgtcgaagga
1681 ttctccattc ggcaaagatt ttataggatg tgcagttgat ttaggaagga tggcgcagtt
1741 gatgtaccat aatggagatg gcacggcac acaacaccct attatacatc aacaaatgac
1801 cagaacctta ttcgagccct ttgcatgaga gatgatgacg agccatcgtt tacttactta
1861 aattctacca aagtttttcg aaggcatagt tcgtaatttt tcaagcacca ataaataagg
1921 agaatcggct caaacaaacg tggcatttgc caccacgtga gcacaaggga gagtctgtcg
1981 tcgtttatgg atgaactatt caatttttat gcatgtaata attaagttca agttcaagag
2041 ccttctgcat atttaactat gtatttgaat ttatcgagtg tgatttctg tctttggcaa
2101 catatatttt tgtcatatgt ggcatcttat tatgatatca tacagtgttt atggatgata
2161 tgatactatc
```

FIGURE 7

GPP Synthase Peptide Sequence (313 aa):

MAINLSHINSKTCFPLKTRSDLSRSSSARCMPTAAAAAFPTIATAAQSQPYWAAIEADIE
RYLKKSITIRPPETVFGPMHHLTFAAPATAASTLCLAACELVGGDRSQAMAAAAAIHLVH
AAAYVHEHLPLTDGSRPVSKPAIQHKYGPNVELLTGDGIVPFGFELLAGSVDPARTDDPD
RILRVIIEISRAGGPEGMISGLHREEEIVDGNTSLDFIEYVCKKKYGEMHACGAACGAIL
GGAAEEEIQKLRNFGLYQTLRGMMEMKNSHQLIDENIIGKLKELALEELGGFHGKNAELM
SSLVAEPSLYAA

FIGURE 8

GPP Synthase Nucleotide Sequence:

TCAAAATGGCCATTAATCTCTCCCATATCAACTCCAAAACATGTTTCCCTCTCAAAACAA
GATCTGATCTCAGCCGTTCTTCTTCCGCGCGTTGCATGCCAACTGCCGCCGCTGCCGCCT
TCCCCACTATCGCCACCGCCGCCCAAAGTCAGCCGTACTGGGCCGCCATCGAGGCCGACA
TAGAGAGATACCTGAAGAAATCCATCACAATAAGGCCGCCGGAGACAGTTTTCGGGCCCA
TGCACCACCTCACCTTCGCCGCCCCAGCCACCGCCGCCTCCACCCTATGCTTGGCGGCGT
GCGAGCTCGTCGGCGGCGACCGAAGCCAAGCCATGGCAGCCGCGGCGGCGATCCATCTCG
TGCACGCGGCAGCCTACGTCCACGAGCACCTCCCTCTAACCGACGGGTCGAGGCCCGTAT
CCAAGCCCGCAATCCAGCACAAGTACGGCCCGAACGTCGAGCTCCTCACCGGAGACGGGA
TTGTCCCGTTCGGGTTTGAGTTGCTGGCCGGGTCAGTGGACCCGGCCCGAACAGACGACC
CGGATAGGATTCTGAGAGTTATAATAGAGATCAGTCGGGCCGGCGGGCCGGAGGGAATGA
TAAGCGGGCTGCATAGGGAAGAAGAAATTGTTGATGGAAATACGAGTTTAGACTTCATTG
AATATGTGTGCAAGAAAAAATACGGCGAGATGCATGCTTGCGGCGCGGCTTGTGGAGCCA
TATTGGGCGGCGCAGCCGAGGAGGAGATTCAGAAGCTGAGGAATTTCGGGCTTTATCAAG
GAACTCTCAGAGGAATGATGGAAATGAAAAATTCTCATCAATTAATTGATGAGAATATAA
TTGGAAAATTGAAAGAATTGGCTCTCGAGGAGTTGGGAGGCTTCCACGGGAAGAACGCTG
AGCTGATGTCGAGCCTTGTAGCCGAGCCGAGCCTTTACGCGGCTTAGAGCTATTCGGATC
CTTCATTGCATTTTCATGCGACATCTTCATATTCATATTGCATAATATTTTTTAAGCCAG
TTATTTTTTTATTATGAATTTTTTTAACTGTTATTGATTTCGAAAATACTGACAATCATC
TAAAATAAAGTAAATATAGTAAGGATGAAAAAAAAAAAAAAAAAAAAAAAA

FIGURE 9A

Carveol Synthase Peptide Sequence:

Met Glu Leu Asp Leu Leu Ser Ala Ile Ile Ile Leu Val Ala Thr Tyr
1           5              10              15

Ile Val Ser Leu Leu Ile Asn Gln Trp Arg Lys Ser Lys Ser Gln Gln
            20              25              30

Asn Leu Pro Pro Ser Pro Pro Lys Leu Pro Val Ile Gly His Leu His
            35              40              45

Phe Leu Trp Gly Gly Leu Pro Gln His Val Phe Arg Ser Ile Ala Gln
            50              55              60

Lys Tyr Gly Pro Val Ala His Val Gln Leu Gly Glu Val Tyr Ser Val
65              70              75              80

Val Leu Ser Ser Ala Glu Ala Ala Pro Gln Ala Met Lys Val Leu Asp
                85              90              95

Pro Asn Phe Ala Asp Arg Phe Asp Gly Ile Gly Ser Arg Thr Met Trp
            100             105             110

Tyr Asp Lys Asp Asp Ile Ile Phe Ser Pro Tyr Asn Asp His Trp Arg
            115             120             125

Gln Met Arg Arg Ile Cys Val Thr Glu Leu Leu Ser Pro Lys Asn Val
            130             135             140

Arg Ser Phe Gly Tyr Ile Arg Gln Glu Glu Ile Glu Arg Leu Ile Arg
145             150             155             160

Leu Leu Gly Ser Ser Gly Gly Ala Pro Val Asp Val Thr Glu Glu Val
                165             170             175

Ser Lys Met Ser Cys Val Val Val Cys Arg Ala Ala Phe Gly Ser Val
                180             185             190

Leu Lys Asp Gln Gly Ser Leu Ala Glu Leu Val Lys Glu Ser Leu Ala
            195             200             205

Leu Ala Ser Gly Phe Glu Leu Ala Asp Leu Tyr Pro Ser Ser Trp Leu
            210             215             220

FIGURE 9B

Leu Asn Leu Leu Ser Leu Asn Lys Tyr Arg Leu Gln Arg Met Arg Arg
225                 230                 235                 240

Arg Leu Asp His Ile Leu Asp Gly Phe Leu Glu Glu His Arg Glu Lys
         245                 250                 255

Lys Ser Gly Asp Phe Gly Gly Glu Asp Ile Val Asp Val Leu Phe Arg
         260                 265                 270

Met Gln Pro Gly Ser Asp Ser Lys Ile Pro Ile Thr Ser Asn Cys Ile
         275                 280                 285

Lys Gly Phe Ile Phe Asp Thr Phe Ser Ala Gly Ala Glu Thr Ser Ser
         290                 295                 300

Thr Thr Ile Ser Trp Ala Leu Ser Glu Leu Met Arg Asn Pro Ala Lys
305                 310                 315                 320

Met Ala Lys Val Gln Ala Glu Val Arg Glu Ala Leu Lys Gly Lys Thr
         325                 330                 335

Val Val Asp Leu Ser Glu Val Gln Glu Leu Lys Tyr Leu Arg Ser Val
         340                 345                 350

Leu Lys Glu Thr Leu Arg Leu His Pro Pro Phe Pro Leu Ile Pro Arg
         355                 360                 365

Gln Ser Arg Glu Glu Cys Glu Val Asn Gly Tyr Thr Ile Pro Ala Lys
         370                 375                 380

Thr Arg Ile Phe Ile Asn Val Trp Ala Ile Gly Arg Asp Pro Gln Tyr
385                 390                 395                 400

Trp Glu Asp Pro Asp Thr Phe Arg Pro Glu Arg Phe Asp Glu Val Ser
            405                 410                 415

Arg Asp Phe Met Gly Asn Asp Phe Glu Phe Ile Pro Phe Gly Ala Gly
            420                 425                 430

Arg Arg Ile Cys Pro Gly Leu His Phe Gly Leu Ala Asn Val Glu Ile
            435                 440                 445

Pro Leu Ala Gln Leu Leu Tyr His Phe Asp Trp Lys Leu Pro Gln Gly
         450                 455                 460

FIGURE 9C

Met Thr Asp Ala Asp Leu Ala Leu Thr Glu Thr Pro Gly Leu Ser Gly
465                470              475              480

Pro Lys Lys Lys Asn Val Cys Leu Val Pro Thr Leu Tyr Lys Ser Pro
           485              490            495

FIGURE 10A
Carveol Synthase Nucleotide Sequence:

| | |
|---|---|
| aaaaaacwaa aaagaaacw atg gag ctc gac ctt ttg tcg gca att ata atc | 52 |
| ctt gtg gca acc tac atc gta tcc ctc cta atc aac caa tgg cga aaa | 100 |
| tcg aaa tcc caa caa aac cta cct ccg agc cct ccg aag ctg ccg gtg | 148 |
| atc ggc cac ctc cac ttc ctg tgg gga ggg ctt ccc cag cac gtg ttt | 196 |
| agg agc ata gcc cag aag tac ggg ccg gtg gcg cac gtg cag ctg gga | 244 |
| gaa gtg tac tcg gtg gtg ctg tcg tcg gcg gag gca gcg ccg cag gcg | 292 |
| atg aag gtg ctg gac ccg aac ttc gcc gac cgg ttc gac ggc atc ggg | 340 |
| tcc agg acc atg tgg tac gac aaa gat gac atc atc ttc agc cct tac | 388 |
| aac gat cac tgg cgc cag atg cgg agg atc tgc gtg aca gag ctg ctg | 436 |
| agc ccg aag aac gtc agg tcc ttc ggg tac ata agg cag gag gag atc | 484 |
| gag cgc ctc atc cgg ctg ctc ggg tcg tcg ggg gga gcg ccg gtc gac | 532 |
| gtg acg gag gag gtg tcg aag atg tcg tgt gtc gtc gtg tgc agg gcg | 580 |
| gcg ttc ggg agt gtg ctc aag gac cag ggt tcg ttg gcg gag ttg gtg | 628 |
| aag gag tcg ctg gca ttg gcg tcc ggg ttt gag ctg gcg gat ctc tac | 676 |
| cct tcc tca tgg ctc ctc aac ctg ctt agc ttg aac aag tac agg ttg | 724 |
| cag agg atg cgc cgc cgc ctc gat cac atc ctt gat ggg ttc ctg gag | 772 |
| gag cat agg gag aag aag agc ggc gac ttt gga ggc gag gac atc gtc | 820 |
| gac gtt ctt ttc agg atg cag ccg ggc agc gac agc aaa att ccc att | 868 |
| act tcc aat tgc atc aag ggt ttc att ttc gac acc ttc tcc gcg gga | 916 |
| gct gaa acg tct tcg acg acc atc tca tgg gcg ttg tcg gaa ctg atg | 964 |
| agg aat ccg gcg aag atg gcc aag gtg cag gcg gag gta aga gag gcg | 1012 |

FIGURE 10B

| | |
|---|---|
| ctc aag gga aag aca gtc gtg gat ttg agc gag gtg caa gag cta aaa | 1060 |
| tac ctg aga tcg gtg tta aag gag act ctg agg ctg cac cct ccc ttt | 1108 |
| cca tta atc cca aga caa tcc agg gaa gaa tgc gag gtt aac ggg tac | 1156 |
| acg att ccg gcc aaa act aga atc ttc atc aac gtc tgg gct atc gga | 1204 |
| agg gat ccc caa tac tgg gaa gat ccc gac acc ttc cgc cct gag aga | 1252 |
| ttc gat gag gtt tcc agg gat ttc atg gga aac gat ttc gag ttc atc | 1300 |
| cca ttc ggg gcg ggt cga aga atc tgc ccc ggt tta cat ttc ggg ctg | 1348 |
| gca aat gtt gag atc cca ttg gcg caa ctg ctc tac cac ttc gac tgg | 1396 |
| aaa ttg cca caa gga atg act gat gcc gac ttg gca ctg acg gag acc | 1444 |
| cca ggt ctt tct ggg cca aaa aag aaa aat gtt tgc ttg gtt ccc aca | 1492 |
| ctc tat aaa agt cct taaccactaa gaagttagca taataagaca tctaaaattg | 1547 |
| tcataatcat ctaattattg ttacacttct tctatcatgt cattttgaga agtgtcttat | 1607 |
| agaggtggcc acggttccgg ttccagttcg gaagcggaac cgaaccatca gttacggttc | 1667 |
| tcagcaagaa gcgaaccgtc ccgccccccc tactgtgttt gagatataaa acacataaaa | 1727 |
| taaaataaaa aaaacgctat ttttttttaa aaaaa | 1762 |

FIGURE 11

S-linalool Synthase Peptide Sequence:

```
            MLITNFSSSSSELQFLVDKVKRESLSSSSSNTQNLFLSTSPYD
TAWLALIPHPHHHHHHGRPMFEKCLQWILHNQTPQGFWAAAGDNISDTDDDVTLDCLL
STLACLVALKRWQLAPDMIHKGLEFVNRNTERLVMKQKPSDVPRWFTIMFPAMLELAG
ASSLRVDFSENLNRILVELSQNRDDILTREEVDEKKQYSPLLLFLEALPAQSYDNDVL
KQIIDKNLSNDGSLLQSPSATARAYMITGNTRCLSYLHSLTNSCSNGGVPSFYPVDDD
LHDLVMVNQLTRSGLTEHLIPEIDHLLLKVQKNYKYKKASPKSLYSIAAELYRDSLAF
WLLRVNNHWVSPSIFCWFLDDDEIRDHIETNYEEFAAVLLNVYRATDLMFSGEVQLVE
ARSFATKNLEKILATGNIHKTNADISSSLHKMIEHELRVPWTARMDHVENRIWIEEIA
SSALWFGKSSYLRLSCFHKMSLQQLAVKNYTLRQLVYRDELAEVERWSKERGLCDMGF
CREKTGYCYYAFAASTCLPWSSDVRLVLTKAAVVITVADDFFDVEGSMVDLEKLTDAV
RRWDAEGLGSHSKTIFEALDDLVNEVRLKCFQQNGQDIKNNLQQLWYETFHSWLMEAK
WGKGLTSKPSVDVYLGNAMTSIAAHTMVLTASCLLGPGFPVHQLWSQRRHQDITSLLM
VLTRLLNDIQSYLKEEDEGKINYVWMYMIENNQASIDDSVRHVQTIINVKKQEFIQRV
LSDQHCNLPKSFKQLHFSCLKVFNMFFNSSNIFDTDTDLLLDIHEAFVSPPQVPKFKP
HIKPPHQLPATLQPPHQPQQIMVNKKKVEMVYKSYHHPFKVFTLQKKQSSGHGTMNPR
ASILAGPNIKLCFS
```

FIGURE 12

S-linalool Synthase Nucleotide Sequence:

AACCAAACCACCTTAAACAAGACAACCATGCAGCTCATAACAAATTTCTCCTCATCATCATCAGAATTGCAG
TTTCTTGTGGATAAGGTTAAGAGAGAATCATTGTCTTCTTCATCATCTAATACTCAGAATTTGTTTCTCTCA
ACTTCACCTTATGACACTGCTTGGCTCGCCCTTATCCCTCATCCTCATCATCACCATCACCATGGCCGACCC
ATGTTTGAAAAATGTCTGCAATGGATTCTCCATAACCAGACACCACAAGGTTTCTGGGCAGCAGCTGGTGAC
AATATTTCCGACACCGACGATGACGTCACCCTGGATTGTCTTCTATCAACCTTGGCTTGCTTAGTTGCACTC
AAAAGGTGGCAGCTTGCTCCCGACATGATTCATAAAGGATTGGAATTTGTAAATAGAAACACAGAGAGACTT
GTAATGAAGCAGAAGCCGAGCGACGTTCCTCGTTGGTTCACCATCATGTTCCCGGCGATGCTCGAGCTTGCC
GGAGCTTCCAGTCTCCGAGTCGATTTCAGCGAGAATCTTAACAGAATCTTGGTGGAACTATCTCAAAATAGG
GATGATATTCTCACAAGGGAGGAAGTTGATGAGAAGAAGCAATACTCACCATTGCTACTATTTCTAGAAGCA
TTGCCTGCACAATCCTATGACAATGATGTTCTAAAGCAAATTATAGACAAGAACTTGAGCAATGATGGTTCT
TTATTGCAATCGCCTTCTGCTACAGCAAGAGCATACATGATAACAGGAAATACCAGATGCTTATCGTATCTA
CACTCTTTAACAAATAGCTGCTCTAATGGAGGAGTACCATCATTCTATCCTGTTGACGACGACCTCCATGAT
CTTGTCATGGTGAATCAACTGACAAGGTCGGGTTTGACTGAACATCTCATCCCGGAGATTGACCACCTTCTA
CTCAAAGTTCAAAAGAACTACAAATACAAAAAAGCATCACCAAAATCATTGTATAGCATTGCTGCGGAACTA
TACAGGGATTCATTAGCATTTTGGTTGCTTCGAGTCAATAATCACTGGGTATCACCATCAATTTTTTGTTGG
TTTTTAGATGACGACGAAATCCGTGATCACATCGAAACAAACTACGAGGAATTTGCTGCCGTGCTTCTTAAT
GTGTATCGAGCTACCGATCTTATGTTCTCCGGCGAAGTCCAACTTGTCGAAGCAAGATCTTTCGCTACCAAG
AATCTTGAGAAAATATTAGCAACAGGAAACATACATAAAACTAATGCAGATATCTCATCTAGTTTGCATAAG
ATGATCGAACACGAACTAAGAGTTCCTTGGACCGCAAGAATGGACCATGTTGAAAATCGAATTTGGATCGAA
GAAATAGCTTCCAGTGCTTTATGGTTTGGAAAATCATCCTACCTTAGGTTATCTTGCTTTCACAAGATGAGT
TTACAGCAACTCGCGGTGAAAAATTATACGCTTCGACAATTGGTTTACCGAGACGAGCTTGCGGAAGTTGAG
AGGTGGTCTAAAGAAAGAGGGCTATGTGACATGGGATTTTGTAGAGAGAAAACCGGGTATTGTTACTACGCA
TTTGCGGCAAGTACTTGTCTGCCGTGGAGTTCCGACGTGAGGCTGGTCCTGACCAAGGCGGCAGTTGTCATT
ACAGTGGCCGATGATTTCTTTGATGTCGAAGGATCTATGGTTGATCTCGAAAAATTAACGGATGCAGTTCGG
AGGTGGGATGCGGAAGGGTTAGGCAGCCACAGCAAGACAATATTTGAAGCCCTGGATGATCTTGTAAATGAA
GTTAGACTCAAGTGTTTCCAACAAAATGGACAAGACATCAAAAACAATCTCCAACAATTATGGTATGAAACA
TTCCATTCATGGCTTATGGAAGCTAAGTGGGGAAAGGGGTTAACAAGTAAACCATCTGTAGATGTGTATCTT
GGAAATGCAATGACATCCATAGCAGCTCACACCATGGTCCTTACAGCATCCTGTCTTCTAGGTCCCGGTTTC
CCGGTTCACCAACTATGGTCGCAAAGGCGCCACCAGGACATTACATCCTTGCTCATGGTCTTGACTCGCTTG
CTAAATGACATTCAATCCTACTTGAAAGAAGAAGACGAAGGAAAAATAAACTATGTATGGATGTACATGATC
GAGAACAATCAAGCGTCGATAGATGACTCGGTTCGACACGTCCAGACGATAATCAATGTAAAAAAGCAAGAA
TTCATCCAACGTGTTCTATCGGATCAACATTGCAATCTCCCAAAGTCATTCAAGCAGCTCCATTTCTCCTGC
CTCAAAGTATTCAACATGTTCTTCAACTCCTCCAACATTTTCGACACTGATACCGACCTTCTTCTTGACATT
CACGAAGCTTTTGTTTCTCCACCACAAGTTCCCAAATTCAAACCCCACATCAAGCCACCTCATCAGCTTCCA
GCAACACTTCAGCCACCTCATCAGCCCCAACAAATAATGGTCAATAAGAAGAAGGTGGAAATGGTTTACAAA
AGCTATCATCATCCATTCAAGGTTTTCACCTTGCAGAAGAAACAAAGTTCGGGACATGGTACAATGAATCCA
AGGGCTAGTATCTTAGCAGGACCCAACATCAAACTATGTTTCAGTTAACGAATACACTACCTTGTTATTAGA
AGATGTCACCAGTTTCC

L1MONENE AND OTHER DOWNSTREAM METABOLITES OF GERANYL PYROPHOSPHATE FOR INSECT CONTROL IN PLANTS

This application is a continuation-in-part of U.S. patent application Ser. No. 08/449,061, filed on May 24, 1995, now abandoned, which is hereby incorporated herein in its entirety by reference, and which is a continuation-in-part of U.S. patent application Ser. No. 08/153,544, filed on Nov. 16, 1993, now abandoned, which was a divisional of U.S. patent application Ser. No. 08/042,199, filed on Apr. 2, 1993, now abandoned.

FIELD OF THE INVENTION

This invention relates to methods for genetic manipulation of metabolic pathways in plants, particularly to transforming plants with genes involved in monoterpene biosynthesis and resistance to insects.

BACKGROUND OF THE INVENTION

Numerous insects are serious pests of common agricultural crops. One method of controlling insects has been to apply insecticidal organic, semiorganic or organometallic chemicals to crops. This method has numerous, art-recognized environmental and public health problems. A more recent method of control of insect pests has been the use of biological control organisms which are typically natural predators of the troublesome insects. These include other insects such as trachonid wasps, fungi such as *Beauveria bassiana,* and bacteria such as *Bacillus thuringiensis* cv., commonly referred to as "Bt". However, it is difficult to apply biological control organisms to large areas, and even more difficult to cause those living organisms to remain in the treated area for an extended period. Still more recently, techniques in recombinant DNA have provided the opportunity to insert into plant cells cloned genes which express insecticidal toxins derived from biological control organisms such as Bt. This technology has given rise to concerns about eventual insect resistance to well-known, naturally occurring insect toxins, particularly in the face of heavy selection pressure, which may occur in some areas. Thus, a continuing need exists to identify naturally occurring insecticidal toxins which can be formed by plant cells directly by expression of structural genes not normally present in the plant.

Southern Corn Rootworm (*Diabrotica undecimpunctata howardi* Barber) is a particularly difficult pest to control or eradicate. It attacks the plant below the soil line, where insecticides are difficult or impossible to apply effectively. In addition, it is resistant to a number of otherwise effective chemical and biological control agents, including Bt toxins and some lectins.

The monoterpene, limonene, 1-methyl-4 (1-methylethenyl) cyclohexene; p-mentha-1,8-diene (Entry No. 5371, Merck Index 11th Ed.), occurs naturally in various ethereal oils, particularly oils of lemon, orange, caraway, dill and bergamot. It is a valuable industrial chemical. Some limonene is prepared by extraction from plants of the mint family, a large quantity is obtained from citrus oils, which are typically 80–90% limonene, and some is obtained from pine oil. It is also synthesized chemically and finds use as a solvent and cleaning agent (in the manufacture of synthetic pine oil), as an expectorant, as a wetting and dispersing agent, as a monomer in the manufacture of various polymeric resins, as a flavorant and a precursor in the synthesis of the flavorant carvone, and as a polymerization inhibitor in storage of the tetrafluoroeoethylene monomer used in the manufacture of polytetrafluoroethylene (PTFE).

Geranyl diphosphate (GPP) synthase catalyzes the first committed step of monoterpene biosynthesis by the condensation of dimethylallyl diphosphate (DMAPP) and isopentenyl diphosphate (IPP) to form GPP, the immediate acyclic precursor of monoterpenes. GPP is converted to (−)-4S-limonene by the catalytic action of (−)-4S-limonene synthase (cyclase). (−)-4S-limonene is converted to (−)-trans-carveol by the action of (−)-trans-carveol synthase, also referred to as limonene-6-hydroxylase. -(−)trans-carveol is converted to carvone by the action of -(−)trans-carveol dehydrogenase, also referred to as carvone synthase. GPP is also converted to the monoterpene S-linalool by the action of S-linalool synthase.

Thus, GPP is the precursor of (−)-4S-limonene and its downstream metabolites (−)-trans-carveol and carvone; as well as the precursor of S-linalool. See FIG. 1; Wise et al. (1997) *In "Comprehensive Natural Products Chemistry: Isoprenoids,* Vol. 2" (Cane, D. E., ed.), Elsevier Science, Oxford (in press); Gershenzon et al. (1989) *Plant Physiol.* 89:1351–1357; Pichersky et al. (1994) *Plant Physiol.* 106:1533–1540. Unlike the mechanistically-related prenyltransferases farnesyl diphosphate (FPP) synthase and geranylgeranyl diphosphate (GGPP) synthase, which produce GPP as intermediates and which are nearly ubiquitous (Ogura et al. (1997) *In "Dynamic Aspects of Natural Products Chemistry"* (Ogura, K. and Sankawa, U., eds.), Kodansha/Harwood Academic Publishers, Tokyo, pp. 1–23), GPP synthase is largely restricted to plant species that produce abundant quantities of monoterpenes.

Because both farnesyl diphosphate synthase and geranylgeranyl diphosphate synthase produce only negligible levels of GPP as a free intermediate on route to FPP and GGPP (Ogura et al. (1997) *In "Dynamic Aspects of Natural Products Chemistry"* (Ogura, K. and Sankawa, U., eds.), Kodansha/Harwood Academic Publishers, Tokyo, pp. 1–23), it is geranyl diphosphate synthase that provides the crucial link between primary metabolism and monoterpene biosynthesis and that serves as the essential driver of monoterpene biosynthesis (Wise et al. (1997) *In "Comprehensive Natural Products Chemistry: Isoprenoids,* Vol. 2" (Cane, D. E., ed.), Elsevier Science, Oxford (in press)).

GPP synthase has been isolated from several plant sources, including grape, geranium, sage (Croteau et al. (1989) *Arch. Biochem. Biophys.* 271:524–535; Heide et al. (1989) *Arch. Biochem. Biophys.* 273:331–338; Suga et al. (1991) *Phytochemistry* 30:1757–1761; Clastre et al. (1993) *Plant Physiol.* 102:205–211); however, the enzyme has not been characterized in any detail, and only the enzyme from grape has been purified to homogeneity.

A cDNA encoding 4S-limonene synthase from oil glands of spearmint has been described in Colby et al. (1993) *J. Biol. Chem.* 268(31): 23016–23024 and is available in the Genbank™/EMBL database and identified by the accession number L13459.

cDNAs encoding S-linalool synthase from *Clarkia breweri* have been described in WO 97/15584, along with methods directed at using the cDNA for enhancing the flavor and smell of plants; and in Dudareva et al. (1996) *Plant Cell* 8 (7): 1137–1148, also available in the Genbank™/EMBL database and identified by the accession number 1491939.

To exploit recombinant methods to increase monoterpene yield in monoterpene-producing species, or to genetically engineer the monoterpene biosynthetic pathway into nonproducing species, it would be highly beneficial to manipulate a GPP synthase gene. Accordingly, the invention relates to expressing GPP synthase in combination with selected monoterpene synthases such as (−)-limonene synthase, S-linalool synthase, and subsequent and related pathway enzymes for production of the corresponding monoterpene product(s).

SUMMARY OF THE INVENTION

The invention provides methods for manipulating metabolic pathways in plants, particularly those pathways that are involved in the biosynthesis of monoterpenes. Methods are directed at transforming plants, plant tissues and cells with one or more nucleotide sequences encoding the enzyme GPP synthase, and the monoterpene synthases limonene-, carveol and S-linolool synthase.

Methods are also provided for creating or enhancing resistance to insects in plants by transforming plants with GPP- and/or monoterpene synthases, to generate plants producing monoterpenes in amounts effective for resistance to insects.

BRIEF DESCRIPTION OF THE DRAWINGS

FIG. 5 sets forth the amino acid sequence for limonene synthase (SEQ ID NO:2).

FIG. 6 sets forth the nucleotide sequence for limonene synthase (SEQ ID NO:1).

FIG. 7 sets forth the amino acid sequence for geranyl pyrophosphate(GPP) synthase (SEQ ID NO:4).

FIG. 8 sets forth the nucleotide sequence for GPP synthase (SEQ ID NO:3).

FIG. 9 sets forth the amino acid sequence for carveol synthase (SEQ ID NO:6).

FIG. 10 sets forth the nucleotide sequence for carveol synthase (SEQ ID NO:5).

FIG. 11 sets forth the amino acid sequence for S-linalool synthase (SEQ ID NO:8).

FIG. 12 sets forth the nucleotide sequence for S-linalool synthase (SEQ ID NO:7).

DETAILED DESCRIPTION OF THE INVENTION

Figure 1:
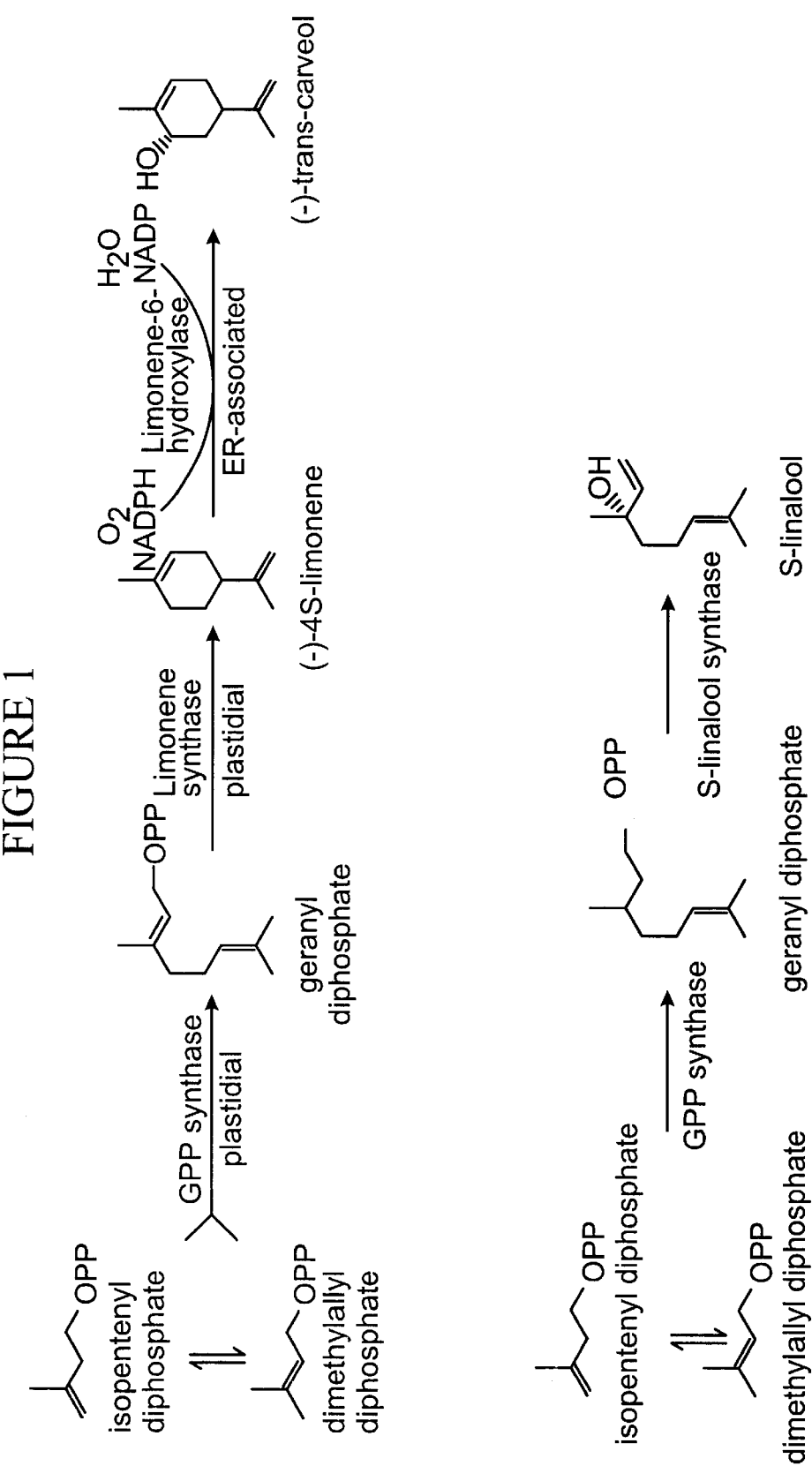
FIG. 1 depicts the biosynthetic pathways involved in production of the monoterpenes limonene, carveol, and S-linalool.

The present invention provides methods for manipulating metabolic pathways in plant cells; particularly those pathways related to synthesis of monoterpenes including but not limited to the monoterpenes (−)-4S-limonene (herein limonene), (−)-trans-carveol (herein carveol) and S-linalool in plants, plant cells and specific plant tissues. These monoterpenes have insecticidal and/or repellent activity against insect pests.

Accordingly, the invention provides methods useful for increasing monoterpene yield in monoterpene-producing species such as mint, and for producing monoterpenes in species which typically do not produce monoterpenes such as maize. The invention also provides methods for creating or enhancing resistance to insects in plants by transforming plants with nucleotide sequences encoding monoterpene synthesis pathway enzymes and generating transformed plants which produce effective amounts of desired monoterpenes in the plant. In this aspect, by "effective amount" is intended that amount of a monoterpene, alone or in combination with other agents, that can effect a reduction, amelioration, prevention, or elimination of a plant-insect interaction.

Thus, the methods of the invention are directed at transforming plant cells with at least one nucleotide sequence encoding a monoterpene synthesis pathway enzyme selected from GPP synthase, limonene synthase, carveol synthase, S-linalool synthase, or combinations thereof.

By "monoterpene synthase" is intended an enzyme which catalyzes a reaction having at least one monoterpene as the product of the reaction. More specifically, monoterpene synthases utilized in the methods of the invention include, but are not limited to limonene synthase, carveol synthase (limonene 6-hydroxylase) and S-linalool synthase.

By "transgenic plant" is meant any plant or plant cell that has become transformed by the introduction, stable and heritable incorporation, into the subject plant or plant cell, of either native DNA that is under the control of a promoter other than the promoter that typically drives expression of that DNA in a wild-type plant, and that has been introduced back into its host plant, or foreign DNA, i.e. DNA encoding for a protein not normally found within that plant species.

"Plantlet" refers to a plant sufficiently developed to have a shoot and a root that is asexually reproduced by cell culture.

"Explant" refers to a section or piece of tissue from any part of a plant for culturing.

The term "callus" and its plural "calli", refer to an unorganized group of cells formed in response to cutting, severing, or other injury inflicted on plant tissue. Excised pieces of plant tissue and isolated cells can be induced to form callus under the appropriate culture conditions. Callus can be maintained in culture for a considerable time by transferring or subculturing parts of the callus to fresh medium at regular intervals. The transfer of callus to liquid medium leads to dispersion of the tissue and the formation of a plant cell suspension culture. Callus can be induced to undergo organized development to form shoots and roots.

"Embryoid" refers to a structure similar in appearance to a plant zygotic embryo.

By the term "taxon" herein is meant a unit of botanical classification of genus or lower. It thus includes genus, species, cultivar, variety, variant, and other minor taxonomic groups that lack a consistent nomenclature.

"Somatic hybrid" and "somatic hybridization" refers generally to stable combination of cellular material, be it protoplast/protoplast or protoplast/cytoplast combinations, and includes cybrids and cybridization.

A "replicon" is any genetic element (e.g., plasmid, chromosome, virus) that functions as a unit of DNA replication in vivo; i.e., capable of replication under its own control.

As used herein, the term "nucleotide sequence" means a DNA or RNA sequence, and can include a cDNA, or genomic DNA, or synthetic DNA sequence, a structural gene or a fragment thereof, or an mRNA sequence, that encodes an active or functional polypeptide.

A "vector" is a replicon, such as a plasmid, phage, or cosmid, to which another DNA segment may be attached so as to bring about the replication of the attached segment.

A DNA "coding sequence" is a DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, procaryotic sequences, cDNA from eucaryotic mRNA, genomic DNA sequences from eucaryotic (e.g., mammalian) DNA, and even synthetic DNA sequences. A polyadenylation signal and transcription termination sequence will usually be located 3' to the coding sequence.

A "promoter sequence" or a "promoter" is a DNA regulatory region capable of binding RNA polymerase in a cell and initiating transcription of a downstream (3' direction) coding sequence. For purposes of defining the present invention, the promoter sequence is bound at its 3' terminus by the translation start codon (ATG) of a coding sequence and extends upstream (5' direction) to include the minimum number of bases or elements necessary to initiate transcription. Within the promoter sequence will be found a transcription initiation site, as well as protein binding domains responsible for the binding of RNA polymerase. Eucaryotic promoters will often, but not always, contain "TATA" boxes and "CAT" boxes.

DNA "control sequences" refers collectively to promoter sequences, ribosome binding sites, polyadenylation signals, transcription termination sequences, upstream regulatory domains, enhancers, and the like, which collectively provide for the transcription and translation of a coding sequence in a host cell.

A coding sequence is "operably linked to" or "under the control of" control sequences in a cell when RNA polymerase will bind the promoter sequence and transcribe the mRNA, which is then translated into the polypeptide encoded by the coding sequence.

A "host cell" is a cell which has been transformed, or is capable of undergoing transformation, by an exogenous DNA sequence.

A cell has been "transformed" by endogenous or exogenous DNA when such DNA has been introduced inside the cell membrane. The DNA may or may not be integrated into (covalently linked to) chromosomal DNA making up the genome of the transformed cell. In procaryotes, for example, the DNA may be maintained on an episomal element, such as a plasmid. With respect to eucaryotic cells, a stably transformed cell is one in which the DNA has become integrated into the chromosome so that it is inherited by daughter cells through chromosome replication. This stability is demonstrated by the ability of the eucaryotic cell to establish cell lines or clones comprised of a population of daughter cells containing the DNA.

A "clone" is a population of cells derived from a single cell or common ancestor by mitosis. A "cell line" is a clone of a primary cell that is capable of stable growth in vitro for many generations.

A "heterologous" region of a DNA construct is an identifiable segment of DNA within or attached to another DNA molecule that is not found in association with the other molecule in nature. Thus, when the heterologous region encodes a bacterial gene, the gene will usually be flanked by DNA that does not flank the bacterial gene in the genome of the source bacterium. Another example of a heterologous coding sequence is a construct where the coding sequence itself is not found in nature (e.g., synthetic sequences having codons different from the native gene). "Heterologous" DNA also refers to DNA not found within the host cell in nature. Allelic variation or naturally occurring mutational events do not give rise to a heterologous region of DNA, as these terms are used herein. "Native", "autologous" or "endogenous" DNA, as used herein, refer to DNA that is typically present in the host in nature.

The term "polypeptide" as used herein is used in its broadest sense, i.e., any polymer of amino acids (dipeptide or greater) linked through peptide bonds. Thus, the term "polypeptide" includes proteins, oligopeptides, protein fragments, analogues, muteins, fusion proteins and the like. The term also encompasses amino acid polymers as described above that include additional non-amino acid moieties. Thus, the term "polypeptide" includes glycoproteins, lipoproteins, phosphoproteins, metalloproteins, nucleoproteins, as well as other conjugated proteins. The term "polypeptide" contemplates polypeptides as defined above that are recombinantly produced, isolated from an appropriate source, or synthesized.

By the term "vector" herein is meant a DNA sequence which is able to replicate and express a foreign gene in a host cell. Typically, the vector has one or more endonuclease recognition sites which may be cut in a predictable fashion by use of the appropriate enzyme. Such vectors are preferably constructed to include additional structural gene sequences imparting antibiotic or herbicide resistance, which then serve as selectable markers to identify and separate transformed cells. Preferred selection agents include kanamycin, chlorosulfuron, phosphinothricin, hygromycin and methotrexate, and preferred markers are genes conferring resistance to these compounds. A cell in which the foreign genetic material in a vector is functionally expressed has been "transformed" by the vector and is referred to as a "transformant." A particularly preferred vector is a plasmid, by which is meant a circular double-stranded DNA molecule that is not a part of the chromosomes of the cell.

In carrying out this invention, it will be appreciated that numerous plant expression cassettes and vectors are well known in the art. By the term "expression cassette" is meant a complete set of control sequences including initiation, promoter and termination sequences which function in a plant cell when they flank a structural gene in the proper reading frame. Expression cassettes frequently and preferably contain an assortment of restriction sites suitable for cleavage and insertion of any desired structural gene. It is important that the cloned gene have a start codon in the correct reading frame for the structural sequence. In addition, the plant expression cassette preferably includes a strong promoter sequence at one end to cause the gene to be transcribed at a high frequency, and a poly-A recognition sequence at the other end for proper processing and transport of the messenger RNA. An example of such a preferred (empty) expression cassette into which the DNA sequence of the present invention can be inserted is the pPH1414 plasmid developed by Beach et al. of Pioneer Hi-Bred International, Inc., Johnston, Iowa. Highly preferred plant expression cassettes are designed to include one or more selectable marker genes, such as kanamycin resistance or herbicide tolerance genes.

Methods of the invention include those for manipulating a metabolic pathway in a plant cell by transforming with nucleotide sequences for native limonene-, GPP-, carveol- and S-linalool synthase genes, by transforming with nucleotide sequences encoding amino acid sequences for the respective proteins encoded thereby, as well as fragments and variants thereof. Such native sequences are set forth in SEQ ID NOs: 1–8. SEQ ID NO:1, SEQ ID NO:3, SEQ ID NO:5 and SEQ ID NO:7 set forth the nucleotide sequences for limonene-, GPP-, carveol-, and S-linalool synthase respectively; the corresponding amino acid sequences set forth in SEQ ID NO:2, SEQ ID NO:4, SEQ ID NO:6 and SEQ ID NO:8 respectively. The methods encompass using the sequences or corresponding antisense sequences in modulating the expression of enzymes involved in monoterpene synthesis, as well as production of monoterpenes in a plant or plant cell. That is, the coding sequences are used to increase the expression of an enzyme while antisense sequences are used to decrease expression. In this aspect, blocking the expression of an enzyme within a pathway by antisense sequences can be used to accumulate the substrates of that enzyme or to drive the pathway to another end product.

It is recognized that the methods of the invention could be used to manipulate metabolic pathways involving reactions downstream of those catalyzed by GPP- and a monoterpene synthase such as limonene-, carveol- and/or S-linalool synthase as described herein; by transforming plants with nucleotide sequences encoding GPP synthase and at least one monoterpene synthase, or antisense sequences thereof In this aspect, the methods of the invention encompass manipulating the pathway involving production of the compounds including but not limited to (−)-carvone, (−)-trans-isopiperitinol and (−)-trans-isopiperitinone.

Antisense RNA or DNA can be utilized for the accumulation of a particular monoterpene. Alternatively, homologous plant sequences or partial plant sequences can be used. For example, an antisense carveol synthase sequence can be used to cause the accumulation of limonene. In this manner, the metabolic pathway of interest can be manipulated for the high production of any particular monoterpene of interest in the pathway.

Likewise, the pathway can be manipulated to decrease levels of a particular compound by transformation of antisense sequences which prevent the conversion of the precursor compound into the particular compound being regulated. For example, conversion of GPP to S-linalool can be blocked by antisense sequences to S-linalool synthase.

In the same manner, to increase the biosynthesis of a particular desired monoterpene, antisense constructs can be used to block the conversion of a common substrate to one monoterpene, thereby shunting the common substrate to the pathway for the desired monoterpene, while additionally blocking downstream conversion of the desired monoterpene to a further downstream metabolite. For example, an antisense sequence to S-linalool synthase can be used to shunt the common substrate GPP to the pathway for limonene biosynthesis, while additionally antisense sequence to carveol synthase can be used to block conversion of limonene to carveol.

Any means for producing a plant comprising GPP- and at least one monoterpene synthase coding sequence are encompassed by the methods of the present invention. For example, the second (or additional) gene of interest can be used to transform a plant at the same time as the GPP synthase gene (cotransformation); the second gene can be introduced into a plant that has already been transformed with the GPP synthase gene; GPP synthase can be transformed into a plant has already been transformed with the second gene; or alternatively, transformed plants, one expressing the GPP synthase and one expressing the second gene, can be crossed to bring the genes together in the same plant. Subsequent crosses or transformations can bring additional sequences together in the plant.

The use of fragments and variants of the nucleotide and amino acid sequences are encompassed within the scope of the invention. By "fragment" is intended a portion of the nucleotide sequence or a portion of the amino acid sequence and hence protein encoded thereby. Fragments of a nucleotide sequence may encode protein fragments that retain the biological activity of the native protein. Alternatively, fragments of a nucleotide sequence that are useful as hybridization probes generally do not encode fragment proteins retaining biological activity. Thus, fragments of a nucleotide sequence may range from at least about 15 nucleotides, about 50 nucleotides, about 100 nucleotides, and up to the entire nucleotide sequence encoding the monoterpene synthase proteins utilized in the methods of the invention. Fragments of the invention include antisense sequences used to decrease expression of the monoterpene synthase genes utilized in the methods of the invention. Such antisense fragments may vary in length ranging from at least about 15 nucleotides, about 50 nucleotides, about 100 nucleotides, up to and including the entire coding sequence.

By "variants" is intended substantially similar sequences. For nucleotide sequences, conservative variants include those sequences that, because of the degeneracy of the genetic code, encode the amino acid sequence of the GPP- and carveol synthase genes. Generally, nucleotide sequence variants of the invention will have at least 70%, generally, 80%, preferably up to 90–95% sequence identity to the native nucleotide sequence.

By "variant" protein is intended a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Such variants may result from, for example, genetic polymorphism or from human manipulation. Methods for such manipulations are generally known in the art.

For example, amino acid sequence variants of the polypeptide can be prepared by mutations in the DNA sequence encoding the native protein of interest. Methods for mutagenesis and nucleotide sequence alterations are well known in the art. See, for example, Walker and Gaastra, eds. (1983) *Techniques in Molecular Biology* (MacMillan Publishing Company, New York); Kunkel (1985) *Proc. Natl. Acad. Sci. U.S.A.* 82:488–492; Kunkel et al. (1987) *Methods Enzymol.* 154:367–382; Sambrook et al. (1989) *Molecular Cloning: A Laboratory Manual* (Cold Spring Harbor, N.Y.); U.S. Pat. No. 4,873,192; and the references cited therein; herein incorporated by reference. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be preferred.

In constructing variants of the limonene-, GPP-, carveol and S-linalool synthase proteins of interest, modifications to the nucleotide sequences encoding the variants will be made such that variants continue to possess the desired activity. Obviously, any mutations made in the DNA encoding the variant protein must not place the sequence out of reading frame and preferably will not create complementary regions that could produce excessive secondary mRNA structure. See EP Patent Application Publication No. 75,444.

Thus, nucleotide sequences utilized in the methods of the invention and the proteins encoded thereby include the native forms as well as variants thereof. The variant proteins will be substantially homologous and functionally equivalent to the native proteins.

A variant of a native protein is "substantially homologous" to the native protein when at least about 80–85%, more preferably at least about 90%, and most preferably at least about 95% of its amino acid sequence is identical to the amino acid sequence of the native protein. DNA sequences that are substantially homologous can be identified in a Southern hybridization experiment under, for example, stringent conditions, as defined for that particular system. Defining appropriate hybridization conditions is within the skill of the art. See, e.g., Maniatis et al. (1982) *Molecular Cloning: A Laboratory Manual*, Cold Spring Harbor Laboratory, New York; Brown, T. A. *Gene Cloning: An Introduction* (2nd Ed.) Chapman & Hall, London (1990).

By "functionally equivalent" is intended that the sequence of the variant defines a chain that produces a protein having substantially the same biological effect as the native protein of interest. Such functionally equivalent variants that comprise substantial sequence variations are also encompassed by the invention. Thus, for purposes of the present invention, a functionally equivalent variant of GPP synthase will catalyze the formation of GPP from dimethylallyl diphosphate (DMAPP) and isopentenyl diphosphate (IPP); that of limonene synthase will catalyze the formation of limonene from GPP; that of carveol synthase will catalyze the formation of carveol from limonene; and that of S-linalool synthase will catalyze the formation of S-linalool from GPP.

In view of the ability to transform crop plants to express various heterologous compounds, it would be desirable to transform maize plants to express monoterpene pathway enzymes and thereby produce effective amounts of the monoterpenes limonene, carveol and/or S-linalool so that by consuming the tissues of the plant an insect, such as larvae of Corn Rootworm, would consume insecticidally effective amounts of the monoterpenes; or be caused to avoid feeding on the plant.

While most gene products are peptides, a monoterpene is not a peptide or peptide derivative and is not expressed from genes in the form of a peptide or peptide derivative, but is produced enzymatically as a secondary metabolite within the cells of some plants. It is determined that the biosynthetic apparatus necessary for the production of the monoterpene limonene may not be present in many plant cells which do not produce limonene, or may not produce detectable, insecticidally effective amounts of limonene, and this appears to include maize cells. Such plant cells must be engineered with at least one enzyme which can be produced through the expression of exogenous (heterologous) genes. One such enzyme is limonene synthase, also known as limonene cyclase, which can directly synthesize limonene from geranyl pyrophosphate (GPP), which is found widely in both procaryotic and eucaryotic cells, although, as discussed below, is in some cases not produced in quantities sufficient to make insecticidally effective amounts of limonene.

Since genes which code for a monoterpene synthase can be synthesized, either directly using a DNA sequence obtained by working backwards from the known amino acid sequence of a particular monoterpene synthase and preferably using plant-preferred codons, or by cloning from natural sources of monoterpenes, the resulting sequence can be inserted into an appropriate expression cassette, and introduced into cells of a susceptible plant species or a suitable endophytic bacterium, so that an especially preferred embodiment of this method involves inserting into the genome of the plant or bacterium a DNA sequence coding for a monoterpene synthase, in proper reading frame relative to transcription initiator and promoter sequences active in the plant or bacterium. Transcription and translation of the coding sequence under control of the regulatory sequences, can cause expression of the enzyme at levels which provide an effective amount of a monoterpene such as limonene in the tissue of the plant which are normally infested by the larvae.

As an illustration, it can be noted that Colby et al., at the Keystone Symposium on Crop Improvement via Biotechnology: An International Perspective, Keystone, Colo., U.S.A., Apr. 10–16, 1992, as reported in *J. Cell Biochem. Suppl.* 16 F, 230 (1992), have isolated and characterized cDNA encoding limonene cyclase from spearmint. To isolate and study the gene(s) (sic) encoding limonene synthase and to produce enough of the enzyme for structural studies, they used standard methods to extract RNA from young leaves of *Mentha spicata* and constructed a cDNA library in λZAP XR (Stratagene) from poly (A)+RNA. They designed three degenerate oligonucleotides based on internal amino acid sequences obtained from Edman degradation of purified limonene synthase and screened 250,000 clones to identify six positive clones that hybridized to all three oligonucleotides. The resulting clones could be used in the methods of this invention which involve plant transformation. However, Colby et al. indicate no appreciation of the value of the enzyme in conferring resistance to insects in plants.

In certain plants, including maize, at least one additional gene encoding GPP synthase is required for generation of plants with resistance to insects. Due to the fact that natural levels of GPP are low in such plants, there may be inadequate amounts of GPP for limonene production in these plants when they are transformed solely with the limonene synthase gene. In contrast, GPP levels in other plant species, such as spearmint, is adequate for limonene production. In such species, some GPP is used to generate limonene, some to generate other metabolites. Because GPP is derived from a pathway that is common among plant species, the introduction of the GPP synthase gene and at least one monoterpene synthase gene such as limonene synthase into plant species lacking GPP can generate transgenic plants capable of producing GPP, and a desired monoterpene at levels effective to confer resistance to insects.

In this manner, the invention encompasses transforming plants with nucleotide sequences encoding GPP synthase and limonene synthase for the generation of plants producing effective amounts of limonene; with nucleotide sequences encoding GPP synthase, limonene synthase and carveol synthase for the generation of plants producing effective amounts of carveol; and with nucleotide sequences encoding GPP synthase and S-linalool synthase for the generation of plants producing effective amounts of S-linalool.

In one embodiment, the plant which can be benefitted by this invention is preferably a plant susceptible to infestation and damage by the larvae of the genus Diabrotica or whose harvested material is subject to attack by larvae of that insect. A prime example is corn (*Zea mays*). Thus the methods of this invention are readily applicable via conventional techniques to numerous plant species, particularly those susceptible to Diabrotica spp., including, without limitation, species from the genera Fragaria, Lotus, Medicago, Onobrychis, Trifolium, Trigonella, Vigna, Citrus, Linum, Geranium, Manicot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Cichorium, Helianthus, Lactuca, Bromus, Asparagus, Antirrhinum, Hemerocallis, Nemesia, Pelargonium, Panicum, Pennisetum, Ranunculus, Senecio, Salpiglossis, Cucumis, Browallia, Glycine, Lolium, Triticum, and Datura.

Thus, the methods of the invention are useful to transform plants and create or enhance resistance to insects in plants. By resistance to insects is intended that the plant-insect interaction, preferably a plant-insect pest interaction, is reduced, ameliorated, prevented, or eliminated.

Insect pests include but are not limited to insects selected from the orders Coleoptera, Diptera, Hymenoptera, Lepidoptera, Mallophaga, Homoptera, Hemiptera, Orthoptera, Thysanoptera, Dermaptera, Isoptera, Anoplura, Siphonaptera, Trichoptera, etc., particularly Coleoptera and Lepidoptera. Insect pests of the invention for the major crops include: Maize: *Ostrinia nubilalis,* European corn borer; *Agrotis ipsilon,* black cutworm; *Helicoverpa zea,* corn earworm; *Spodoptera frugiperda,* fall armyworm; *Diatraea grandiosella,* southwestern corn borer; *Elasmopalpus lignosellus,* lesser cornstalk borer; *Diatraea saccharalis,* surgarcane borer, *Diabrotica virgifera,* western corn rootworm; *Diabrotica longicornis barberi,* northern corn rootworm; *Diabrotica undecimpunctata howardi,* southern corn rootworm; Melanotus spp., wireworms; *Cyclocephala borealis,* northern masked chafer (white grub); *Cyclocephala immaculata,* southern masked chafer (white grub); *Popilia japonica,* Japanese beetle; *Chaetocnema pulicaria,* corn flea beetle; *Sphenophorus maidis,* maize billbug; *Rhopalosiphum maidis,* corn leaf aphid; *Anuraphis maidiradicis,* corn root aphid; *Blissus leucopterus leucopterus,* chinch bug; *Melanoplus femurrubrum,* redlegged grasshopper; *Melanoplus sanguinipes,* migratory grasshopper; *Hylemya platura,* seedcorn maggot; *Agromyza parvicornis,* corn blot leafminer; *Anaphothrips obscrurus,* grass thrips; *Solenopsis milesta,* thief ant; *Tetranychus urticae,* twospotted spider mite; Sorghum: *Chilo partellus,* sorghum borer; *Spodoptera frugiperda,* fall armyworm; *Helicoverpa zea,* corn earworm; *Elasmopalpus lignosellus,* lesser cornstalk borer; *Feltia subterranea,* granulate cutworm; *Phyllophaga crinita,* white grub; Eleodes, Conoderus, and Aeolus spp., wireworms; *Oulema melanopus,* cereal leaf beetle; *Chaetocnema pulicaria,* corn flea beetle; *Sphenophorus maidis,* maize billbug; *Rhopalosiphum maidis;* corn leaf aphid; *Sipha flava,* yellow sugarcane aphid; *Blissus leucopterus leucopterus,* chinch bug; *Contarinia sorghicola,* sorghum midge; *Tetranychus cinnabarinus,* carmine spider mite; *Tetranychus urticae,* twospotted spider mite; Wheat: *Pseudaletia unipunctata,* army worm; *Spodoptera frugiperda,* fall armyworm; *Elasmopalpus lignosellus,* lesser cornstalk borer; *Agrotis orthogonia,* western cutworm; *Elasmopaipus lignosellus,* lesser cornstalk borer; *Oulema melanopus,* cereal leaf beetle; *Hypera punctata,* clover leaf weevil; *Diabrotica undecimpunctata howardi,* southern corn rootworm; Russian wheat aphid; *Schizaphis graminum,* greenbug; *Macrosiphum avenae,* English grain aphid; *Melanoplus femurrubrum,* redlegged grasshopper; *Melanoplus differentialis,* differential grasshopper; *Melanoplus sanguinipes,* migratory grasshopper; *Mayetiola destructor,* Hessian fly; *Sitodiplosis mosellana,* wheat midge; *Meromyza americana,* wheat stem maggot; *Hylemya coarctata,* wheat bulb fly; *Frankliniella fusca,* tobacco thrips; *Cephus cinctus,* wheat stem sawfly; *Aceria tulipae,* wheat curl mite; Sunflower: *Suleima helianthana,* sunflower bud moth; *Homoeosoma electellum,* sunflower moth; *Zygogramma exclamationis,* sunflower beetle; *Bothyrus gibbosus,* carrot beetle; *Neolasioptera murtfeldtiana,* sunflower seed midge; Cotton: *Heliothis virescens,* cotton budworm; *Helicoverpa zea,* cotton bollworm; *Spodoptera exigua,* beet armyworm; *Pectinophora gossypiella,* pink bollworm; *Anthonomus grandis,* boll weevil; *Aphis gossypii,* cotton aphid; *Pseudatomoscelis seriatus,* cotton fleahopper; *Trialeurodes abutilonea,* bandedwinged whitefly; *Lygus lineolaris,* tarnished plant bug; *Melanoplus femurrubrum,* redlegged grasshopper; *Melanoplus differentialis,* differential grasshopper; *Thrips tabaci,* onion thrips; *Franklinkiella fusca,* tobacco thrips; *Tetranychus cinnabarinus,* carmine spider mite; *Tetranychus urticae,* twospotted spider mite; Rice: *Diatraea saccharalis,* sugarcane borer; *Spodoptera frugiperda,* fall armyworm; *Helicoverpa zea,* corn earworm; *Colaspis brunnea,* grape colaspis; *Lissorhoptrus oryzophilus,* rice water weevil; *Sitophilus oryzae,* rice weevil; *Nephotettix nigropictus,* rice leafhopper; *Blissus leucopterus leucopterus,* chinch bug; *Acrosternum hilare,* green stink bug; Soybean: *Pseudoplusia includens,* soybean looper; *Anticarsia gemmatalis,* velvetbean caterpillar; *Plathypena scabra,* green cloverworm; *Ostrinia nubilalis,* European corn borer; *Agrotis ipsilon,* black cutworm; *Spodoptera exigua,* beet armyworm; *Heliothis virescens,* cotton budworm; *Helicoverpa zea,* cotton bollworm; *Epilachna varivestis,* Mexican bean beetle; *Myzus persicae,* green peach aphid; *Empoasca fabae,* potato leafhopper; *Acrosternum hilare,* green stink bug; *Melanoplus femurrubrum,* redlegged grasshopper; *Melanoplus differentialis,* differential grasshopper; *Hylemya platura,* seedcorn maggot; *Sericothrips variabilis,* soybean thrips; *Thrips tabaci,* onion thrips; *Tetranychus turkestani,* strawberry spider mite; *Tetranychus urticae,* twospotted spider mite; Barley: *Ostrinia nubilalis,* European corn borer; *Agrotis ipsilon,* black cutworm; *Schizaphis gramium,* greenbug; *Blissus leucopterus leucopterus,* chinch bug; *Acrosternum hilare,* green stink bug; *Euschistus servus,* brown stink bug; *Delia platura,* seedcorn maggot; *Mayetiola destructor,* Hessian fly; *Petrobia latens,* brown wheat mite; Oil Seed Rape: *Brevicoryne brassicae,* cabbage aphid; *Phyllotreta cruciferae,* Flea beetle; *Mamestra configurata,* Bertha armyworm; *Plutella xylostella,* Diamond-back moth; Delia ssp., Root maggots.

Preferred plants that are to be transformed according to the methods of this invention are cereal crops, including maize, rye, barley, wheat, sorghum, oats, millet, rice, triticale, sunflower, alfalfa, rapeseed and soybean, fiber crops, such as cotton, fruit crops, such as melons, and vegetable crops, including onion, pepper, tomato, cucumber, squash, carrot, crucifer (cabbage, broccoli, cauliflower), eggplant, spinach, potato and lettuce.

While compounds other than monoterpenes have some effective insecticidal activity at high concentrations in pure form, plant cell expression at such high concentrations is either not possible in a living plant cell system, or is not feasible if the commercially useful characteristics of the plant are to be preserved in terms of production of oils, starches, fibers, or other materials. Monoterpenes, on the other hand, are not directly expressed as the gene product, and the peptide or peptides which is or are expressed in the methods of this invention is an enzyme which can catalyze the synthesis of large amounts of a monoterpene(s) in the tissues of the transformed plant (e.g. limonene synthase), and in instances in which it is required, an enzyme which can catalyze the synthesis of large amounts of substrate for a downstream monoterpene synthase (e.g. GPP synthase).

The genes utilized in the invention, including GPP-, carveol, limonene-, and S-linalool synthase genes can be optimized for enhanced expression in plants of interest. See, for example, EPA0359472; WO91/16432; Perlak et al. (1991) *Proc. Natl. Acad. Sci. U.S.A.* 88:3324–3328; and Murray et al. (1989) *Nucleic Acids Res.* 17:477–498. In this manner, the genes can be synthesized utilizing plant-preferred condons. See, for example, Murray et al. (1989) *Nucleic Acids Res.* 17:477–498, the disclosure of which is incorporated herein by reference. In this manner, synthetic genes can also be made based on the distribution of codons a particular host uses for a particular amino acid. Thus, the nucleotide sequences can be optimized for expression in any plant. It is recognized that all or any part of the gene sequence may be optimized or synthetic. That is, synthetic or partially optimized sequences may also be used.

The methods of the invention encompass utilizing naturally occurring nucleotide sequences encoding GPP synthase, and the monoterpene synthases limonene-, carveol- and S-linalool synthases; or utilizing synthetically derived sequences encoding these proteins. The naturally occurring nucleotide sequences utilized in the methods of the invention are set forth in SEQ ID NOs: 1, 3, 5, and 7.

The methods also encompass utilizing nucleotide sequences isolated from various organisms including plants by hybridization with partial sequences obtained from the natural sequences as set forth above. Conditions that will permit other DNA sequences to hybridize to the DNA sequences set forth herein can be determined in accordance with techniques generally known in the art. For example, hybridization of such sequences may be carried out under conditions of reduced stringency, medium stringency, or high stringency conditions (e.g., conditions represented by a wash stringency of 35–40% Formamide with 5xDenhardt's solution, 0.5% SDS, and 1xSSPE at 37° C.; conditions represented by a wash stringency of 40–45% Formamide with 5xDenhardt's solution, 0.5% SDS, and 1xSSPE at 42° C.; and conditions represented by a wash stringency of 50% Formamide with 5xDenhardt's solution, 0.5% SDS, and 1xSSPE at 42° C., respectively. See Sambrook et al. (1989) *Molecular Cloning: A Laboratory Manual* (2d ed., Cold Spring Harbor Laboratory Press, Plainview, N.Y.). The methods further encompass utilizing nucleotide sequences isolated from various organisms including plants by other well known methods such as PCR using the natural sequences as set forth above.

The methods of the invention comprise utilizing expression cassettes with constitutive or tissue-specific promoters. Promoters that may be used in the expression cassettes include without limitation nos, ocs, phaseolin, FMV and other promoters isolated from the DNA of plants or other sources, both natural and synthetic.

Constitutive promoters would provide a constant production of the enzymes GPP-, limonene-, carveol and/or S-linalool synthase and thereby the corresponding monoterpene(s). Such constitutive promoters include, for example, the core promoter of the Rsyn7 (U.S. patent application Ser. No. 08/661,601), the core CaMV 35S promoter (Odell et al. (1985) *Nature* 313:810–812); rice actin (McElroy et al. (1990) *Plant Cell* 2:163–171); ubiquitin (Christensen et al. (1989) *Plant Mol. Biol.* 12:619–632 and Christensen et al. (1992) *Plant Mol. Biol.* 18:675–689); pEMU (Last et al. (1991) *Theor. Appl. Genet.* 81:581–588); MAS (Velten et al. (1984) *EMBO J.* 3:2723–2730); ALS promoter (U.S. patent application Ser. No. 08/409,297), and the like. Other constitutive promoters include, for example, U.S. Pat. Nos. 5,608,149; 5,608,144; 5,604,121; 5,569,597; 5,466,785; 5,399,680; 5,268,463; and 5,608,142.

An efficient plant promoter that may be used is an overproducing plant promoter. Overproducing plant promoters that may be used in this invention include the promoter of the small sub-unit (ss) of the ribulose-1,5-bisphosphate carboxylase from soybean (Berry-Lowe et al. (1982) *J. Mol. and App. Gen.* 1:483–498, and the promoter of the chlorophyll a–b binding protein. However, these two promoters are known to be light-induced in eukaryotic plant cells (see, for example, *Genetic Engineering of Plants, An Agricultural Perspective,* Cashmore, Pelham, N.Y., 1983, pp. 29–38, G. Coruzzi et al. (1983) *J. Biol. Chem.* 258:1399 and P. Dunsmuir et al. (1983) *J. Mol. and App. Gen.* 2:285 and may be less desirable when root expression is desired.

A tissue-specific promoter (or promoters) can be used in any instance where it may be desirable to localize production of the desired monoterpene to an insect-infested tissue or to a tissue which is efficient in production of a desired enzyme. The utilization of tissue-specific promoters would increase or decrease the expression of monoterpene synthases and production of the corresponding monoterpenes in specific tissues of the plant. It is recognized that in manipulating the level of monoterpene production as such, it may be desirable to increase or decrease the levels of such molecules in a particular tissue, since tolerance of various tissues to increased expression of specific monoterpenes may vary. Thus, it may be desirable to increase expression in selected tissues, or at varying levels in different tissues by the use of tissue-specific promoters.

Particular tissue-specific promoters of interest includes root-preferred promoters. The utilization of such promoters would provide a method of selectively creating or enhancing resistance to insects, and/or manipulating levels of monoterpene molecules in the root. Since corn rootworm attack roots, root-specific promoters are especially preferred for the control of corn rootworm, while minimizing limonene production in the agronomically valuable parts of the plant. Such selectivity could also be particularly desirable in plants in which the root constitutes the food crop, including, but not limited to carrot, potato, radish, and the like.

Root specific promoters are known and can be selected from the many available from the literature or isolated de novo from various compatible species. For example, Hire, et al (1992) *Plant Mol. Biology,* 20(2): 207–218, describe a root-specific glutamine synthetase gene from soybean. Keller and Baumgartner, (1991) *The Plant Cell,* 3(10): 1051–1061, describe a root-specific control element in the GRP 1.8 gene of French bean. Sanger et al. (1990) *Plant Mol. Biology,* 14(3): 433–443, discuss the root-specific promoter of the Mannopine Synthase (MAS) gene of *Agrobacterium tumefaciens.* Miao et al. (1991) *The Plant Cell,* 3(1): 11–22, describe a full-length cDNA clone encoding cytosolic glutamine synthetase (GS), which is expressed in roots and root nodules of soybean. Bogusz et al. (1990) *The Plant Cell,* 2(7): 633–641, discusses two root-specific promoters isolated from hemoglobin genes from the nitrogen-fixing nonlegume *Parasponia andersonii* and the related non-nitrogen-fixing nonlegume *Trema tomentosa.* The promoters of these genes were linked to a β-glucuronidase reporter gene and introduced into both the nonlegume *Nicotiana tabacum* and the legume *Lotus corniculatus,* and in both instances root-specific promoter activity was preserved. Leach and Aoyagi (1991) *Plant Science* (Limerick) 79(1): 69–76, describe their analysis of the promoters of the highly expressed rolC and rolD root-inducing genes of *Agrobacterium rhizogenes.* They concluded that enhancer and tissue-specific DNA determinants are dissociated in those promoters. Teeri et al. (1989) *EMBO Journal,* 8(2): 343–350, used gene fusion to lacZ to show that the Agrobacterium T-DNA gene encoding octopine synthase is especially active in the epidermis of the root tip and that the TR2' gene was root specific in the intact plant and stimulated by wounding in leaf tissue, an especially desirable combination of characteristics for use with an insecticidal or larvicidal gene. The TR1' gene, fused to NPTII, (neomycin phosphotransferase II) showed similar characteristics. Additional root-preferred promoters include the VfENOD-GRP3 gene promoter (Kuster H et al. (1995) *Plant Mol. Biol.* 29(4):759–772); and rolB promoter (Capana et al. (1994) *Plant Mol. Biol.* 25(4) :681–691. See also U.S. Pat. Nos. 5,633,363; 5,459,252; 5,401,836; 5,110,732; and 5,023,179.

Other tissue-specific promoters include those described in Yamamoto et al. (1997) *Plant J.* 12(2):255–265; Kawamata et al. (1997) *Plant Cell Physiol.* 38(7):792–803; Hansen et al. (1997) *Mol. Gen. Genet.* 254(3):337–343; Russell et al. (1997) *Transgenic Res.* 6(2):157–168; Rinehart et al. (1996) *Plant Physiol.* 112(3):1331–1341; Van Camp et al. (1996) *Plant Physiol.* 112(2):525–535; Canevascini et al. (1996) *Plant Physiol.* 112(2):513–524; Yamamoto et al. (1994) *Plant Cell Physiol.* 35(5):773–778; Lam (1994) *Results Probl. Cell Differ.* 20:181–196; Orozco et al. (1993) *Plant Mol. Biol.* 23(6):1129–1138; Matsuoka et al. (1993) *Proc. Natl. Acad. Sci. U.S.A.* 90(20):9586–9590; and Guevara-Garcia et al. (1993) *Plant J.* 4(3):495–505.

Seed-preferred promoters includes both seed-specific promoters (those promoters active during seed development) as well as seed-germinating promoters (those promoters active during seed germination). Such promoters include Cim1 (cytokinin-induced message); cZ19B1 (maize 19 KDa zein); milps (myo-inositol-1-phosphate synthase); celA (cellulose synthase); end1 (*Hordeum verlgase* mRNA clone END1); and imp3 (myo-inositol monophosphate-3). For dicots, particular promoters include phaseolin, napin, β-conglycinin, soybean lectin, and the like. For monocots, particular promoters include maize 15 Kd zein, 22 KD zein, 27 kD zein, waxy, shrnmken 1, shrunken 2, globulin 1, etc.

In native tissues which synthesize monoterpenes, GPP-, limonene- and S-linalool synthases are targeted to plastids via plastid targeting sequences (transit peptides) typically contained at the N-terminus of the preprotein forms of the enzymes. The targeting sequences are then cleaved to release the mature enzymes in plastids. Such transit peptides can be identified in the primary amino acid sequences of the preproteins by those ordinarily skilled in the art. For example, see Colby et al. (1993) *J. Biol. Chem.* 268(31) :23016–23024, for the transit peptide sequence of limonene synthase. Native carveol synthase is associated with the endoplasmic reticulum, while native carveol dehydrogenase could be cytoplasmic.

Furthermore, the substrates of GPP synthase, IPP (IDP) and DMAPP (DMADP) can be found in plastids or in the cytoplasm (Bohlmann et al. (1998) *Proc. Natl. Acad. Sci. U.S.A.* 95:4126–4133). In plastids, these substrates are most likely synthesized via the glyceraldehyde-3-phosphate/ pyruvate (Robmer) pathway, and in the cytosol via the mevalonate pathway in the cytosol or the mevalonate pathway.

Thus, for manipulating a metabolic pathway involving monoterpene production, it would be beneficial to target GPP-, limonene-, and S-linalool synthase to plastids; and carveol synthase and dehydrogenase to the endoplasmic reticulum (ER). This targeting could be achieved by use of the native targeting sequences contained in the sequences of the native proteins, or by addition or exchange of heterologous subcellular targeting signals. Alternatively, the enzymes utilized in the methods of the invention could be directed to the cytoplasm by deletion of the plastid and/or ER targeting signals. Methods for deletion, exchange and addition of nucleotide sequences are well known in the art, and can be readily used for manipulation of nucleotide segments encoding targeting signals of interest as described herein.

Heterologous sequences which can be used to target the desired enzymes of the invention to plastids include chloroplast targeting sequences. Chloroplast targeting sequences are known in the art and include the chloroplast small subunit of ribulose-1,5-bisphosphate carboxylase (Rubisco), (de Castro Silva Filho et al. (1996) *Plant Mol. Biol.* 30:769–780; Schnell, et al. (1991) *J. Biol. Chem.* 266(5) :3335–3342); 5-(enolpyruvyl)shikinate-3-phosphate synthase (EPSPS) (Archer et al. (1990) *J. Bioenerg. Biomemb.* 22(6):789–810); tryptophan synthase (Zhao et al. (1995) *J. Biol. Chem.* 270(11):6081–6087); plastocyanin (Lawrence et al. (1997) *J. Biol. Chem.* 272(33):20357–20363); chorismate synthase (Schmidt et al. (1993) *J. Biol. Chem.* 268(36) :27477–27457); and the light harvesting chlorophyll a/b binding protein (LHBP) (Lamppa et al. (1988) *J. Biol. Chem.* 263: 14996–14999). See also Von Heijne et al. (1991) *Plant Mol. Biol. Rep.* 9:104–126; Clark et al. (1989) *J. Biol. Chem.* 264:17544–17550; della-Cioppa et al. (1987) *Plant Physiol.* 84:965–968; Romer et al. (1993) *Biochem. Biophys. Res Commun.* 196:1414–1421; and Shah et al. (1986) *Science* 233:478–481.

Likewise, methods for transformation of chloroplasts are known in the art. See, for example, Svab et al. (1990) *Proc. Natl. Acad. Sci. U.S.A.* 87:8526–8530; Svab and Maliga (1993) *Proc. Natl. Acad. Sci. U.S.A.* 90:913–917; Staub and Maliga (1993) *Embo J.* 12:601–606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-specific expression of a nuclear-encoded and plastid-directed RNA polymerase. Such a system has been reported in McBride et al. (1994) *Proc. Natl. Acad. Sci. U.S.A.* 91:7301–7305.

The nucleotide sequences utilized in methods of the invention can be introduced into any plant. The sequences to be introduced may be used in expression cassettes for expression in any plant of interest where expression in the plant is necessary for transcription.

While it may be preferable to express the sequences using heterologous promoters, the native promoter sequences may be used. Such constructs would change expression levels of the enzymes of the invention in the plant or plant cell. Thus, the phenotype of the plant or plant cell is altered.

Where expression cassettes are needed, such expression cassettes will comprise a transcriptional initiation region linked to the coding sequence or antisense sequence of the nucleotide of interest. Such an expression cassette is provided with a plurality of restriction sites for insertion of the sequence to be under the transcriptional regulation of the regulatory regions. The expression cassette may additionally contain selectable marker genes.

The transcriptional initiation region, the promoter, may be native or analogous or foreign or heterologous to the plant host. Additionally, the promoter may be the natural sequence or alternatively a synthetic sequence. By foreign is intended that the transcriptional initiation region is not found in the native plant into which the transcriptional initiation region is introduced. As used herein a chimeric gene comprises a coding sequence operably linked to a transcription initiation region that is heterologous to the coding sequence.

The transcriptional cassette will include in the 5'-to-3' direction of transcription, a transcriptional and translational initiation region, a DNA sequence of interest, and a transcriptional and translational termination region functional in plants. The termination region may be native with the transcriptional initiation region, may be native with the DNA sequence of interest, or may be derived from another source. Convenient termination regions are available from the Ti-plasmid of *A. tumefaciens,* such as the octopine synthase and nopaline synthase termination regions. See also Guerineau et al. (1991) *Mol. Gen. Genet.* 262:141–144; Proudfoot (1991) *Cell* 64:671–674; Sanfacon et al. (1991) *Genes Dev.* 5:141–149; Mogen et al. (1990) *Plant Cell.* 2:1261–1272; Munroe et al. (1990) *Gene* 91:151–158; Ballas et al. (1989) *Nucleic Acids Res.* 17:7891–7903; Joshi et al. (1987) *Nucleic Acids Res.* 15:9627–9639.

The methods of the invention encompass use of expression cassettes for expression of nucleotide sequences encoding GPP- and monoterpene synthases in the plant of interest. The cassette will include 5' and 3' regulatory sequences operably linked to the sequence of interest. The cassette may additionally contain at least one additional sequence to be cotransformed into the organism. Alternatively, the additional sequence(s) can be provided on another expression cassette.

Where appropriate, sequences utilized in the methods of the invention and additional gene(s) may be optimized for increased expression in the transformed plant. That is, these nucleotide sequences can be synthesized using plant preferred codons for improved expression. Methods are available in the art for synthesizing plant preferred genes. See, for example, U.S. Pat. Nos. 5,380,831, 5,436,391, and Murray et al. (1989) *Nucleic Acids Res.* 17:477–498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences which may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Nat. Acad. Sci. U.S.A.* 86:6126–6130); potyvirus leaders, for example, TEV leader (Tobacco Etch Virus) (Allison et al. (1986)); MDMV leader (Maize Dwarf Mosaic Virus) (*Virology* 154:9–20); human immunoglobulin heavy-chain binding protein (BiP) (Macejak and Sarnow (1991) *Nature* 353:90–94); untranslated leader from the coat protein mRNA of alfalfa mosaic virus (AMV RNA 4) (Jobling and Gehrke (1987) *Nature* 325:622–625); tobacco mosaic virus leader (TMV) (Gallie et al. (1989) *Molecular Biology of RNA,* pages 237–256); and maize chlorotic mottle virus leader (MCMV) (Lommel et al. (1991) *Virology* 81:382–385). See also Della-Cioppa et al. (1987) *Plant Physiology* 84:965–968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

The methods of the invention can be used in transforming or transfecting any plant. In this manner, genetically modified plants, plant cells, plant tissue, seed, and the like can be obtained. Transformation protocols as well as protocols for introducing nucleotide sequences into plants may vary depending on the type of plant or plant cell, i.e. monocot or dicot, targeted for transformation. Suitable methods of introducing nucleotide sequences into plant cells and subsequent insertion into the plant genome include microinjection (Crossway et al. (1986) *Biotechniques* 4:320–334), electroporation (Riggs et al. (1986) *Proc. Natl. Acad. Sci. U.S.A.* 83:5602–5606, Agrobacterium-mediated transformation (Hinchee et al. (1988) *Biotechnology* 6:915–921), direct gene transfer (Paszkowski et al. (1984) *EMBO J.* 3:2717–2722), and ballistic particle acceleration (see, for example, Sanford et al., U.S. Pat. No. 4,945,050; Tomes et al. (1995) "Direct DNA Transfer into Intact Plant Cells via Microprojectile Bombardment," in *Plant Cell, Tissue, and Organ Culture: Fundamental Methods,* ed. Gamborg and Phillips (Springer-Verlag, Berlin); and McCabe et al. (1988) *Biotechnology* 6:923–926). Also see Weissinger et al. (1988) *Annual Rev. Genet.* 22:421–477; Sanford et al. (1987) *Particulate Science and Technology* 5:27–37 (onion); Christou et al. (1988) *Plant Physiol.* 87:671–674 (soybean); McCabe et al. (1988) *Bio/Technology* 6:923–926 (soybean); Finer and McMullen (1991) *In Vitro Cell Dev. Biol.* 27P:175–182 (soybean); Singh et al. (1998) *Theor. Appl. Genet.* 96:319–324 (soybean); Datta et al. (1990) *Biotechnology* 8:736–740 (rice); Klein et al. (1988) *Proc. Natl. Acad. Sci. U.S.A.* 85:4305–4309 (maize); Klein et al. (1988) *Biotechnology* 6:559–563 (maize); Tomes et al. "Direct DNA Transfer into Intact Plant Cells via Microprojectile Bombardment," in *Plant Cell, Tissue, and Organ Culture: Fundamental Methods,* ed. Gamborg (Springer-Verlag, Berlin) (1995) (maize); Klein et al. (1988) *Plant Physiol.* 91:440–444 (maize); Fromm et al. (1990) *Biotechnology* 8:833–839 (maize); Hooydaas-Van Slogteren and Hooykaas (1984) *Nature (London)* 311:763–764; Bytebier et al. (1987) *Proc. Natl. Acad. Sci. U.S.A.* 84:5345–5349 (Liliaceae); De Wet et al. (1985) in *The Experimental Manipulation of Ovule Tissues,* ed. Chapman et al. (Longman, New York), pp. 197–209 (pollen); Kaeppler et al. (1990) *Plant Cell Reports* 9:415–418; and Kaeppler et al. (1992) *Theor. Appl. Genet.* 84:560–566 (whisker-mediated transformation); D'Halluin et al. (1992) *Plant Cell* 4:1495–1505 (electroporation); Li et al. (1993) *Plant Cell Reports* 12:250–255 and Christou and Ford (1995) *Annals of Botany* 75:407–413 (rice); Osjoda et al. (1996) *Nature Biotechnology* 14:745–750 (maize via *Agrobacterium tumefaciens*); all of which are herein incorporated by reference. Thus, the invention provides a method for imparting insect resistance in *Agrobacterium tumefaciens*-susceptible plants in which the expression cassette is introduced into the cells by infecting the cells with *Agrobacterium tumefaciens,* a plasmid of which has been modified to include a plant expression cassette which expresses GPP- and/or a monoterpene synthase in the manner of this invention.

The modified plant may be grown into plants in accordance with conventional ways. See, for example, McCormick et al. (1986) *Plant Cell. Reports* 5:81–84. These plants may then be grown, and either pollinated with the same transformed strain or different strains, and the resulting plants or hybrid plants the desired phenotypic characteristic identified. Two or more generations may be grown to ensure that the subject phenotypic characteristic is stably maintained and inherited and then seeds harvested to ensure the desired phenotype or other property has been achieved.

In a preferred embodiment, the invention provides methods of imparting resistance to Diabrotica spp. to plants of a susceptible taxon, comprising the steps of:

(a) culturing cells or tissues from at least one plant from the taxon, (b) introducing into the cells of the cell or tissue culture at least one copy of an expression cassette comprising a structural gene coding for at least one monoterpene synthase or both a monoterpene synthase and GPP synthase, operably linked to a promoter that drives expression in a plant cell, and (c) regenerating whole plants from the cell or tissue culture with resistance to insects. Once whole plants have been obtained, they can be sexually or clonally reproduced in such manner that at least one copy of the sequence provided by the expression cassette is present in the cells of progeny of the reproduction.

Alternatively, once a single transformed plant has been obtained by the foregoing recombinant DNA method, conventional plant breeding methods can be used to transfer the structural gene or genes and associated regulatory sequences via crossing and backcrossing. Such intermediate methods will comprise the further steps of:

(a) sexually crossing the plant having resistance to insects with a plant from the taxon susceptible to insects;

(b) recovering reproductive material from the progeny of the cross; and (c) growing plants having resistance to insects from the reproductive material. Where desirable or necessary, the agronomic characteristics of the susceptible taxon can be substantially preserved by expanding this method to include the further steps of repetitively:

(a) backcrossing the progeny having resistance to insects with plants from taxon susceptible to insects; and (b) selecting for the expression of resistance to insects (or an associated marker gene) or monoterpene production among the progeny of the backcross, until the desired percentage of the characteristics of the susceptible taxon are present in the progeny along with the gene imparting resistance to insects.

Insect pests of harvested material, including those of stored grain, can also be targets for the methods of this invention. In view of this, the invention also provides methods for creating or enhancing resistance to insect pests in harvested materials and products obtained from harvested materials, by expressing at least one monotermene synthase and/or GPP synthase in the plant such that effective amounts of the desired monoterpene is produced in the harvested material and products obtained from such material.

The following examples are offered by way of illustration and not by way of limitation. The following description further exemplifies the compositions of this invention and the methods of making and using them. However, it will be understood that other methods, known by those of ordinary skill in the art to be equivalent, can also be employed.

EXAMPLES 1–6

Insect Larvae Inhibition and Toxicity Assays for Southern Corn Rootworm (SCR) and European Corn Borer (ECB)

Bioassay diets were prepared as described in Czapla and Lang in "Effect of Plant Lectins on the Larval Development of European Corn Borer (Lepidoptera: Pyralidae) and Southern Corn Rootworm (Coleoptera: Chrysomelidae)", *J. Econ. Entomol.* 83:2480–85 (1990), except that low melting temperature agarose replaced the regular agarose so that the diets could be chilled to 37° C. prior to the addition of limonene (one assay used the regular agarose diet).

Results were as follows. In Examples 1–4, the test larvae were Southern Corn Rootworm. In Examples 5–6, the test larvae were European Corn Borer. The results of each experiment represent the average from 16–32 insects. All limonene concentrations (ppm) are by weight. The SCR data indicate that limonene is effective against the larvae, but when limonene was used in the same protocol against ECB, little or no effect was seen.

$$\% \text{ Corrected Mortality} = 100 \times \left| \frac{\text{mortality of treated} - \text{control}}{100 - \text{control}} \right|$$

$$\% \text{ Wt. Reduction} = 100 \times \left| \frac{\text{control weight} - \text{treated weight}}{\text{control wt}} \right|$$

| Example: | 1 | | 2 | |
|---|---|---|---|---|
| Limonene ppm | % Corr. Mortal. | % weight Reduction | % Corr. Mortal. | % weight Reduction |
| 10,000 | 57 | 64 | 80 | 86 |
| 1,000 | 49 | 52 | 19 | 30 |
| 100 | 57 | 52 | 15 | 6 |

| Example: | 3 | | 4 | |
|---|---|---|---|---|
| Limonene ppm | % Corr. Mortal. | % weight Reduction | % Corr. Mortal. | % weight Reduction |
| 10,000 | 96 | 64 | 44 | 0 |
| 1,000 | 7 | 0 | 22 | 0 |
| 100 | 26 | 0 | 19 | 0 |

Average SCR Results:

| Limonene ppm | % Corr. Mortal. | % weight Reduction |
|---|---|---|
| 10,000 | 69 | 54 |
| 1,000 | 24 | 21 |
| 100 | 29 | 15 |

| Example: | 5 | | 6 | |
|---|---|---|---|---|
| Limonene ppm | % Corr. Mortal. | % weight Reduction | % Corr. Mortal. | % weight Reduction |
| 10,000 | 0 | 28 | 0 | 0 |
| 1,000 | 0 | 16 | 0 | 0 |
| 100 | 0 | 1 | 0 | 7 |

Average ECB Results:

| Limonene ppm | % Corr. Mortal. | % weight Reduction |
|---|---|---|
| 10,000 | 0 | 14 |
| 1,000 | 0 | 8 |
| 100 | 0 | 4 |

EXAMPLE 7

Maize callus cultures were transformed by microprojectile bombardment using plasmids containing a cloned gene coding for the limonene synthase (limonene cyclase) enzyme driven by a ubiquitin promoter and a ubiquitin intron and followed downstream by a PIN-II terminator. Whole, fertile plants were regenerated from the transformed callus and analyzed for limonene synthase and limonene. Representative results from one series were as follows:

$$\% \text{ Corrected Mortality} = 100 \times \left| \frac{\text{mortality of treated} - \text{control}}{100 - \text{control}} \right|$$

$$\% \text{ Wt. Reduction} = 100 \times \left| \frac{\text{control weight} - \text{treated weight}}{\text{control wt}} \right|$$

| Example: | 1 | | 2 | |
|---|---|---|---|---|
| Limonene ppm | % Corr. Mortal. | % weight Reduction | % Corr. Mortal. | % weight Reduction |
| 10,000 | 57 | 64 | 80 | 86 |
| 1,000 | 49 | 52 | 19 | 30 |
| 100 | 57 | 52 | 15 | 6 |

| Example: | 3 | | 4 | |
|---|---|---|---|---|
| Limonene ppm | % Corr. Mortal. | % weight Reduction | % Corr. Mortal. | % weight Reduction |
| 10,000 | 96 | 64 | 44 | 0 |
| 1,000 | 7 | 0 | 22 | 0 |
| 100 | 26 | 0 | 19 | 0 |

Average SCR Results:

| Limonene ppm | % Corr. Mortal. | % weight Reduction |
|---|---|---|
| 10,000 | 69 | 54 |
| 1,000 | 24 | 21 |
| 100 | 29 | 15 |

| Example: | 5 | | 6 | |
|---|---|---|---|---|
| Limonene ppm | % Corr. Mortal. | % weight Reduction | % Corr. Mortal. | % weight Reduction |
| 10,000 | 0 | 28 | 0 | 0 |
| 1,000 | 0 | 16 | 0 | 0 |
| 100 | 0 | 1 | 0 | 7 |

Average ECB Results:

| Limonene ppm | % Corr. Mortal. | % weight Reduction |
|---|---|---|
| 10,000 | 0 | 14 |
| 1,000 | 0 | 8 |
| 100 | 0 | 4 |

In other experiments, transgenic maize plants, and tissues that exhibited high expression of the limonene synthase protein were produced. The enzyme was extracted from transformed plants and tissues and allowed to react with tritium-labeled geranyl pyrophosphate (GPP). The extracted enzyme converted GPP to limonene, showing that a functional enzyme was being produced. In addition, western blots were done and confirmed the presence of LS protein in transgenic tissues but not in negative control tissues. Seed was collected from the transformed plants. In sum, whole fertile, transformed plants have been produced that express active limonene cyclase (synthase) according to the teaching of the above-identified application.

Western blots were also performed on chloroplasts isolated from plants grown from T1 and T2 seed which expressed the mint limonene synthase gene (FIG. 6, SEQ ID NO:1) in leaf tissue. Thus, the mint limonene synthase was properly targeted to maize plastids and the protein was processed to the correct size, indicating that the mint limonene synthase plastid targeting sequence can be used to target proteins to maize plastids.

EXAMPLE 8

In view of the results set forth in Example 7, demonstrating expression of active limonene synthase in whole, fertile, transformed plants, larvicidally effective amounts of limonene can be produced in such transgenic plants where sufficient substrate is present for the limonene synthase enzyme to act on. Accordingly, maize callus cultures are transformed by art recognized microprojectile bombardment methods using plasmids containing genes coding for both the limonene synthase enzyme and the GPP synthase enzyme, driven, for example, by one or more promoters (a ubiquitin promoter, for example) and followed downstream by, for example, a PIN-II terminator. Whole, fertile plants are regenerated from the transformed callus and analyzed for presence of and/or activity of both enzymes, and are also analyzed for the presence of limonene.

Alternatively, callus is generated from transgenic plants that contain and express the limonene synthase transgene, and such callus cultures are transformed as described above, except that such callus is transformed using plasmids containing a gene coding for the GPP synthase protein. The whole, fertile, transgenic plants regenerated from such transformed callus produce larvicidally effective amounts of limonene.

EXAMPLE 9

Average minimum levels of various monoterpenes required for 100% mortality of Western corn rootworm were determined by the methods described in Examples 1–6 as follows:

Limonene—200 ppm

S-linalool—50 ppm carveol—25 ppm

EXAMPLE 10

Construction of Expression Vectors

Figure 2:
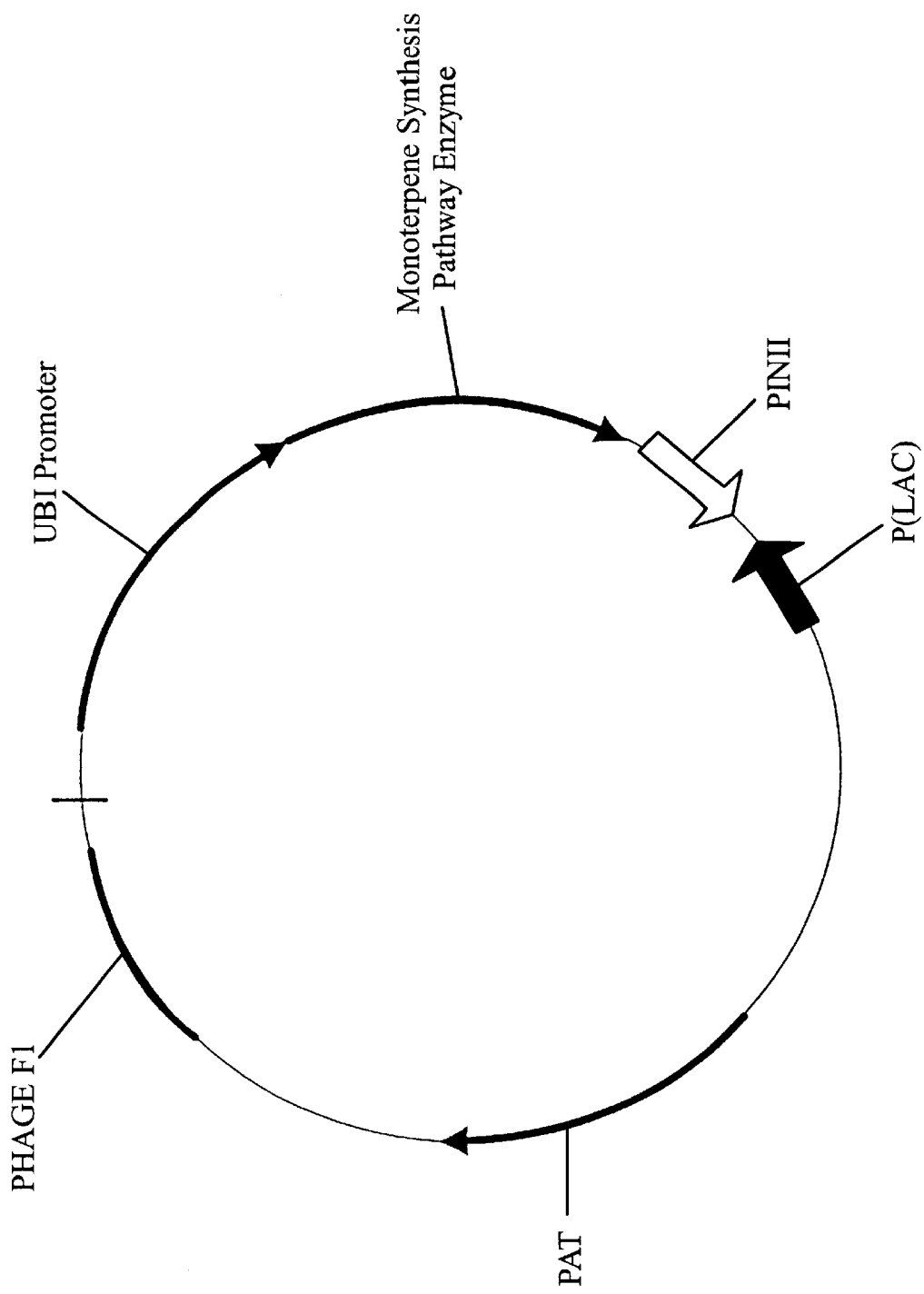
FIG. 2 schematically illustrates the plasmid construct comprising the ubiquitin promoter and a monoterpene synthesis pathway enzyme.

Nucleotide sequences encoding GPP-, limonene, carveol and S-linalool synthase, as set forth in FIGS. 6, 8, 10 and 12 respectively, are cloned into a plasmid vector, such as that shown in FIG. 2, in the sense orientation so that they are under the transcriptional control of the ubiquitin promoter. A selectable marker gene may reside on this plasmid or may be introduced as part of a second plasmid. The transformation construct is then available for introduction into maize embryos by bombardment methods as described in Example 12.

EXAMPLE 11

Construction of Expression Vectors

Figure 3:
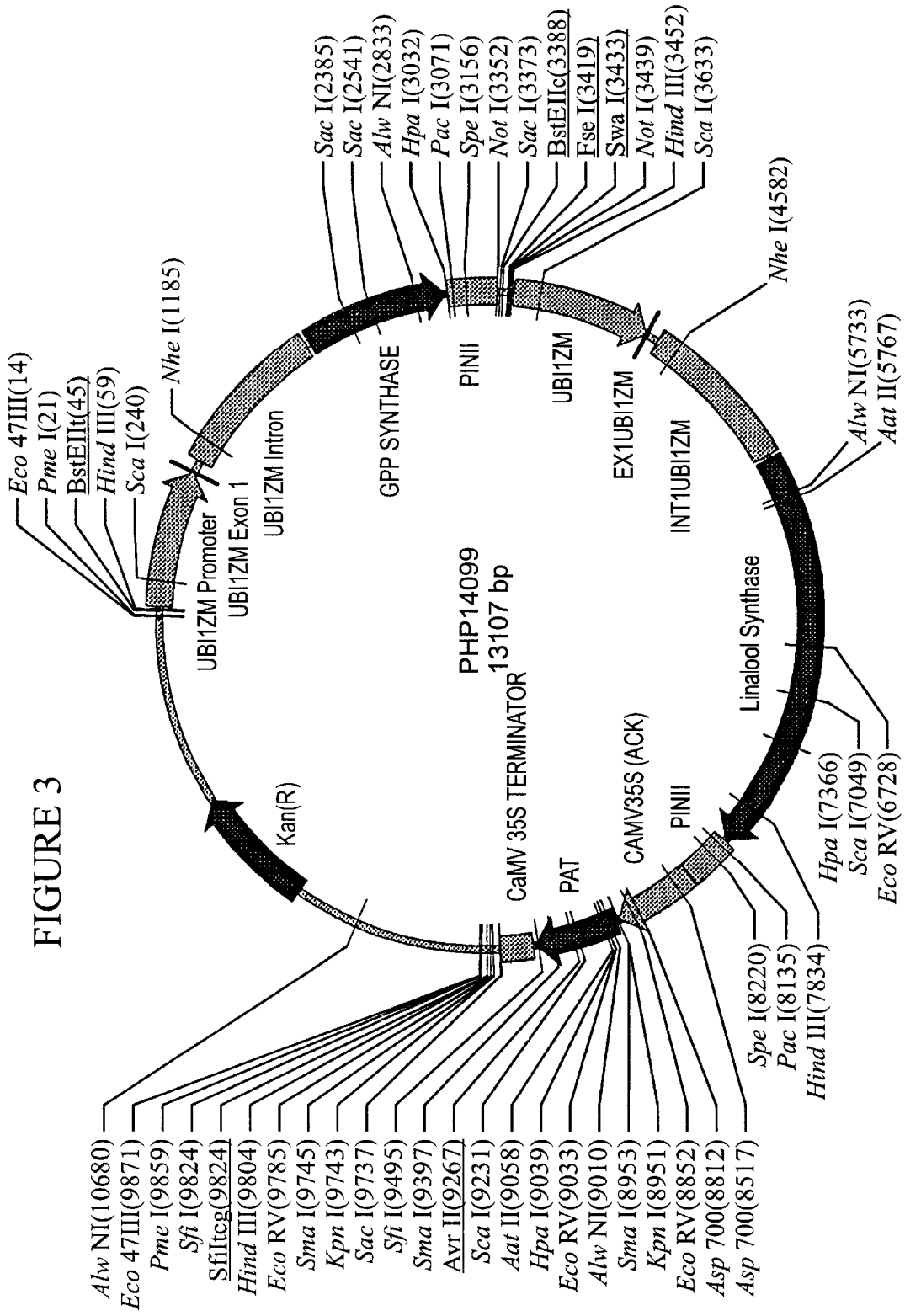
FIG. 3 schematically illustrates the plasmid construct PHP14099 for expression of GPP- and S-linalool synthases, and production of S-linalool in plants.

Nucleotide sequences encoding GPP- and S-linalool synthase as described in EXAMPLE 10 were cloned in the sense orientation into an expression vector as shown in in FIG. 3(PHP14099); such that both coding sequences are under the transcriptional control of the ubiquitin promoter. The plasmid contains the selectable marker gene PAT.

Figure 4:
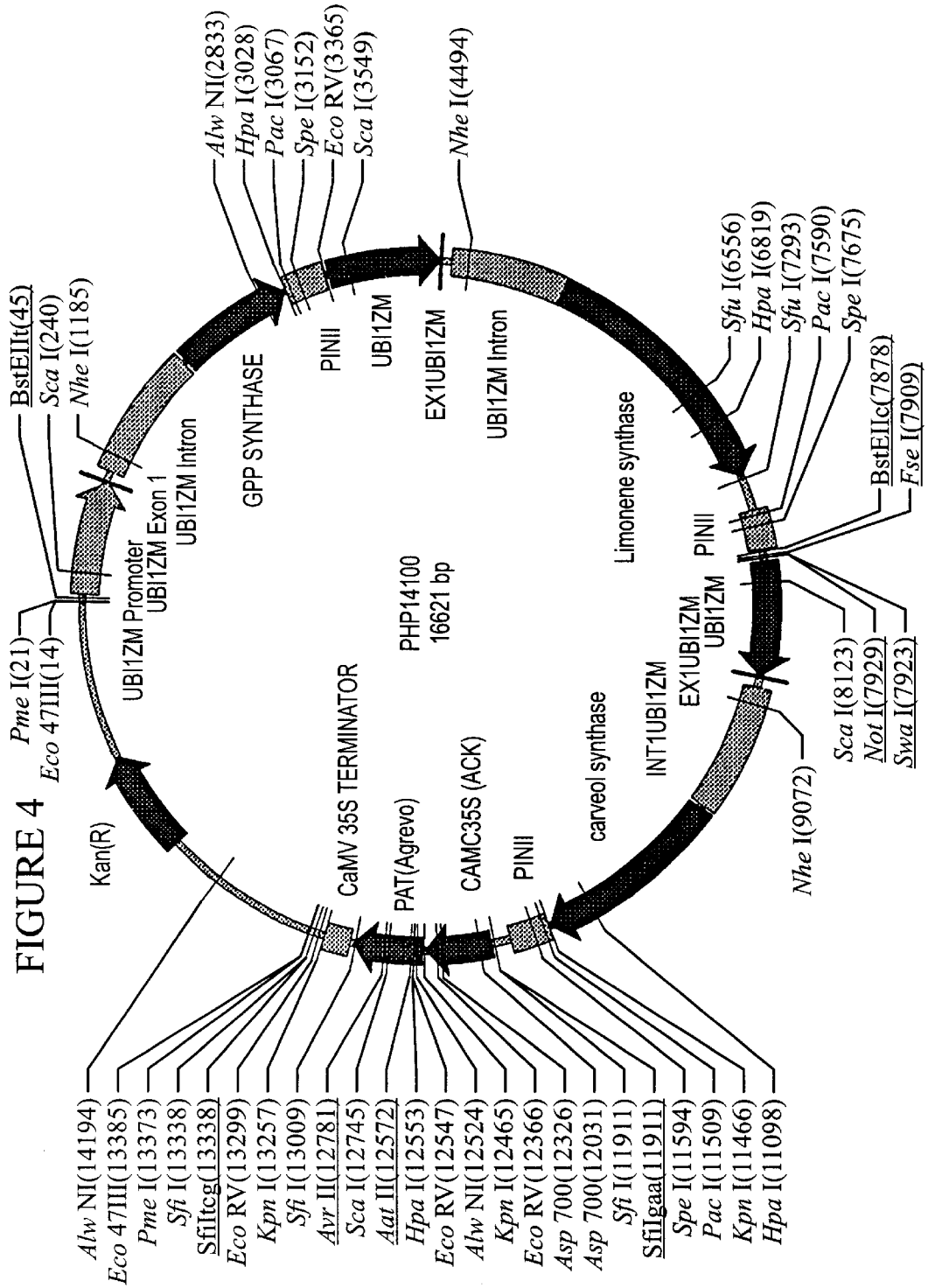
FIG. 4 schematically illustrates the plasmid construct PHP114100 for expression of GPP-, limonene- and carveol synthases; and production of limonene and carveol.

Nucleotide sequences encoding GPP-, limonene- and carveol synthases as described in EXAMPLE 10 were cloned in the sense orientation into an expression vector as shown in FIG. 4(PHP14100); such that all three coding sequences are under the transcriptional control of the ubiquitin promoter. The plasmid contains the selectable marker gene PAT.

The transformation constructs PHP14099 and PHP14100 are available for introduction into maize embryos by bombardment methods as described in Example 12.

EXAMPLE 12

Transformation and Regeneration of Maize Callus

Immature maize embryos from greenhouse donor plants are bombarded with a plasmid containing the disclosed GPP- or monoterpene synthase gene operably linked to the ubiquitin promoter plus a plasmid containing the selectable marker gene PAT (Wohlleben et al. (1988) *Gene* 70:25–37) that confers resistance to the herbicide Bialophos. Transformation is performed as follows. All media recipes are in the Appendix.

Preparation of Target Tissue

The ears are surface sterilized in 30% Chlorox bleach plus 0.5% Micro detergent for 20 minutes, and rinsed two times with sterile water. The immature embryos are excised and placed embryo axis side down (scutellum side up), 25 embryos per plate. These are cultured on 560 L medium for 4 days prior to bombardment, in the dark. The day of bombardment, the embryos are transferred to 560 Y medium for 4 hours, arranged within the 2.5-cm target zone.

Preparation of DNA

A plasmid vector comprising the disclosed GPP- or monoterpene synthase operably linked to the ubiquitin promoter is constructed. This plasmid DNA plus plasmid DNA containing a PAT selectable marker is precipitated onto 1.1 µm (average diameter) tungsten pellets using a $CaCl_2$ precipitation procedure as follows:

100 µl prepared tungsten particles in water
  10 µl (1 µg) DNA in TrisEDTA buffer (1 µg total)
  100 µl 2.5 M $CaCl_2$
  10 µl 0.1 M spermidine Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 µl 100% ethanol is added to the final tungsten particle pellet. For particle gun bombardment, the tungsten/DNA particles are briefly sonicated and 10 µl spotted onto the center of each macrocarrier and allowed to dry about 2 minutes before bombardment.

Particle Gun Treatment

The sample plates are bombarded at level #4 in particle gun #HE34-1 or #HE34-2. All samples receive a single shot at 650 PSI, with a total of ten aliquots taken from each tube of prepared particles/DNA.

Subsequent Treatment

Following bombardment, the embryos are kept on 560Y medium for 2 days, then transferred to 560R selection medium containing 3 mg/liter Bialophos, and subcultured every 2 weeks. After approximately 10 weeks of selection, selection-resistant callus clones are sampled for PCR and activity of the acetyl-CoA synthetase gene of interest. Positive lines are transferred to 288J medium to initiate plant regeneration. Following somatic embryo maturation (2–4 weeks), well-developed somatic embryos are transferred to medium for germination and transferred to the lighted culture room. Approximately 7–10 days later, developing plantlets are transferred to medium in tubes for 7–10 days until plantlets are well established. Plants are then transferred to inserts in flats (equivalent to 2.5" pot) containing potting soil and grown for 1 week in a growth chamber, subsequently grown an additional 1–2 weeks in the greenhouse, then transferred to classic 600 pots (1.6 gallon) and grown to maturity. Plants are monitored for expression of the GPP-synthase or monoterpene synthase gene of interest.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

-40-

APPENDIX

| Ingredient | Amount | Unit |
|---|---|---|
| D-I H$_2$O | 900.000 | ml |
| CHU (N6) Basal Salts (SIGMA C-1416) | 1.600 | g |
| N6 Macronutrients 10X Stock ## | 60.000 | ml |
| Potassium Nitrate | 1.680 | g |
| B5H Minor Salts 1000X ### | 0.600 | ml |
| B5H Fe Na EDTA 100X #### | 6.000 | ml |
| Eriksson's Vitamin Mix (1000X SIGMA-1511) | 0.400 | ml |
| S & H Vitamin Mixture 100X Stock (S3766) | 6.000 | ml |
| Thiamine.HCL 0.4mg/ml | 0.500 | ml |
| L-Proline | 1.980 | g |
| Casein Hydrolystate (acid) | 0.300 | g |
| Sucrose | 20.000 | g |
| Glucose | 0.600 | g |
| 2,4-D 0.5 mg/ml | 1.600 | ml |
| Gelrite @ | 2.000 | g |
| Dicamba 1 mg/ml # | 1.200 | ml |
| Silver Nitrate 2 mg/ml # | 1.700 | ml |

Directions:

@ = Add after bringing up to volume

# = Add after sterilizing and cooling to temp.

-41-

Dissolve ingredients in polished D-I H₂O in sequence
Adjust to pH 5.8
Bring up to volume with polished D-I H₂O after adjusting pH
Sterilize and cool to 60°C.

5  ## = Dissolve 1.660 g of Calcium Chloride Dihydrate in 950.000 ml of polished D-I H₂O. Then dissolve 4.629 of Ammonium Sulfate; 4.000 g of Potassium Phosphate Monobasic $KH_2PO_4$; 1.850 g of Magnesium Sulfate 7-H₂O, $MgSO_4$, 7H₂O; and 28.300 g of Potassium Nitrate into sequence. Bring up to volume with polished D-I H₂O.

10  ### = Dissolve 3.000 g of Boric Acid; 10.000 g of Manganous Sulfate Monohydrate; 0.250 g of Sodium Molybdate Dihydrate; and 0.750 g of Potassium Iodide in polished D-I H₂O in sequence. Bring up to volume with polished D-I H₂O.

#### = Dissolve 3.700 g of Disodium EDTA Dihydrate and 2.790 g of Ferrous
15  Sulfate 7-Hydrate into D-I H₂O. Bring up to volume with D-I H₂O.
Total Volume (L) = 1.00

-42-

604 A

| Ingredient | Amount | Unit |
|---|---|---|
| D-I $H_2O$ | 900.000 | ml |
| CHU (N6) Basal Salts (SIGMA C-1416) | 1.600 | g |
| N6 Macronutrients 10X Stock ## | 60.000 | ml |
| Potassium Nitrate | 1.680 | g |
| B5H Minor Salts 1000X ### | 0.600 | ml |
| B5H Fe Na EDTA 100X #### | 6.000 | ml |
| Eriksson's Vitamin Mix (1000X SIGMA-1511) | 0.400 | ml |
| S & H Vitamin Mixture 100X Stock (S3766) | 6.000 | ml |
| Thiamine.HCL 0.4mg/ml | 0.500 | ml |
| L-Proline | 1.980 | g |
| Casein Hydrolysate (acid) | 0.300 | g |
| Sucrose | 20.000 | g |
| Glucose | 0.600 | g |
| 2, 4-D 0.5mg/ml | 1.600 | ml |
| Gelrite @ | 2.000 | g |
| Dicamba 1mg/ml # | 1.200 | ml |
| Silver Nitrate 2mg/ml # | 1.700 | ml |
| Bialaphos 1 mg/ml # | 3.000 | ml |

-43-

Directions:

@ = Add after bringing up to volume

# = Add after sterilizing and cooling to temp.

Dissolve ingredients in polished D-I $H_2O$ in sequence

Adjust to pH 5.8

Bring up to volume with polished D-I $H_2O$ after adjusting pH

Sterilize and cool to 60°C.

= Dissolve 1.660 g of Calcium Chloride Dihydrate in 950.000 ml of polished D-I $H_2O$. Then dissolve 4.629 of Ammonium Sulfate; 4.000 g of Potassium Phosphate Monobasic $KH_2PO_4$; 1.850 g of Magnesium Sulfate 7-$H_2O$, $MgSO_4$, 7$H_2O$; and 28.300 g of Potassium Nitrate into sequence. Bring up to volume with polished D-I $H_2O$.

= Dissolve 3.000 g of Boric Acid; 10.000 g of Manganous Sulfate Monohydrate; 0.250 g of Sodium Molybdate Dihydrate; and 0.750 g of Potassium Iodide in polished D-I $H_2O$ in sequence. Bring up to volume with polished D-I $H_2O$.

#### = Dissolve 3.700 g of Disodium EDTA Dihydrate and 2.790 g of Ferrous Sulfate 7-Hydrate into D-I $H_2O$. Bring up to volume with D-I $H_2O$.

Total Volume (L) = 1.00

-44-

605 J

| Ingredient | Amount | Unit |
|---|---|---|
| D-I $H_2O$ | 900.000 | ml |
| CHU (N6) Basal Salts (SIGMA C-1416) | 1.600 | g |
| N6 Macronutrients 10X Stock ## | 60.000 | ml |
| Potassium Nitrate | 1.680 | g |
| B5H Minor Salts 1000X ### | 0.600 | ml |
| B5H Fe Na EDTA 100X #### | 6.000 | ml |
| Eriksson's Vitamin Mix (1000X SIGMA-1511) | 0.400 | ml |
| S & H Vitamin Mixture 100X Stock (S3766) | 6.000 | ml |
| Thiamine.HCL 0.4mg/ml | 0.500 | ml |
| Sucrose | 20.000 | g |
| Glucose | 0.600 | g |
| 2, 4-D 0.5mg/ml | 1.600 | ml |
| Gelrite @ | 2.000 | g |
| Dicamba 1mg/ml # | 1.200 | ml |
| Silver Nitrate 2mg/ml # | 0.425 | ml |
| Bialaphos 1 mg/ml # | 3.000 | ml |

Directions:

@ = Add after bringing up to volume

# = Add after sterilizing and cooling to temp.

Dissolve ingredients in polished D-I $H_2O$ in sequence

Adjust to pH 5.8

Bring up to volume with polished D-I $H_2O$ after adjusting pH
Sterilize and cool to 60°C.
= Dissolve 1.660 g of Calcium Chloride Dihydrate in 950.000 ml of polished D-I $H_2O$. Then dissolve 4.629 of Ammonium Sulfate; 4.000 g of Potassium Phosphate Monobasic $KH_2PO_4$; 1.850 g of Magnesium Sulfate 7-$H_2O$, $MgSO_4$, 7$H_2O$; and 28.300 g of Potassium Nitrate into sequence. Bring up to volume with polished D-I $H_2O$.
= Dissolve 3.000 g of Boric Acid; 10.000 g of Manganous Sulfate Monohydrate; 0.250 g of Sodium Molybdate Dihydrate; and 0.750 g of Potassium Iodide in polished D-I $H_2O$ in sequence. Bring up to volume with polished D-I $H_2O$.
#### = Dissolve 3.700 g of Disodium EDTA Dihydrate and 2.790 g of Ferrous Sulfate 7-Hydrate into D-I $H_2O$. Bring up to volume with D-I $H_2O$.
Total Volume (L) = 1.00

604 S

| Ingredient | Amount | Unit |
|---|---|---|
| D-I $H_2O$ | 800.000 | ml |
| CHU (N6) Basal Salts (SIGMA C-1416) | 1.600 | g |
| N6 Macronutrients 10X Stock ## | 60.000 | ml |
| Potassium Nitrate | 1.680 | g |
| B5H Minor Salts 1000X ### | 0.600 | ml |
| B5H Fe Na EDTA 100X #### | 6.000 | ml |
| Eriksson's Vitamin Mix (1000X SIGMA-1511) | 0.400 | ml |
| S & H Vitamin Mixture 100X Stock (S3766) | 6.000 | ml |
| Thiamine.HCL 0.4mg/ml | 0.500 | ml |
| L-Proline | 1.980 | g |
| Casein Hydrolysate (acid) | 0.300 | g |
| Sucrose | 120.000 | g |
| Glucose | 0.600 | g |
| 2, 4-D 0.5mg/ml | 1.600 | ml |
| Gelrite @ | 2.000 | g |
| Dicamba 1mg/ml # | 1.200 | ml |
| Silver Nitrate 2mg/ml # | 1.700 | ml |

Directions:

@ = Add after bringing up to volume

# = Add after sterilizing and cooling to temp.

Dissolve ingredients in polished D-I $H_2O$ in sequence

-47-

Adjust to pH 5.8
Bring up to volume with polished D-I H$_2$O after adjusting pH
Sterilize and cool to 60°C.
= Dissolve 1.660 g of Calcium Chloride Dihydrate in 950.000 ml of polished D-I H$_2$O. Then dissolve 4.629 of Ammonium Sulfate; 4.000 g of Potassium Phosphate Monobasic KH$_2$PO$_4$; 1.850 g of Magnesium Sulfate 7-H$_2$O, MgSO$_4$, 7H$_2$O; and 28.300 g of Potassium Nitrate into sequence. Bring up to volume with polished D-I H$_2$O.
= Dissolve 3.000 g of Boric Acid; 10.000 g of Manganous Sulfate Monohydrate; 0.250 g of Sodium Molybdate Dihydrate; and 0.750 g of Potassium Iodide in 950.000 ml of polished D-I H$_2$O in sequence. Bring up to volume with polished D-I H$_2$O.
#### = Dissolve 3.700 g of Disodium EDTA Dihydrate and 2.790 g of Ferrous Sulfate 7-Hydrate into 950.000 ml of D-I H$_2$O. Bring up to volume with D-I H$_2$O.
Total Volume (L) = 1.00

-48-

272 V

| Ingredient | Amount | Unit |
|---|---|---|
| D-I $H_2O$ | 950.000 | ml |
| MS Salts (GIBCO 11117-074) | 4.300 | g |
| Myo-Inositol | 0.100 | g |
| MS Vitamins Stock Solution ## | 5.000 | ml |
| Sucrose | 40.000 | g |
| Bacto-Agar @ | 6.000 | g |

Directions:

@ = Add after bringing up to volume

Dissolve ingredients in polished D-I $H_2O$ in sequence

Adjust to pH 5.6

Bring up to volume with polished D-I $H_2O$ after adjusting pH

Sterilize and cool to 60°C.

## = Dissolve 0.100 g of Nicotinic Acid; 0.020 g of Thiamine.HCL; 0.100 g of Pyridoxine.HCL; and 0.400 g of Glycine in 875.00 ml of polished D-I $H_2O$ in sequence. Bring up to volume with polished D-I $H_2O$. Make in 400 ml portions. Thiamine.HCL & Pyridoxine.HCL are in Dark Desiccator. Store for one month, unless contamination or precipitation occur, then make fresh stock.

Total Volume (L) = 1.00

-49-

288 J

| Ingredient | Amount | Unit |
|---|---|---|
| D-I H$_2$O | 950.000 | ml |
| MS Salts | 4.300 | g |
| Myo-Inositol | 0.100 | g |
| MS Vitamins Stock Solution ## | 5.000 | ml |
| Zeatin .5mg/ml | 1.000 | ml |
| Sucrose | 60.000 | g |
| Gelrite @ | 3.000 | g |
| Indole Acetic Acid 0.5 mg/ml # | 2.000 | ml |
| .1mM Absissic Acid | 1.000 | ml |
| Bialaphos 1mg/ml # | 3.000 | ml |

Directions:

@ = Add after bringing up to volume

Dissolve ingredients in polished D-I H$_2$O in sequence

Adjust to pH 5.6

Bring up to volume with polished D-I H$_2$O after adjusting pH

Sterilize and cool to 60°C.

Add 3.5g/L of Gelrite for cell biology.

## = Dissolve 0.100 g of Nicotinic Acid; 0.020 g of Thiamine.HCL; 0.100 g of Pyridoxine.HCL; and 0.400 g of Glycine in 875.00 ml of polished D-I H$_2$O in sequence. Bring up to volume with polished D-I H$_2$O. Make in 400 ml portions. Thiamine.HCL & Pyridoxine.HCL are in Dark Desiccator. Store for one month, unless contamination or precipitation occur, then make fresh stock.

Total Volume (L) = 1.00

-50-

560 L

| Ingredient | Amount | Unit |
|---|---|---|
| D-I Water, Filtered | 950.000 | ml |
| CHU (N6) Basal Salts (SIGMA C-1416) | 4.000 | g |
| Eriksson's Vitamin Mix (1000X SIGMA-1511 | 0.400 | ml |
| Thiamine.HCL 0.4mg/ml | 1.250 | ml |
| Sucrose | 20.000 | g |
| 2, 4-D 0.5mg/ml | 2.000 | ml |
| L-Proline | 2.880 | g |
| Gelrite @ | 2.000 | g |
| Silver Nitrate 2mg/ml # | 4.250 | ml |

Directions:
@ = Add after bringing up to volume
# = Add after sterilizing and cooling to temp.
Dissolve ingredients in D-I $H_2O$ in sequence
Adjust to pH 5.8 with KOH
Bring up to volume with D-I $H_2O$
Sterilize and cool to room temp.
Total Volume (L) = 1.00

-51-

560 R

| Ingredient | Amount | Unit |
|---|---|---|
| D-I Water, Filtered | 950.000 | ml |
| CHU (N6) Basal Salts (SIGMA C-1416) | 4.000 | g |
| Eriksson's Vitamin Mix (1000X SIGMA-1511 | 1.000 | ml |
| Thiamine.HCL 0.4mg/ml | 1.250 | ml |
| Sucrose | 30.000 | g |
| 2, 4-D 0.5mg/ml | 4.000 | ml |
| Gelrite @ | 3.000 | g |
| Silver Nitrate 2mg/ml # | 0.425 | ml |
| Bialaphos 1mg/ml # | 3.000 | ml |

Directions:

@ = Add after bringing up to volume
# = Add after sterilizing and cooling to temp.
Dissolve ingredients in D-I $H_2O$ in sequence
Adjust to pH 5.8 with KOH
Bring up to volume with D-I $H_2O$
Sterilize and cool to room temp.
Total Volume (L) = 1.00

-52-

560 Y

| Ingredient | Amount | Unit |
|---|---|---|
| D-I Water, Filtered | 950.000 | ml |
| CHU (N6) Basal Salts (SIGMA C-1416) | 4.000 | g |
| Eriksson's Vitamin Mix (1000X SIGMA-1511 | 1.000 | ml |
| Thiamine.HCL 0.4mg/ml | 1.250 | ml |
| Sucrose | 120.000 | g |
| 2,4-D 0.5mg/ml | 2.000 | ml |
| L-Proline | 2.880 | g |
| Gelrite @ | 2.000 | g |
| Silver Nitrate 2mg/ml # | 4.250 | ml |

Directions:

@ = Add after bringing up to volume

\# = Add after sterilizing and cooling to temp.

Dissolve ingredients in D-I $H_2O$ in sequence

Adjust to pH 5.8 with KOH

Bring up to volume with D-I $H_2O$

Sterilize and cool to room temp.

\*\* Autoclave less time because of increased sucrose\*\*

Total Volume (L) = 1.00

That which is claimed:

1. A method for manipulating a metabolic pathway in a plant cell, said method comprising transforming a plant cell with at least one nucleotide sequence operably linked to a promoter that drives expression in a plant cell, wherein said nucleotide sequence is an antisense nucleotide sequence comprising a nucleotide sequence encoding a monoterpene synthesis pathway enzyme, said nucleotide sequence being in antisense orientation with respect to said promoter, said antisense nucleotide sequence selected from the group consisting of:
   a) an antisense nucleotide sequence for a nucleotide sequence encoding a limonene synthase protein having the amino acid sequence set forth in SEQ ID NO:2;
   b) an antisense nucleotide sequence for a nucleotide sequence encoding a carveol synthase protein having the amino acid sequence set forth in SEQ ID NO:6;
   c) an antisense nucleotide sequence for a nucleotide sequence encoding a S-linalool synthase protein having the amino acid sequence set forth in SEQ ID NO:8;
   d) an antisense nucleotide sequence for a nucleotide sequence encoding a limonene synthase protein as set forth in SEQ ID NO: 1;
   e) an antisense nucleotide sequence for a nucleotide sequence encoding a carveol synthase protein as set forth in SEQ ID NO:5; and
   f) an antisense nucleotide sequence for a nucleotide sequence encoding a S-linalool synthase protein as set forth in SEQ ID NO:7.

2. The method of claim 1 wherein said plant cell is monocotyledonous.

3. The method of claim 2 wherein said monocot cell is a corn, wheat, rice, oat, rye or sorghum cell.

4. The method of claim 1 wherein said promoter is a constitutive promoter.

5. The method of claim 4 wherein said constitutive promoter is a ubiquitin promoter.

6. The method of claim 1 wherein said promoter is a tissue-specific promoter.

7. The method of claim 6 wherein said tissue-specific promoter is a root-specific promoter.

8. A method for manipulating a metabolic pathway in a plant cell, said method comprising transforming a plant cell with a first nucleotide sequence encoding a GPP synthase protein having the amino acid sequence set forth in SEQ ID NO:4, and at least one additional nucleotide sequence which is selected from the group consisting of:
   a) a nucleotide sequence encoding a limonene synthase protein having the amino acid sequence set forth in SEQ ID NO:2;
   b) a nucleotide sequence encoding a carveol synthase protein having the amino acid sequence set forth in SEQ ID NO:6;
   c) a nucleotide sequence encoding a S-linalool synthase protein having the amino acid sequence set forth in SEQ ID NO:8;
   d) a nucleotide sequence encoding a limonene synthase protein as set forth in SEQ ID NO: 1;
   e) a nucleotide sequence encoding a carveol synthase protein as set forth in SEQ ID NO:5; and
   f) a nucleotide sequence encoding a S-linalool synthase protein as set forth in SEQ ID NO:7;

wherein said first and said additional nucleotide sequence are operably linked to a promoter that drives expression in a plant cell.

9. The method of claim 8, wherein said plant cell is co-transformed.

10. A method for creating or enhancing resistance to Diabrotica spp. in a plant, said method comprising manipulating a metabolic pathway in a plant cell according to the method of claim 8, wherein said selected nucleotide sequence consists of a second nucleotide sequence encoding a limonene synthase protein, and further comprising regenerating stably transformed plants producing effective amounts of limonene.

11. A method for creating or enhancing resistance to Diabrotica spp. in a plant, said method comprising manipulating a metabolic pathway in a plant cell according to the method of claim 8, wherein said selected nucleotide sequences consist of a second nucleotide sequence encoding a limonene synthase protein and a third nucleotide sequence encoding a carveol synthase protein; and further comprising regenerating stably transformed plants producing effective amounts of carveol.

12. A method for creating or enhancing resistance to Diabrotica spp. in a plant, said method comprising manipulating a metabolic pathway in a plant cell according to the method of claim 8, wherein said selected nucleotide sequence consists of a second nucleotide sequence encoding a S-linalool synthase protein, and further comprising regenerating stably transformed plants producing effective amounts of S-linalool.

13. The method of any of the claims 10, 11, or 12 wherein said plant is monocotyledonous.

14. The method of claim 13 wherein said monocot plant is a corn plant (Z. mays L.).

15. The method of claim 8, wherein said first nucleotide sequence has the nucleotide sequence set forth in SEQ ID NO:3.

16. A method of producing limonene synthase and GPP synthase in a plant cell, said method comprising:

transforming a first plant cell with a nucleotide sequence encoding a limonene synthase protein operably linked to a promoter that drives expression in a plant cell wherein said limonene synthase protein has the amino acid sequence set forth in SEQ ID NO:2;

transforming a second plant cell with a nucleotide sequence encoding a GPP synthase protein operably linked to a promoter that drives expression in a plant cell wherein said GPP synthase protein has the amino acid sequence set forth in SEQ ID NO:4, regenerating a first fertile transgenic plant from said first plant cell, regenerating a second fertile transgenic plant from said second plant cell, crossing said first and second fertile transgenic plants; and recovering progeny from said cross which express limonene synthase and GPP synthase.

17. A method of producing limonene synthase, GPP synthase, and carveol synthase in a plant cell, said method comprising:

transforming a first plant cell with a nucleotide sequence encoding a limonene synthase protein operably linked to a promoter that drives expression in a plant cell wherein said limonene synthase protein has the amino acid sequence set forth in SEQ ID NO:2;

transforming a second plant cell with a nucleotide sequence encoding a GPP synthase protein operably linked to a promoter that drives expression in a plant cell wherein said GPP synthase protein has the amino acid sequence set forth in SEQ ID NO:4;

transforming a third plant cell with a nucleotide sequence encoding a carveol synthase protein operably linked to a promoter that drives expression in a plant cell wherein said carveol synthase protein has the amino acid sequence set forth in SEQ ID NO:6;

producing a first fertile transgenic plant from said first plant cell;

producing a second fertile transgenic plant from said second plant cell;

producing a third fertile transgenic plant from said third plant cell;

performing a first cross between said first and second fertile transgenic plants;

recovering progeny from said first cross;

performing a second cross between said third fertile transgenic plant and said progeny of said first cross; and recovering progeny from said second cross which express limonene synthase, GPP synthase and carveol synthase.

18. The method of claim 17, wherein said second plant cell is transformed with a nucleotide sequence set forth in SEQ ID NO:5, and said third plant cell is transformed with a nucleotide sequence set forth in SEQ ID NO:3.

19. A method of producing GPP synthase and S-linalool synthase in a plant cell, said method comprising:

transforming a first plant cell with a nucleotide sequence encoding a GPP synthase protein operably linked to a promoter that drives expression in a plant cell wherein said GPP synthase protein has the amino acid sequence set forth in SEQ ID NO:4;

transforming a second plant cell with a nucleotide sequence encoding a S-linalool synthase protein operably linked to a promoter that drives expression in a plant cell wherein said S-linalool synthase protein has the amino acid sequence set forth in SEQ ID NO: 8;

producing a first fertile transgenic plant from said first plant cell;

producing a second fertile transgenic plant from said second plant cell;

crossing said first and second fertile transgenic plants; and recovering progeny from said cross which express GPP synthase and S-linalool synthase.

20. A transformed plant cell having a manipulated metabolic pathway by having stably incorporated into its genome a first nucleotide sequence encoding a GPP synthase having the amino acid sequence set forth in SEQ ID NO:4 and at least one additional nucleotide sequence selected from the group consisting of:

a) a nucleotide sequence encoding a limonene synthase protein having the amino acid sequence set forth in SEQ ID NO:2;

b) a nucleotide sequence encoding a carveol synthase protein having the amino acid sequence set forth in SEQ ID NO:6;

c) a nucleotide sequence encoding a S-linalool synthase protein having the amino acid sequence set forth in SEQ ID NO:8;

d) a nucleotide sequence encoding a limonene synthase protein as set forth in SEQ ID NO:1;

e) a nucleotide sequence encoding a carveol synthase protein as set forth in SEQ ID NO:5; and f) a nucleotide sequence encoding a S-linalool synthase protein as set forth in SEQ ID NO:7;

wherein said first and said additional nucleotide sequence are operably linked to a promoter that drives expression in a plant.

21. A transformed plant having a manipulated metabolic pathway by having stably incorporated into its genome a first nucleotide sequence encoding a GPP synthase having the amino acid sequence set forth in SEQ ID NO:4 and at least one additional nucleotide sequence selected from the group consisting of:

a) a nucleotide sequence encoding a limonene synthase protein having the amino acid sequence set forth in SEQ ID NO:2;

b) a nucleotide sequence encoding a carveol synthase protein having the amino acid sequence set forth in SEQ ID NO:6;

c) a nucleotide sequence encoding a S-linalool synthase protein having the amino acid sequence set forth in SEQ ID NO:8;

d) a nucleotide sequence encoding a limonene synthase protein as set forth in SEQ ID NO:1;

e) a nucleotide sequence encoding a carveol synthase protein as set forth in SEQ ID NO:5; and f) a nucleotide sequence encoding a S-linalool synthase protein as set forth in SEQ ID NO:7;

wherein said first and said additional nucleotide sequence are operably linked to a promoter that drives expression in a plant.

22. The plant of claim 21 wherein said plant is monocotyledonous.

23. The plant of claim 22 wherein said monocot plant is a corn, wheat, rice, oat, rye or sorghum plant.

24. The plant of claim 21 wherein said promoter is a constitutive promoter.

25. The plant of claim 24 wherein said constitutive promoter is a ubiquitin promoter.

26. The plant of claim 21 wherein said promoter is a tissue-specific promoter.

27. The plant of claim 26 wherein said tissue-specific promoter is a root-specific promoter.

28. The plant of any one of claims 24–27 wherein said plant is a dicot.

29. Seed of the plant of any one of claims 21–27.

30. Seed of the plant of claim 28.

31. A method for manipulating a metabolic pathway in a plant cell, said method comprising transforming a plant cell with a first nucleotide sequence encoding a protein having GPP synthase activity that has an amino acid sequence which is at least 80% identical to the amino acid sequence set forth in SEQ ID NO:4, and at least one additional nucleotide sequence which is selected from the group consisting of:

a) a nucleotide sequence encoding a protein having limonene synthase activity that has an amino acid sequence which is at least 80% identical to the amino acid sequence set forth in SEQ ID NO:2;

b) a nucleotide sequence encoding a protein having carveol synthase activity that has an amino acid sequence which is at least 80% identical to the amino acid sequence set forth in SEQ ID NO:6; and c) a nucleotide sequence encoding a protein having S-linalool synthase activity that has an amino acid sequence which is at least 80% identical to the amino acid sequence set forth in SEQ ID NO:8;

wherein said first and said additional nucleotide sequence are operably linked to a promoter that drives expression in a plant.

32. A method of producing limonene synthase, GPP synthase, and carveol synthase in a plant cell, said method comprising:

transforming a first plant cell with a nucleotide sequence encoding a limonene synthase protein operably linked to a promoter that drives expression in a plant cell, wherein said limonene synthase protein has the amino acid sequence set forth in SEQ ID NO:2;

transforming a second plant cell with a nucleotide sequence encoding a carveol synthase protein operably linked to a promoter that drives expression in a plant cell, wherein said carveol synthase protein has the amino acid sequence set forth in SEQ ID NO:6;

transforming a third plant cell with a nucleotide sequence encoding a GPP synthase protein operably linked to a promoter that drives expression in a plant cell, wherein said GPP synthase protein has the amino acid sequence set forth in SEQ ID NO:4;

producing a first fertile transgenic plant from said first plant cell;

producing a second fertile transgenic plant from said second plant cell;

producing a third fertile transgenic plant from said third plant cell;

performing a first cross between said first and second fertile transgenic plants;

recovering progeny from said first cross;

performing a second cross between said third fertile transgenic plant and said progeny of said first cross; and recovering progeny from said second cross which express limonene synthase, GPP synthase and carveol synthase.

33. The method of claim 32, wherein said second plant cell is transformed with a nucleotide sequence set forth in SEQ ID NO:5, and said third plant cell is transformed with a nucleotide sequence set forth in SEQ ID NO:3.

34. A method for manipulating a metabolic pathway in a plant cell, said method comprising transforming a plant cell with a first nucleotide sequence that is at least 80% identical to the nucleotide sequence set forth in SEQ ID NO:3 and encodes a protein having GPP synthase activity, and at least one additional nucleotide sequence which is selected from the group consisting of:

a) a nucleotide sequence that is at least 80% identical to the nucleotide sequence set forth in SEQ ID NO:1 and encodes a protein having limonene synthase activity;

b) a nucleotide sequence that is at least 80% identical to the nucleotide sequence forth in SEQ ID NO:5 and encodes a protein having carveol synthase activity; and c) a nucleotide sequence that is at least 80% identical to the nucleotide sequence set forth in SEQ ID NO:7 and encodes a protein having S-linalool synthase activity;

wherein said first and said additional nucleotide sequence are operably linked to a promoter that drives expression in a plant cell.

35. A method for manipulating a metabolic pathway in a plant cell, said method comprising transforming a plant cell with a first nucleotide sequence that is at least 80% identical to the nucleotide sequence set forth in SEQ ID NO:3 and encodes a protein having GPP synthase activity, and at least one additional nucleotide sequence which is selected from the group consisting of:
  a) a nucleotide sequence that is at least 90% identical to the nucleotide sequence set forth in SEQ ID NO:1 and encodes a protein having limonene synthase activity;
  b) a nucleotide sequence that is at least 90% identical to the nucleotide sequence forth in SEQ ID NO:5 and encodes a protein having carveol synthase activity; and
  c) a nucleotide sequence that is at least 90% identical to the nucleotide sequence set forth in SEQ ID NO:7 and encodes a protein having S-linalool synthase activity;
wherein said first and said additional nucleotide sequence are operably linked to a promoter that drives expression in a plant cell.

* * * * *

UNITED STATES PATENT AND TRADEMARK OFFICE
CERTIFICATE OF CORRECTION

PATENT NO. : 6,291,745 B1
DATED : September 18, 2001
INVENTOR(S) : Meyer et al.

It is certified that error appears in the above-identified patent and that said Letters Patent is hereby corrected as shown below:

Title page,
Item [56], References Cited, OTHER PUBLICATIONS,
Insert the following:
-- Raffa, Kenneth F., et al. (1982), Accumulation of Monoterpenes and Associated Volatiles Following Inoculation of Grand Fir with a Fungus Transmitted by the Fir Engraver, Scolytus Ventralis, Scientific Paper No. 6037, Washington State University, Can. Ent. 114: 797-810. --

Column 21,
Line 5-48, replace the existing chart with the following chart,

--

| Clone # | Callus LS[1] | Callus Limonene[2] | Plant | Plant LS | Plant Limonene |
|---|---|---|---|---|---|
| C6 | 22539 | ND | 3 | 1950 | ND |
|  |  |  | 7 | 2000 | ND |
| C19 | 9900 | ND | 6 | 2100 | ND |
| C3 | 2550 | ND | 3 | 1900 | ND |
|  |  |  | 4 | 1650 | ND |

[1] LS = Limonene Synthase

[2] ND = not detected above 0.5 ng/g fresh wt.--

Column 84,
Line 55, after "sequence" insert -- set --;
Line 65, "80%" should read -- 90% --.

UNITED STATES PATENT AND TRADEMARK OFFICE
CERTIFICATE OF CORRECTION

PATENT NO. : 6,291,745 B1
DATED : September 18, 2001
INVENTOR(S) : Meyer et al.

It is certified that error appears in the above-identified patent and that said Letters Patent is hereby corrected as shown below:

Column 85,
Line 7, after "sequence" insert -- set --.

Signed and Sealed this

Twenty-fifth Day of June, 2002

Attest:

JAMES E. ROGAN
Attesting Officer        Director of the United States Patent and Trademark Office

SEQUENCE LISTING

<160> NUMBER OF SEQ ID NOS: 8

<210> SEQ ID NO 1
<211> LENGTH: 2170
<212> TYPE: DNA
<213> ORGANISM: Mentha spicata
<220> FEATURE:
<221> NAME/KEY: misc_feature
<222> LOCATION: (0)...(0)
<223> OTHER INFORMATION: Limonene Synthase
<220> FEATURE:
<221> NAME/KEY: CDS
<222> LOCATION: (29)...(1825)

<400> SEQUENCE: 1

```
agagagagag aggaaggaaa gattaatc atg gct ctc aaa gtg tta agt gtt         52
                                Met Ala Leu Lys Val Leu Ser Val
                                 1               5
gca act caa atg gcg att cct agc aac cta acg aca tgt ctt caa ccc        100
Ala Thr Gln Met Ala Ile Pro Ser Asn Leu Thr Thr Cys Leu Gln Pro
     10                  15                  20 tca cac ttc aaa tct tct cca aaa ctg tta tct agc act aac agt agt        148
Ser His Phe Lys Ser Ser Pro Lys Leu Leu Ser Ser Thr Asn Ser Ser
 25                  30                  35                  40 agt cgg tct cgc ctc cgt gtg tat tgc tcc tcc tcg caa ctc act act        196
Ser Arg Ser Arg Leu Arg Val Tyr Cys Ser Ser Ser Gln Leu Thr Thr
                 45                  50                  55 gaa aga cga tcc gga aac tac aac cct tct cgt tgg gat gtc aac ttc        244
Glu Arg Arg Ser Gly Asn Tyr Asn Pro Ser Arg Trp Asp Val Asn Phe
             60                  65                  70 atc caa tcg ctt ctc agt gac tat aag gag gac aaa cac gtg att agg        292
Ile Gln Ser Leu Leu Ser Asp Tyr Lys Glu Asp Lys His Val Ile Arg
         75                  80                  85 gct tct gag ctg gtc act ttg gtg aag atg gaa ctg gag aaa gaa acg        340
Ala Ser Glu Leu Val Thr Leu Val Lys Met Glu Leu Glu Lys Glu Thr
     90                  95                 100 gat caa att cga caa ctt gag ttg atc gat gac ttg cag agg atg ggg        388
Asp Gln Ile Arg Gln Leu Glu Leu Ile Asp Asp Leu Gln Arg Met Gly
105                 110                 115                 120 ctg tcc gat cat ttc caa aat gag ttc aaa gaa atc ttg tcc tct ata        436
Leu Ser Asp His Phe Gln Asn Glu Phe Lys Glu Ile Leu Ser Ser Ile
                125                 130                 135 tat ctc gac cat cac tat tac aag aac cct ttt cca aaa gaa gaa agg        484
Tyr Leu Asp His His Tyr Tyr Lys Asn Pro Phe Pro Lys Glu Glu Arg
            140                 145                 150 gat ctc tac tcc aca tct ctt gca ttt agg ctc ctc aga gaa cat ggt        532
Asp Leu Tyr Ser Thr Ser Leu Ala Phe Arg Leu Leu Arg Glu His Gly
        155                 160                 165 ttt caa gtc gca caa gag gta ttc gat agt ttc aag aac gag gag ggt        580
Phe Gln Val Ala Gln Glu Val Phe Asp Ser Phe Lys Asn Glu Glu Gly
    170                 175                 180 gag ttc aaa gaa agc ctt agc gac gac acc aga gga ttg ttg caa ctg        628
Glu Phe Lys Glu Ser Leu Ser Asp Asp Thr Arg Gly Leu Leu Gln Leu
185                 190                 195                 200 tat gaa gct tcc ttt ctg ttg acg gaa ggc gaa acc acg ctc gag tca        676
Tyr Glu Ala Ser Phe Leu Leu Thr Glu Gly Glu Thr Thr Leu Glu Ser
                205                 210                 215 gcg agg gaa ttc gcc acc aaa ttt ttg gag gaa aaa gtg aac gag ggt        724
Ala Arg Glu Phe Ala Thr Lys Phe Leu Glu Glu Lys Val Asn Glu Gly
            220                 225                 230
```

```
ggt gtt gat ggc gac ctt tta aca aga atc gca tat tct ttg gac atc    772
Gly Val Asp Gly Asp Leu Leu Thr Arg Ile Ala Tyr Ser Leu Asp Ile
        235                 240                 245 cct ctt cat tgg agg att aaa agg cca aat gca cct gtg tgg atc gaa    820
Pro Leu His Trp Arg Ile Lys Arg Pro Asn Ala Pro Val Trp Ile Glu
    250                 255                 260 tgg tat agg aag agg ccc gac atg aat cca gta gtg ttg gag ctt gcc    868
Trp Tyr Arg Lys Arg Pro Asp Met Asn Pro Val Val Leu Glu Leu Ala
265                 270                 275                 280 ata ctc gac tta aat att gtt caa gca caa ttt caa gaa gag ctc aaa    916
Ile Leu Asp Leu Asn Ile Val Gln Ala Gln Phe Gln Glu Glu Leu Lys
                285                 290                 295 gaa tcc ttc agg tgg tgg aga aat act ggg ttt gtt gag aag ctg ccc    964
Glu Ser Phe Arg Trp Trp Arg Asn Thr Gly Phe Val Glu Lys Leu Pro
            300                 305                 310 ttc gca agg gat aga ctg gtg gaa tgc tac ttt tgg aat act ggg atc   1012
Phe Ala Arg Asp Arg Leu Val Glu Cys Tyr Phe Trp Asn Thr Gly Ile
        315                 320                 325 atc gag cca cgt cag cat gca agt gca agg ata atg atg ggc aaa gtc   1060
Ile Glu Pro Arg Gln His Ala Ser Ala Arg Ile Met Met Gly Lys Val
    330                 335                 340 aac gct ctg att acg gtg atc gat gat att tat gat gtc tat ggc acc   1108
Asn Ala Leu Ile Thr Val Ile Asp Asp Ile Tyr Asp Val Tyr Gly Thr
345                 350                 355                 360 tta gaa gaa ctc gaa caa ttc act gac ctc att cga aga tgg gat ata   1156
Leu Glu Glu Leu Glu Gln Phe Thr Asp Leu Ile Arg Arg Trp Asp Ile
                365                 370                 375 aac tca atc gac caa ctt ccc gat tac atg caa ctg tgc ttt ctt gca   1204
Asn Ser Ile Asp Gln Leu Pro Asp Tyr Met Gln Leu Cys Phe Leu Ala
            380                 385                 390 ctc aac aac ttc gtc gat gat aca tcg tac gat gtt atg aag gag aaa   1252
Leu Asn Asn Phe Val Asp Asp Thr Ser Tyr Asp Val Met Lys Glu Lys
        395                 400                 405 ggc gtc aac gtt ata ccc tac ctg cgg caa tcg tgg gtt gat ttg gcg   1300
Gly Val Asn Val Ile Pro Tyr Leu Arg Gln Ser Trp Val Asp Leu Ala
    410                 415                 420 gat aag tat atg gta gag gca cgg tgg ttc tac ggc ggg cac aaa cca   1348
Asp Lys Tyr Met Val Glu Ala Arg Trp Phe Tyr Gly Gly His Lys Pro
425                 430                 435                 440 agt ttg gaa gag tat ttg gag aac tca tgg cag tca ata agt ggg ccc   1396
Ser Leu Glu Glu Tyr Leu Glu Asn Ser Trp Gln Ser Ile Ser Gly Pro
                445                 450                 455 tgt atg tta acg cac ata ttc ttc cga gta aca gat tcg ttc aca aag   1444
Cys Met Leu Thr His Ile Phe Phe Arg Val Thr Asp Ser Phe Thr Lys
            460                 465                 470 gag acc gtc gac agt ttg tac aaa tac cac gat tta gtt cgt tgg tca   1492
Glu Thr Val Asp Ser Leu Tyr Lys Tyr His Asp Leu Val Arg Trp Ser
        475                 480                 485 tcc ttc gtt ctg cgg ctt gct gat gat ttg gga acc tcg gtg gaa gag   1540
Ser Phe Val Leu Arg Leu Ala Asp Asp Leu Gly Thr Ser Val Glu Glu
    490                 495                 500 gtg agc aga ggg gat gtg ccg aaa tca ctt cag tgc tac atg agt gac   1588
Val Ser Arg Gly Asp Val Pro Lys Ser Leu Gln Cys Tyr Met Ser Asp
505                 510                 515                 520 tac aat gca tcg gag gcg gag gcg cgg aag cac gtg aaa tgg ctg ata   1636
Tyr Asn Ala Ser Glu Ala Glu Ala Arg Lys His Val Lys Trp Leu Ile
                525                 530                 535 gcg gag gtg tgg aag aag atg aat gcg gag agg gtg tcg aag gat tct   1684
Ala Glu Val Trp Lys Lys Met Asn Ala Glu Arg Val Ser Lys Asp Ser
            540                 545                 550
```

-continued

```
cca ttc ggc aaa gat ttt ata gga tgt gca gtt gat tta gga agg atg     1732
Pro Phe Gly Lys Asp Phe Ile Gly Cys Ala Val Asp Leu Gly Arg Met
        555                 560                 565 gcg cag ttg atg tac cat aat gga gat ggg cac ggc aca caa cac cct     1780
Ala Gln Leu Met Tyr His Asn Gly Asp Gly His Gly Thr Gln His Pro
    570                 575                 580 att ata cat caa caa atg acc aga acc tta ttc gag ccc ttt gca         1825
Ile Ile His Gln Gln Met Thr Arg Thr Leu Phe Glu Pro Phe Ala
585                 590                 595 tgagagatga tgacgagcca tcgtttactt acttaaattc taccaaagtt tttcgaaggc   1885
atagttcgta attttcaag caccaataaa taaggagaat cggctcaaac aaacgtggca    1945
tttgccacca cgtgagcaca agggagagtc tgtcgtcgtt tatggatgaa ctattcaatt   2005
tttatgcatg taataattaa gttcaagttc aagagccttc tgcatattta actatgtatt   2065
tgaatttatc gagtgtgatt ttctgtcttt ggcaacatat attttgtca tatgtggcat    2125 cttattatga tatcatacag tgtttatgga tgatatgata ctatc                   2170

<210> SEQ ID NO 2
<211> LENGTH: 599
<212> TYPE: PRT
<213> ORGANISM: Mentha spicata

<400> SEQUENCE: 2

Met Ala Leu Lys Val Leu Ser Val Ala Thr Gln Met Ala Ile Pro Ser
 1               5                  10                  15

Asn Leu Thr Thr Cys Leu Gln Pro Ser His Phe Lys Ser Ser Pro Lys
            20                  25                  30

Leu Leu Ser Ser Thr Asn Ser Ser Arg Ser Arg Leu Arg Val Tyr
        35                  40                  45

Cys Ser Ser Ser Gln Leu Thr Thr Glu Arg Arg Ser Gly Asn Tyr Asn
    50                  55                  60

Pro Ser Arg Trp Asp Val Asn Phe Ile Gln Ser Leu Leu Ser Asp Tyr
65                  70                  75                  80

Lys Glu Asp Lys His Val Ile Arg Ala Ser Glu Leu Val Thr Leu Val
                85                  90                  95

Lys Met Glu Leu Glu Lys Glu Thr Asp Gln Ile Arg Gln Leu Glu Leu
            100                 105                 110

Ile Asp Asp Leu Gln Arg Met Gly Leu Ser Asp His Phe Gln Asn Glu
        115                 120                 125

Phe Lys Glu Ile Leu Ser Ser Ile Tyr Leu Asp His His Tyr Tyr Lys
    130                 135                 140

Asn Pro Phe Pro Lys Glu Glu Arg Asp Leu Tyr Ser Thr Ser Leu Ala
145                 150                 155                 160

Phe Arg Leu Leu Arg Glu His Gly Phe Gln Val Ala Gln Glu Val Phe
                165                 170                 175

Asp Ser Phe Lys Asn Glu Glu Gly Glu Phe Lys Glu Ser Leu Ser Asp
            180                 185                 190

Asp Thr Arg Gly Leu Leu Gln Leu Tyr Glu Ala Ser Phe Leu Leu Thr
        195                 200                 205

Glu Gly Glu Thr Thr Leu Glu Ser Ala Arg Glu Phe Ala Thr Lys Phe
    210                 215                 220

Leu Glu Glu Lys Val Asn Glu Gly Gly Val Asp Gly Asp Leu Leu Thr
225                 230                 235                 240
```

```
Arg Ile Ala Tyr Ser Leu Asp Ile Pro Leu His Trp Arg Ile Lys Arg
            245                 250                 255
Pro Asn Ala Pro Val Trp Ile Glu Trp Tyr Arg Lys Arg Pro Asp Met
        260                 265                 270
Asn Pro Val Val Leu Glu Leu Ala Ile Leu Asp Leu Asn Ile Val Gln
    275                 280                 285
Ala Gln Phe Gln Glu Glu Leu Lys Glu Ser Phe Arg Trp Trp Arg Asn
290                 295                 300
Thr Gly Phe Val Glu Lys Leu Pro Phe Ala Arg Asp Arg Leu Val Glu
305                 310                 315                 320
Cys Tyr Phe Trp Asn Thr Gly Ile Ile Glu Pro Arg Gln His Ala Ser
                325                 330                 335
Ala Arg Ile Met Met Gly Lys Val Asn Ala Leu Ile Thr Val Ile Asp
            340                 345                 350
Asp Ile Tyr Asp Val Tyr Gly Thr Leu Glu Glu Leu Glu Gln Phe Thr
        355                 360                 365
Asp Leu Ile Arg Arg Trp Asp Ile Asn Ser Ile Asp Gln Leu Pro Asp
    370                 375                 380
Tyr Met Gln Leu Cys Phe Leu Ala Leu Asn Asn Phe Val Asp Asp Thr
385                 390                 395                 400
Ser Tyr Asp Val Met Lys Glu Lys Gly Val Asn Val Ile Pro Tyr Leu
                405                 410                 415
Arg Gln Ser Trp Val Asp Leu Ala Asp Lys Tyr Met Val Glu Ala Arg
            420                 425                 430
Trp Phe Tyr Gly Gly His Lys Pro Ser Leu Glu Glu Tyr Leu Glu Asn
        435                 440                 445
Ser Trp Gln Ser Ile Ser Gly Pro Cys Met Leu Thr His Ile Phe Phe
    450                 455                 460
Arg Val Thr Asp Ser Phe Thr Lys Glu Thr Val Asp Ser Leu Tyr Lys
465                 470                 475                 480
Tyr His Asp Leu Val Arg Trp Ser Ser Phe Val Leu Arg Leu Ala Asp
                485                 490                 495
Asp Leu Gly Thr Ser Val Glu Glu Val Ser Arg Gly Asp Val Pro Lys
            500                 505                 510
Ser Leu Gln Cys Tyr Met Ser Asp Tyr Asn Ala Ser Glu Ala Glu Ala
        515                 520                 525
Arg Lys His Val Lys Trp Leu Ile Ala Glu Val Trp Lys Lys Met Asn
    530                 535                 540
Ala Glu Arg Val Ser Lys Asp Ser Pro Phe Gly Lys Asp Phe Ile Gly
545                 550                 555                 560
Cys Ala Val Asp Leu Gly Arg Met Ala Gln Leu Met Tyr His Asn Gly
                565                 570                 575
Asp Gly His Gly Thr Gln His Pro Ile Ile His Gln Gln Met Thr Arg
            580                 585                 590
Thr Leu Phe Glu Pro Phe Ala
        595

<210> SEQ ID NO 3
<211> LENGTH: 1131
<212> TYPE: DNA
<213> ORGANISM: Mentha spicata
<220> FEATURE:
<221> NAME/KEY: misc_feature
<222> LOCATION: (0)...(0)
<223> OTHER INFORMATION: GPP Synthase
```

-continued

```
<220> FEATURE:
<221> NAME/KEY: CDS
<222> LOCATION: (6)...(944)

<400> SEQUENCE: 3 tcaaa atg gcc att aat ctc tcc cat atc aac tcc aaa aca tgt ttc cct        50
      Met Ala Ile Asn Leu Ser His Ile Asn Ser Lys Thr Cys Phe Pro
      1               5                  10                  15 ctc aaa aca aga tct gat ctc agc cgt tct tct tcc gcg cgt tgc atg          98
Leu Lys Thr Arg Ser Asp Leu Ser Arg Ser Ser Ser Ala Arg Cys Met
                20                  25                  30 cca act gcc gcc gct gcc gcc ttc ccc act atc gcc acc gcc gcc caa         146
Pro Thr Ala Ala Ala Ala Ala Phe Pro Thr Ile Ala Thr Ala Ala Gln
            35                  40                  45 agt cag ccg tac tgg gcc gcc atc gag gcc gac ata gag aga tac ctg         194
Ser Gln Pro Tyr Trp Ala Ala Ile Glu Ala Asp Ile Glu Arg Tyr Leu
        50                  55                  60 aag aaa tcc atc aca ata agg ccg ccg gag aca gtt ttc ggg ccc atg         242
Lys Lys Ser Ile Thr Ile Arg Pro Pro Glu Thr Val Phe Gly Pro Met
    65                  70                  75 cac cac ctc acc ttc gcc gcc cca gcc acc gcc gcc tcc acc cta tgc         290
His His Leu Thr Phe Ala Ala Pro Ala Thr Ala Ala Ser Thr Leu Cys
80                  85                  90                  95 ttg gcg gcg tgc gag ctc gtc ggc ggc gac cga agc caa gcc atg gca         338
Leu Ala Ala Cys Glu Leu Val Gly Gly Asp Arg Ser Gln Ala Met Ala
                100                 105                 110 gcc gcg gcg gcg atc cat ctc gtg cac gcg gca gcc tac gtc cac gag         386
Ala Ala Ala Ala Ile His Leu Val His Ala Ala Ala Tyr Val His Glu
            115                 120                 125 cac ctc cct cta acc gac ggg tcg agg ccc gta tcc aag ccc gca atc         434
His Leu Pro Leu Thr Asp Gly Ser Arg Pro Val Ser Lys Pro Ala Ile
        130                 135                 140 cag cac aag tac ggc ccg aac gtc gag ctc ctc acc gga gac ggg att         482
Gln His Lys Tyr Gly Pro Asn Val Glu Leu Leu Thr Gly Asp Gly Ile
    145                 150                 155 gtc ccg ttc ggg ttt gag ttg ctg gcc ggg tca gtg gac ccg gcc cga         530
Val Pro Phe Gly Phe Glu Leu Leu Ala Gly Ser Val Asp Pro Ala Arg
160                 165                 170                 175 aca gac gac ccg gat agg att ctg aga gtt ata ata gag atc agt cgg         578
Thr Asp Asp Pro Asp Arg Ile Leu Arg Val Ile Ile Glu Ile Ser Arg
                180                 185                 190 gcc ggc ggg ccg gag gga atg ata agc ggg ctg cat agg gaa gaa gaa         626
Ala Gly Gly Pro Glu Gly Met Ile Ser Gly Leu His Arg Glu Glu Glu
            195                 200                 205 att gtt gat gga aat acg agt tta gac ttc att gaa tat gtg tgc aag         674
Ile Val Asp Gly Asn Thr Ser Leu Asp Phe Ile Glu Tyr Val Cys Lys
        210                 215                 220 aaa aaa tac ggc gag atg cat gct tgc ggc gcg gct tgt gga gcc ata         722
Lys Lys Tyr Gly Glu Met His Ala Cys Gly Ala Ala Cys Gly Ala Ile
    225                 230                 235 ttg ggc ggc gca gcc gag gag gag att cag aag ctg agg aat ttc ggg         770
Leu Gly Gly Ala Ala Glu Glu Glu Ile Gln Lys Leu Arg Asn Phe Gly
240                 245                 250                 255 ctt tat caa gga act ctc aga gga atg atg gaa atg aaa aat tct cat         818
Leu Tyr Gln Gly Thr Leu Arg Gly Met Met Glu Met Lys Asn Ser His
                260                 265                 270 caa tta att gat gag aat ata att gga aaa ttg aaa gaa ttg gct ctc         866
Gln Leu Ile Asp Glu Asn Ile Ile Gly Lys Leu Lys Glu Leu Ala Leu
            275                 280                 285
```

```
gag gag ttg gga ggc ttc cac ggg aag aac gct gag ctg atg tcg agc       914
Glu Glu Leu Gly Gly Phe His Gly Lys Asn Ala Glu Leu Met Ser Ser
        290                 295                 300 ctt gta gcc gag ccg agc ctt tac gcg gct tagagctatt cggatccttc         964
Leu Val Ala Glu Pro Ser Leu Tyr Ala Ala
    305                 310 attgcatttt catgcgacat cttcatattc atattgcata atattttta agccagttat     1024 tttttatta tgaattttt taactgttat tgatttcgaa aatactgaca atcatctaaa      1084
ataaagtaaa tatagtaagg atgaaaaaaa aaaaaaaaa aaaaaaa                    1131

<210> SEQ ID NO 4
<211> LENGTH: 313
<212> TYPE: PRT
<213> ORGANISM: Mentha spicata

<400> SEQUENCE: 4

Met Ala Ile Asn Leu Ser His Ile Asn Ser Lys Thr Cys Phe Pro Leu
  1               5                  10                  15

Lys Thr Arg Ser Asp Leu Ser Arg Ser Ser Ala Arg Cys Met Pro
             20                  25                  30

Thr Ala Ala Ala Ala Phe Pro Thr Ile Ala Thr Ala Ala Gln Ser
         35                  40                  45

Gln Pro Tyr Trp Ala Ala Ile Glu Ala Asp Ile Glu Arg Tyr Leu Lys
     50                  55                  60

Lys Ser Ile Thr Ile Arg Pro Pro Glu Thr Val Phe Gly Pro Met His
 65                  70                  75                  80

His Leu Thr Phe Ala Ala Pro Ala Thr Ala Ala Ser Thr Leu Cys Leu
                 85                  90                  95

Ala Ala Cys Glu Leu Val Gly Gly Asp Arg Ser Gln Ala Met Ala Ala
            100                 105                 110

Ala Ala Ile His Leu Val His Ala Ala Ala Tyr Val His Glu His
        115                 120                 125

Leu Pro Leu Thr Asp Gly Ser Arg Pro Val Ser Lys Pro Ala Ile Gln
    130                 135                 140

His Lys Tyr Gly Pro Asn Val Glu Leu Leu Thr Gly Asp Gly Ile Val
145                 150                 155                 160

Pro Phe Gly Phe Glu Leu Leu Ala Gly Ser Val Asp Pro Ala Arg Thr
                165                 170                 175

Asp Asp Pro Asp Arg Ile Leu Arg Val Ile Glu Ile Ser Arg Ala
            180                 185                 190

Gly Gly Pro Glu Gly Met Ile Ser Gly Leu His Arg Glu Glu Ile
        195                 200                 205

Val Asp Gly Asn Thr Ser Leu Asp Phe Ile Glu Tyr Val Cys Lys Lys
    210                 215                 220

Lys Tyr Gly Glu Met His Ala Cys Gly Ala Ala Cys Gly Ala Ile Leu
225                 230                 235                 240

Gly Gly Ala Ala Glu Glu Glu Ile Gln Lys Leu Arg Asn Phe Gly Leu
                245                 250                 255

Tyr Gln Gly Thr Leu Arg Gly Met Met Glu Met Lys Asn Ser His Gln
            260                 265                 270

Leu Ile Asp Glu Asn Ile Ile Gly Lys Leu Lys Glu Leu Ala Leu Glu
        275                 280                 285

Glu Leu Gly Gly Phe His Gly Lys Asn Ala Glu Leu Met Ser Ser Leu
    290                 295                 300
```

```
Val Ala Glu Pro Ser Leu Tyr Ala Ala
305                 310
```

<210> SEQ ID NO 5
<211> LENGTH: 1762
<212> TYPE: DNA
<213> ORGANISM: Mentha spicata
<220> FEATURE:
<221> NAME/KEY: misc_feature
<222> LOCATION: (0)...(0)
<223> OTHER INFORMATION: Carveol Synthase
<220> FEATURE:
<221> NAME/KEY: CDS
<222> LOCATION: (20)...(1507)

<400> SEQUENCE: 5

```
aaaaaacwaa aaagaaacw atg gag ctc gac ctt ttg tcg gca att ata atc       52
                    Met Glu Leu Asp Leu Leu Ser Ala Ile Ile Ile
                     1               5                      10 ctt gtg gca acc tac atc gta tcc ctc cta atc aac caa tgg cga aaa      100
Leu Val Ala Thr Tyr Ile Val Ser Leu Leu Ile Asn Gln Trp Arg Lys
             15                  20                  25 tcg aaa tcc caa caa aac cta cct ccg agc cct ccg aag ctg ccg gtg      148
Ser Lys Ser Gln Gln Asn Leu Pro Pro Ser Pro Pro Lys Leu Pro Val
         30                  35                  40 atc ggc cac ctc cac ttc ctg tgg gga ggg ctt ccc cag cac gtg ttt      196
Ile Gly His Leu His Phe Leu Trp Gly Gly Leu Pro Gln His Val Phe
     45                  50                  55 agg agc ata gcc cag aag tac ggg ccg gtg gcg cac gtg cag ctg gga      244
Arg Ser Ile Ala Gln Lys Tyr Gly Pro Val Ala His Val Gln Leu Gly
 60                  65                  70                  75 gaa gtg tac tcg gtg gtg ctg tcg tcg gcg gag gca gcg ccg cag gcg      292
Glu Val Tyr Ser Val Val Leu Ser Ser Ala Glu Ala Ala Pro Gln Ala
                 80                  85                  90 atg aag gtg ctg gac ccg aac ttc gcc gac cgg ttc gac ggc atc ggg      340
Met Lys Val Leu Asp Pro Asn Phe Ala Asp Arg Phe Asp Gly Ile Gly
             95                 100                 105 tcc agg acc atg tgg tac gac aaa gat gac atc atc ttc agc cct tac      388
Ser Arg Thr Met Trp Tyr Asp Lys Asp Asp Ile Ile Phe Ser Pro Tyr
         110                 115                 120 aac gat cac tgg cgc cag atg cgg agg atc tgc gtg aca gag ctg ctg      436
Asn Asp His Trp Arg Gln Met Arg Arg Ile Cys Val Thr Glu Leu Leu
     125                 130                 135 agc ccg aag aac gtc agg tcc ttc ggg tac ata agg cag gag gag atc      484
Ser Pro Lys Asn Val Arg Ser Phe Gly Tyr Ile Arg Gln Glu Glu Ile
140                 145                 150                 155 gag cgc ctc atc cgg ctg ctc ggg tcg tcg ggg gga gcg ccg gtc gac      532
Glu Arg Leu Ile Arg Leu Leu Gly Ser Ser Gly Gly Ala Pro Val Asp
                 160                 165                 170 gtg acg gag gag gtg tcg aag atg tcg tgt gtc gtc gtg tgc agg gcg      580
Val Thr Glu Glu Val Ser Lys Met Ser Cys Val Val Val Cys Arg Ala
             175                 180                 185 gcg ttc ggg agt gtg ctc aag gac cag ggt tcg ttg gcg gag ttg gtg      628
Ala Phe Gly Ser Val Leu Lys Asp Gln Gly Ser Leu Ala Glu Leu Val
         190                 195                 200 aag gag tcg ctg gca ttg gcg tcc ggg ttt gag ctg gcg gat ctc tac      676
Lys Glu Ser Leu Ala Leu Ala Ser Gly Phe Glu Leu Ala Asp Leu Tyr
     205                 210                 215 cct tcc tca tgg ctc ctc aac ctg ctt agc ttg aac aag tac agg ttg      724
Pro Ser Ser Trp Leu Leu Asn Leu Leu Ser Leu Asn Lys Tyr Arg Leu
220                 225                 230                 235
```

```
cag agg atg cgc cgc cgc ctc gat cac atc ctt gat ggg ttc ctg gag      772
Gln Arg Met Arg Arg Arg Leu Asp His Ile Leu Asp Gly Phe Leu Glu
            240                 245                 250 gag cat agg gag aag aag agc ggc gac ttt gga ggc gag gac atc gtc      820
Glu His Arg Glu Lys Lys Ser Gly Asp Phe Gly Gly Glu Asp Ile Val
        255                 260                 265 gac gtt ctt ttc agg atg cag ccg ggc agc gac agc aaa att ccc att      868
Asp Val Leu Phe Arg Met Gln Pro Gly Ser Asp Ser Lys Ile Pro Ile
    270                 275                 280 act tcc aat tgc atc aag ggt ttc att ttc gac acc ttc tcc gcg gga      916
Thr Ser Asn Cys Ile Lys Gly Phe Ile Phe Asp Thr Phe Ser Ala Gly
285                 290                 295 gct gaa acg tct tcg acg acc atc tca tgg gcg ttg tcg gaa ctg atg      964
Ala Glu Thr Ser Ser Thr Thr Ile Ser Trp Ala Leu Ser Glu Leu Met
300                 305                 310                 315 agg aat ccg gcg aag atg gcc aag gtg cag gcg gag gta aga gag gcg     1012
Arg Asn Pro Ala Lys Met Ala Lys Val Gln Ala Glu Val Arg Glu Ala
                320                 325                 330 ctc aag gga aag aca gtc gtg gat ttg agc gag gtg caa gag cta aaa     1060
Leu Lys Gly Lys Thr Val Val Asp Leu Ser Glu Val Gln Glu Leu Lys
            335                 340                 345 tac ctg aga tcg gtg tta aag gag act ctg agg ctg cac cct ccc ttt     1108
Tyr Leu Arg Ser Val Leu Lys Glu Thr Leu Arg Leu His Pro Pro Phe
        350                 355                 360 cca tta atc cca aga caa tcc agg gaa gaa tgc gag gtt aac ggg tac     1156
Pro Leu Ile Pro Arg Gln Ser Arg Glu Glu Cys Glu Val Asn Gly Tyr
    365                 370                 375 acg att ccg gcc aaa act aga atc ttc atc aac gtc tgg gct atc gga     1204
Thr Ile Pro Ala Lys Thr Arg Ile Phe Ile Asn Val Trp Ala Ile Gly
380                 385                 390                 395 agg gat ccc caa tac tgg gaa gat ccc gac acc ttc cgc cct gag aga     1252
Arg Asp Pro Gln Tyr Trp Glu Asp Pro Asp Thr Phe Arg Pro Glu Arg
                400                 405                 410 ttc gat gag gtt tcc agg gat ttc atg gga aac gat ttc gag ttc atc     1300
Phe Asp Glu Val Ser Arg Asp Phe Met Gly Asn Asp Phe Glu Phe Ile
            415                 420                 425 cca ttc ggg gcg ggt cga aga atc tgc ccc ggt tta cat ttc ggg ctg     1348
Pro Phe Gly Ala Gly Arg Arg Ile Cys Pro Gly Leu His Phe Gly Leu
        430                 435                 440 gca aat gtt gag atc cca ttg gcg caa ctg ctc tac cac ttc gac tgg     1396
Ala Asn Val Glu Ile Pro Leu Ala Gln Leu Leu Tyr His Phe Asp Trp
    445                 450                 455 aaa ttg cca caa gga atg act gat gcc gac ttg gca ctg acg gag acc     1444
Lys Leu Pro Gln Gly Met Thr Asp Ala Asp Leu Ala Leu Thr Glu Thr
460                 465                 470                 475 cca ggt ctt tct ggg cca aaa aag aaa aat gtt tgc ttg gtt ccc aca     1492
Pro Gly Leu Ser Gly Pro Lys Lys Lys Asn Val Cys Leu Val Pro Thr
                480                 485                 490 ctc tat aaa agt cct taaccactaa gaagttagca taataagaca tctaaaattg     1547
Leu Tyr Lys Ser Pro
            495 tcataatcat ctaattattg ttacacttct tctatcatgt cattttgaga agtgtcttat    1607 agaggtggcc acggttccgg ttccagttcg gaagcggaac cgaaccatca gttacggttc    1667 tcagcaagaa gcgaaccgtc ccgccccccc tactgtgttt gagatataaa acacataaaa    1727 taaaataaaa aaaacgctat ttttttttaa aaaaa                              1762

<210> SEQ ID NO 6
<211> LENGTH: 496
```

```
<212> TYPE: PRT
<213> ORGANISM: Mentha spicata

<400> SEQUENCE: 6

Met Glu Leu Asp Leu Leu Ser Ala Ile Ile Leu Val Ala Thr Tyr
 1               5                  10                  15

Ile Val Ser Leu Leu Ile Asn Gln Trp Arg Lys Ser Lys Ser Gln Gln
                20                  25                  30

Asn Leu Pro Pro Ser Pro Pro Lys Leu Pro Val Ile Gly His Leu His
                35                  40                  45

Phe Leu Trp Gly Gly Leu Pro Gln His Val Phe Arg Ser Ile Ala Gln
        50                  55                  60

Lys Tyr Gly Pro Val Ala His Val Gln Leu Gly Glu Val Tyr Ser Val
65                  70                  75                  80

Val Leu Ser Ser Ala Glu Ala Pro Gln Ala Met Lys Val Leu Asp
                85                  90                  95

Pro Asn Phe Ala Asp Arg Phe Asp Gly Ile Gly Ser Arg Thr Met Trp
                100                 105                 110

Tyr Asp Lys Asp Asp Ile Ile Phe Ser Pro Tyr Asn Asp His Trp Arg
                115                 120                 125

Gln Met Arg Arg Ile Cys Val Thr Glu Leu Leu Ser Pro Lys Asn Val
130                 135                 140

Arg Ser Phe Gly Tyr Ile Arg Gln Glu Glu Ile Glu Arg Leu Ile Arg
145                 150                 155                 160

Leu Leu Gly Ser Ser Gly Gly Ala Pro Val Asp Val Thr Glu Glu Val
                165                 170                 175

Ser Lys Met Ser Cys Val Val Cys Arg Ala Ala Phe Gly Ser Val
                180                 185                 190

Leu Lys Asp Gln Gly Ser Leu Ala Glu Leu Val Lys Glu Ser Leu Ala
                195                 200                 205

Leu Ala Ser Gly Phe Glu Leu Ala Asp Leu Tyr Pro Ser Ser Trp Leu
        210                 215                 220

Leu Asn Leu Leu Ser Leu Asn Lys Tyr Arg Leu Gln Arg Met Arg Arg
225                 230                 235                 240

Arg Leu Asp His Ile Leu Asp Gly Phe Leu Glu Glu His Arg Glu Lys
                245                 250                 255

Lys Ser Gly Asp Phe Gly Gly Glu Asp Ile Val Asp Val Leu Phe Arg
                260                 265                 270

Met Gln Pro Gly Ser Asp Ser Lys Ile Pro Ile Thr Ser Asn Cys Ile
                275                 280                 285

Lys Gly Phe Ile Phe Asp Thr Phe Ser Ala Gly Ala Glu Thr Ser Ser
                290                 295                 300

Thr Thr Ile Ser Trp Ala Leu Ser Glu Leu Met Arg Asn Pro Ala Lys
305                 310                 315                 320

Met Ala Lys Val Gln Ala Glu Val Arg Glu Ala Leu Lys Gly Lys Thr
                325                 330                 335

Val Val Asp Leu Ser Glu Val Gln Glu Leu Lys Tyr Leu Arg Ser Val
                340                 345                 350

Leu Lys Glu Thr Leu Arg Leu His Pro Pro Phe Pro Leu Ile Pro Arg
                355                 360                 365

Gln Ser Arg Glu Glu Cys Glu Val Asn Gly Tyr Thr Ile Pro Ala Lys
        370                 375                 380

Thr Arg Ile Phe Ile Asn Val Trp Ala Ile Gly Arg Asp Pro Gln Tyr
385                 390                 395                 400
```

-continued

```
Trp Glu Asp Pro Asp Thr Phe Arg Pro Glu Arg Phe Asp Glu Val Ser
            405                 410                 415
Arg Asp Phe Met Gly Asn Asp Phe Glu Phe Ile Pro Phe Gly Ala Gly
        420                 425                 430
Arg Arg Ile Cys Pro Gly Leu His Phe Gly Leu Ala Asn Val Glu Ile
    435                 440                 445
Pro Leu Ala Gln Leu Leu Tyr His Phe Asp Trp Lys Leu Pro Gln Gly
450                 455                 460
Met Thr Asp Ala Asp Leu Ala Leu Thr Glu Thr Pro Gly Leu Ser Gly
465                 470                 475                 480
Pro Lys Lys Lys Asn Val Cys Leu Val Pro Thr Leu Tyr Lys Ser Pro
                485                 490                 495
```

<210> SEQ ID NO 7
<211> LENGTH: 2681
<212> TYPE: DNA
<213> ORGANISM: Clarkia breweri
<220> FEATURE:
<221> NAME/KEY: misc_feature
<222> LOCATION: (0)...(0)
<223> OTHER INFORMATION: S-Linalool Synthase
<220> FEATURE:
<221> NAME/KEY: CDS
<222> LOCATION: (28)...(2637)

<400> SEQUENCE: 7

```
aaccaaacca ccttaaacaa gacaacc atg cag ctc ata aca aat ttc tcc tca      54
                              Met Gln Leu Ile Thr Asn Phe Ser Ser
                                1               5 tca tca tca gaa ttg cag ttt ctt gtg gat aag gtt aag aga gaa tca     102
Ser Ser Ser Glu Leu Gln Phe Leu Val Asp Lys Val Lys Arg Glu Ser
 10              15                  20                  25 ttg tct tct tca tca tct aat act cag aat ttg ttt ctc tca act tca     150
Leu Ser Ser Ser Ser Ser Asn Thr Gln Asn Leu Phe Leu Ser Thr Ser
            30                  35                  40 cct tat gac act gct tgg ctc gcc ctt atc cct cat cct cat cat cac     198
Pro Tyr Asp Thr Ala Trp Leu Ala Leu Ile Pro His Pro His His His
        45                  50                  55 cat cac cat ggc cga ccc atg ttt gaa aaa tgt ctg caa tgg att ctc     246
His His His Gly Arg Pro Met Phe Glu Lys Cys Leu Gln Trp Ile Leu
    60                  65                  70 cat aac cag aca cca caa ggt ttc tgg gca gca gct ggt gac aat att     294
His Asn Gln Thr Pro Gln Gly Phe Trp Ala Ala Ala Gly Asp Asn Ile
75                  80                  85 tcc gac acc gac gat gac gtc acc ctg gat tgt ctt cta tca acc ttg     342
Ser Asp Thr Asp Asp Asp Val Thr Leu Asp Cys Leu Leu Ser Thr Leu
 90                  95                 100                 105 gct tgc tta gtt gca ctc aaa agg tgg cag ctt gct ccc gac atg att     390
Ala Cys Leu Val Ala Leu Lys Arg Trp Gln Leu Ala Pro Asp Met Ile
            110                 115                 120 cat aaa gga ttg gaa ttt gta aat aga aac aca gag aga ctt gta atg     438
His Lys Gly Leu Glu Phe Val Asn Arg Asn Thr Glu Arg Leu Val Met
        125                 130                 135 aag cag aag ccg agc gac gtt cct cgt tgg ttc acc atc atg ttc ccg     486
Lys Gln Lys Pro Ser Asp Val Pro Arg Trp Phe Thr Ile Met Phe Pro
    140                 145                 150 gcg atg ctc gag ctt gcc gga gct tcc agt ctc cga gtc gat ttc agc     534
Ala Met Leu Glu Leu Ala Gly Ala Ser Ser Leu Arg Val Asp Phe Ser
155                 160                 165
```

-continued

| | |
|---|---|
| gag aat ctt aac aga atc ttg gtg gaa cta tct caa aat agg gat gat<br>Glu Asn Leu Asn Arg Ile Leu Val Glu Leu Ser Gln Asn Arg Asp Asp<br>170                       175                   180                   185 | 582 |
| att ctc aca agg gag gaa gtt gat gag aag aag caa tac tca cca ttg<br>Ile Leu Thr Arg Glu Glu Val Asp Glu Lys Lys Gln Tyr Ser Pro Leu<br>                   190                   195                   200 | 630 |
| cta cta ttt cta gaa gca ttg cct gca caa tcc tat gac aat gat gtt<br>Leu Leu Phe Leu Glu Ala Leu Pro Ala Gln Ser Tyr Asp Asn Asp Val<br>             205                   210                   215 | 678 |
| cta aag caa att ata gac aag aac ttg agc aat gat ggt tct tta ttg<br>Leu Lys Gln Ile Ile Asp Lys Asn Leu Ser Asn Asp Gly Ser Leu Leu<br>           220                   225                   230 | 726 |
| caa tcg cct tct gct aca gca aga gca tac atg ata aca gga aat acc<br>Gln Ser Pro Ser Ala Thr Ala Arg Ala Tyr Met Ile Thr Gly Asn Thr<br>       235                   240                   245 | 774 |
| aga tgc tta tcg tat cta cac tct tta aca aat agc tgc tct aat gga<br>Arg Cys Leu Ser Tyr Leu His Ser Leu Thr Asn Ser Cys Ser Asn Gly<br>250                       255                   260                   265 | 822 |
| gga gta cca tca ttc tat cct gtt gac gac gac ctc cat gat ctt gtc<br>Gly Val Pro Ser Phe Tyr Pro Val Asp Asp Asp Leu His Asp Leu Val<br>                   270                   275                   280 | 870 |
| atg gtg aat caa ctg aca agg tcg ggt ttg act gaa cat ctc atc ccg<br>Met Val Asn Gln Leu Thr Arg Ser Gly Leu Thr Glu His Leu Ile Pro<br>           285                   290                   295 | 918 |
| gag att gac cac ctt cta ctc aaa gtt caa aag aac tac aaa tac aaa<br>Glu Ile Asp His Leu Leu Leu Lys Val Gln Lys Asn Tyr Lys Tyr Lys<br>             300                   305                   310 | 966 |
| aaa gca tca cca aaa tca ttg tat agc att gct gcg gaa cta tac agg<br>Lys Ala Ser Pro Lys Ser Leu Tyr Ser Ile Ala Ala Glu Leu Tyr Arg<br>       315                   320                   325 | 1014 |
| gat tca tta gca ttt tgg ttg ctt cga gtc aat aat cac tgg gta tca<br>Asp Ser Leu Ala Phe Trp Leu Leu Arg Val Asn Asn His Trp Val Ser<br>330                       335                   340                   345 | 1062 |
| cca tca att ttt tgt tgg ttt tta gat gac gac gaa atc cgt gat cac<br>Pro Ser Ile Phe Cys Trp Phe Leu Asp Asp Asp Glu Ile Arg Asp His<br>                   350                   355                   360 | 1110 |
| atc gaa aca aac tac gag gaa ttt gct gcc gtg ctt ctt aat gtg tat<br>Ile Glu Thr Asn Tyr Glu Glu Phe Ala Ala Val Leu Leu Asn Val Tyr<br>           365                   370                   375 | 1158 |
| cga gct acc gat ctt atg ttc tcc ggc gaa gtc caa ctt gtc gaa gca<br>Arg Ala Thr Asp Leu Met Phe Ser Gly Glu Val Gln Leu Val Glu Ala<br>             380                   385                   390 | 1206 |
| aga tct ttc gct acc aag aat ctt gag aaa ata tta gca aca gga aac<br>Arg Ser Phe Ala Thr Lys Asn Leu Glu Lys Ile Leu Ala Thr Gly Asn<br>395                       400                   405 | 1254 |
| ata cat aaa act aat gca gat atc tca tct agt ttg cat aag atg atc<br>Ile His Lys Thr Asn Ala Asp Ile Ser Ser Ser Leu His Lys Met Ile<br>410                       415                   420                   425 | 1302 |
| gaa cac gaa cta aga gtt cct tgg acc gca aga atg gac cat gtt gaa<br>Glu His Glu Leu Arg Val Pro Trp Thr Ala Arg Met Asp His Val Glu<br>             430                   435                   440 | 1350 |
| aat cga att tgg atc gaa gaa ata gct tcc agt gct tta tgg ttt gga<br>Asn Arg Ile Trp Ile Glu Glu Ile Ala Ser Ser Ala Leu Trp Phe Gly<br>               445                   450                   455 | 1398 |
| aaa tca tcc tac ctt agg tta tct tgc ttt cac aag atg agt tta cag<br>Lys Ser Ser Tyr Leu Arg Leu Ser Cys Phe His Lys Met Ser Leu Gln<br>       460                   465                   470 | 1446 |

-continued

```
caa ctc gcg gtg aaa aat tat acg ctt cga caa ttg gtt tac cga gac         1494
Gln Leu Ala Val Lys Asn Tyr Thr Leu Arg Gln Leu Val Tyr Arg Asp
        475                 480                 485 gag ctt gcg gaa gtt gag agg tgg tct aaa gaa aga ggg cta tgt gac         1542
Glu Leu Ala Glu Val Glu Arg Trp Ser Lys Glu Arg Gly Leu Cys Asp
490                 495                 500                 505 atg gga ttt tgt aga gag aaa acc ggg tat tgt tac tac gca ttt gcg         1590
Met Gly Phe Cys Arg Glu Lys Thr Gly Tyr Cys Tyr Tyr Ala Phe Ala
                510                 515                 520 gca agt act tgt ctg ccg tgg agt tcc gac gtg agg ctg gtc ctg acc         1638
Ala Ser Thr Cys Leu Pro Trp Ser Ser Asp Val Arg Leu Val Leu Thr
            525                 530                 535 aag gcg gca gtt gtc att aca gtg gcc gat gat ttc ttt gat gtc gaa         1686
Lys Ala Ala Val Val Ile Thr Val Ala Asp Asp Phe Phe Asp Val Glu
        540                 545                 550 gga tct atg gtt gat ctc gaa aaa tta acg gat gca gtt cgg agg tgg         1734
Gly Ser Met Val Asp Leu Glu Lys Leu Thr Asp Ala Val Arg Arg Trp
555                 560                 565 gat gcg gaa ggg tta ggc agc cac agc aag aca ata ttt gaa gcc ctg         1782
Asp Ala Glu Gly Leu Gly Ser His Ser Lys Thr Ile Phe Glu Ala Leu
570                 575                 580                 585 gat gat ctt gta aat gaa gtt aga ctc aag tgt ttc caa caa aat gga         1830
Asp Asp Leu Val Asn Glu Val Arg Leu Lys Cys Phe Gln Gln Asn Gly
                590                 595                 600 caa gac atc aaa aac aat ctc caa caa tta tgg tat gaa aca ttc cat         1878
Gln Asp Ile Lys Asn Asn Leu Gln Gln Leu Trp Tyr Glu Thr Phe His
            605                 610                 615 tca tgg ctt atg gaa gct aag tgg gga aag ggg tta aca agt aaa cca         1926
Ser Trp Leu Met Glu Ala Lys Trp Gly Lys Gly Leu Thr Ser Lys Pro
        620                 625                 630 tct gta gat gtg tat ctt gga aat gca atg aca tcc ata gca gct cac         1974
Ser Val Asp Val Tyr Leu Gly Asn Ala Met Thr Ser Ile Ala Ala His
635                 640                 645 acc atg gtc ctt aca gca tcc tgt ctt cta ggt ccc ggt ttc ccg gtt         2022
Thr Met Val Leu Thr Ala Ser Cys Leu Leu Gly Pro Gly Phe Pro Val
650                 655                 660                 665 cac caa cta tgg tcg caa agg cgc cac cag gac att aca tcc ttg ctc         2070
His Gln Leu Trp Ser Gln Arg Arg His Gln Asp Ile Thr Ser Leu Leu
                670                 675                 680 atg gtc ttg act cgc ttg cta aat gac att caa tcc tac ttg aaa gaa         2118
Met Val Leu Thr Arg Leu Leu Asn Asp Ile Gln Ser Tyr Leu Lys Glu
            685                 690                 695 gaa gac gaa gga aaa ata aac tat gta tgg atg tac atg atc gag aac         2166
Glu Asp Glu Gly Lys Ile Asn Tyr Val Trp Met Tyr Met Ile Glu Asn
        700                 705                 710 aat caa gcg tcg ata gat gac tcg gtt cga cac gtc cag acg ata atc         2214
Asn Gln Ala Ser Ile Asp Asp Ser Val Arg His Val Gln Thr Ile Ile
715                 720                 725 aat gta aaa aag caa gaa ttc atc caa cgt gtt cta tcg gat caa cat         2262
Asn Val Lys Lys Gln Glu Phe Ile Gln Arg Val Leu Ser Asp Gln His
730                 735                 740                 745 tgc aat ctc cca aag tca ttc aag cag ctc cat ttc tcc tgc ctc aaa         2310
Cys Asn Leu Pro Lys Ser Phe Lys Gln Leu His Phe Ser Cys Leu Lys
                750                 755                 760 gta ttc aac atg ttc ttc aac tcc tcc aac att ttc gac act gat acc         2358
Val Phe Asn Met Phe Phe Asn Ser Ser Asn Ile Phe Asp Thr Asp Thr
            765                 770                 775 gac ctt ctt ctt gac att cac gaa gct ttt gtt tct cca cca caa gtt         2406
Asp Leu Leu Leu Asp Ile His Glu Ala Phe Val Ser Pro Pro Gln Val
        780                 785                 790
```

-continued

```
ccc aaa ttc aaa ccc cac atc aag cca cct cat cag ctt cca gca aca    2454
Pro Lys Phe Lys Pro His Ile Lys Pro Pro His Gln Leu Pro Ala Thr
    795                 800                 805 ctt cag cca cct cat cag ccc caa caa ata atg gtc aat aag aag aag    2502
Leu Gln Pro Pro His Gln Pro Gln Gln Ile Met Val Asn Lys Lys Lys
810                 815                 820                 825 gtg gaa atg gtt tac aaa agc tat cat cat cca ttc aag gtt ttc acc    2550
Val Glu Met Val Tyr Lys Ser Tyr His His Pro Phe Lys Val Phe Thr
                830                 835                 840 ttg cag aag aaa caa agt tcg gga cat ggt aca atg aat cca agg gct    2598
Leu Gln Lys Lys Gln Ser Ser Gly His Gly Thr Met Asn Pro Arg Ala
            845                 850                 855 agt atc tta gca gga ccc aac atc aaa cta tgt ttc agt taacgaatac    2647
Ser Ile Leu Ala Gly Pro Asn Ile Lys Leu Cys Phe Ser
        860                 865                 870 actaccttgt tattagaaga tgtcaccagt ttcc                              2681
```

<210> SEQ ID NO 8
<211> LENGTH: 870
<212> TYPE: PRT
<213> ORGANISM: Clarkia breweri

<400> SEQUENCE: 8

```
Met Gln Leu Ile Thr Asn Phe Ser Ser Ser Ser Glu Leu Gln Phe
 1               5                  10                  15

Leu Val Asp Lys Val Lys Arg Glu Ser Leu Ser Ser Ser Ser Asn
                20                  25                  30

Thr Gln Asn Leu Phe Leu Ser Thr Ser Pro Tyr Asp Thr Ala Trp Leu
            35                  40                  45

Ala Leu Ile Pro His Pro His His His His His Gly Arg Pro Met
         50                  55                  60

Phe Glu Lys Cys Leu Gln Trp Ile Leu His Asn Gln Thr Pro Gln Gly
 65                  70                  75                  80

Phe Trp Ala Ala Ala Gly Asp Asn Ile Ser Asp Thr Asp Asp Val
                85                  90                  95

Thr Leu Asp Cys Leu Leu Ser Thr Leu Ala Cys Leu Val Ala Leu Lys
            100                 105                 110

Arg Trp Gln Leu Ala Pro Asp Met Ile His Lys Gly Leu Glu Phe Val
        115                 120                 125

Asn Arg Asn Thr Glu Arg Leu Val Met Lys Gln Lys Pro Ser Asp Val
    130                 135                 140

Pro Arg Trp Phe Thr Ile Met Phe Pro Ala Met Leu Glu Leu Ala Gly
145                 150                 155                 160

Ala Ser Ser Leu Arg Val Asp Phe Ser Glu Asn Leu Asn Arg Ile Leu
                165                 170                 175

Val Glu Leu Ser Gln Asn Arg Asp Asp Ile Leu Thr Arg Glu Val
            180                 185                 190

Asp Glu Lys Lys Gln Tyr Ser Pro Leu Leu Leu Phe Leu Glu Ala Leu
        195                 200                 205

Pro Ala Gln Ser Tyr Asp Asn Asp Val Leu Lys Gln Ile Ile Asp Lys
    210                 215                 220

Asn Leu Ser Asn Asp Gly Ser Leu Leu Gln Ser Pro Ser Ala Thr Ala
225                 230                 235                 240

Arg Ala Tyr Met Ile Thr Gly Asn Thr Arg Cys Leu Ser Tyr Leu His
                245                 250                 255
```

-continued

```
Ser Leu Thr Asn Ser Cys Ser Asn Gly Gly Val Pro Ser Phe Tyr Pro
            260                 265                 270

Val Asp Asp Leu His Asp Leu Val Met Val Asn Gln Leu Thr Arg
        275                 280                 285

Ser Gly Leu Thr Glu His Leu Ile Pro Glu Ile Asp His Leu Leu Leu
        290                 295                 300

Lys Val Gln Lys Asn Tyr Lys Tyr Lys Lys Ala Ser Pro Lys Ser Leu
305                 310                 315                 320

Tyr Ser Ile Ala Ala Glu Leu Tyr Arg Asp Ser Leu Ala Phe Trp Leu
                325                 330                 335

Leu Arg Val Asn Asn His Trp Val Ser Pro Ser Ile Phe Cys Trp Phe
            340                 345                 350

Leu Asp Asp Asp Glu Ile Arg Asp His Ile Glu Thr Asn Tyr Glu Glu
            355                 360                 365

Phe Ala Ala Val Leu Leu Asn Val Tyr Arg Ala Thr Asp Leu Met Phe
            370                 375                 380

Ser Gly Glu Val Gln Leu Val Glu Ala Arg Ser Phe Ala Thr Lys Asn
385                 390                 395                 400

Leu Glu Lys Ile Leu Ala Thr Gly Asn Ile His Lys Thr Asn Ala Asp
                405                 410                 415

Ile Ser Ser Ser Leu His Lys Met Ile Glu His Glu Leu Arg Val Pro
            420                 425                 430

Trp Thr Ala Arg Met Asp His Val Glu Asn Arg Ile Trp Ile Glu Glu
            435                 440                 445

Ile Ala Ser Ser Ala Leu Trp Phe Gly Lys Ser Ser Tyr Leu Arg Leu
450                 455                 460

Ser Cys Phe His Lys Met Ser Leu Gln Gln Leu Ala Val Lys Asn Tyr
465                 470                 475                 480

Thr Leu Arg Gln Leu Val Tyr Arg Asp Glu Leu Ala Glu Val Glu Arg
                485                 490                 495

Trp Ser Lys Glu Arg Gly Leu Cys Asp Met Gly Phe Cys Arg Glu Lys
            500                 505                 510

Thr Gly Tyr Cys Tyr Tyr Ala Phe Ala Ala Ser Thr Cys Leu Pro Trp
            515                 520                 525

Ser Ser Asp Val Arg Leu Val Leu Thr Lys Ala Ala Val Val Ile Thr
            530                 535                 540

Val Ala Asp Asp Phe Phe Asp Val Glu Gly Ser Met Val Asp Leu Glu
545                 550                 555                 560

Lys Leu Thr Asp Ala Val Arg Arg Trp Asp Ala Glu Gly Leu Gly Ser
                565                 570                 575

His Ser Lys Thr Ile Phe Glu Ala Leu Asp Asp Leu Val Asn Glu Val
            580                 585                 590

Arg Leu Lys Cys Phe Gln Gln Asn Gly Gln Asp Ile Lys Asn Asn Leu
            595                 600                 605

Gln Gln Leu Trp Tyr Glu Thr Phe His Ser Trp Leu Met Glu Ala Lys
            610                 615                 620

Trp Gly Lys Gly Leu Thr Ser Lys Pro Ser Val Asp Val Tyr Leu Gly
625                 630                 635                 640

Asn Ala Met Thr Ser Ile Ala Ala His Thr Met Val Leu Thr Ala Ser
                645                 650                 655

Cys Leu Leu Gly Pro Gly Phe Pro Val His Gln Leu Trp Ser Gln Arg
            660                 665                 670
```

```
Arg His Gln Asp Ile Thr Ser Leu Leu Met Val Leu Thr Arg Leu Leu
        675                 680                 685

Asn Asp Ile Gln Ser Tyr Leu Lys Glu Glu Asp Glu Gly Lys Ile Asn
        690                 695                 700

Tyr Val Trp Met Tyr Met Ile Glu Asn Asn Gln Ala Ser Ile Asp Asp
705                 710                 715                 720

Ser Val Arg His Val Gln Thr Ile Ile Asn Val Lys Lys Gln Glu Phe
                725                 730                 735

Ile Gln Arg Val Leu Ser Asp Gln His Cys Asn Leu Pro Lys Ser Phe
            740                 745                 750

Lys Gln Leu His Phe Ser Cys Leu Lys Val Phe Asn Met Phe Phe Asn
        755                 760                 765

Ser Ser Asn Ile Phe Asp Thr Asp Thr Asp Leu Leu Leu Asp Ile His
        770                 775                 780

Glu Ala Phe Val Ser Pro Pro Gln Val Pro Lys Phe Lys Pro His Ile
785                 790                 795                 800

Lys Pro Pro His Gln Leu Pro Ala Thr Leu Gln Pro Pro His Gln Pro
                805                 810                 815

Gln Gln Ile Met Val Asn Lys Lys Val Glu Met Val Tyr Lys Ser
                820                 825                 830

Tyr His His Pro Phe Lys Val Phe Thr Leu Gln Lys Lys Gln Ser Ser
        835                 840                 845

Gly His Gly Thr Met Asn Pro Arg Ala Ser Ile Leu Ala Gly Pro Asn
        850                 855                 860

Ile Lys Leu Cys Phe Ser
865                 870
```